United States Patent [19]
Chin et al.

[11] Patent Number: 5,803,901
[45] Date of Patent: Sep. 8, 1998

[54] INFLATABLE DEVICES FOR SEPARATING LAYERS OF TISSUE AND METHODS OF USING

[75] Inventors: Albert K. Chin, Palo Alto; Todd A. Thompson, Sunnyvale, both of Calif.

[73] Assignee: Origin Medsystems, Inc., Menlo Park, Calif.

[21] Appl. No.: 816,251

[22] Filed: Mar. 13, 1997

Related U.S. Application Data

[63] Continuation of Ser. No. 365,096, Dec. 28, 1994, abandoned, which is a continuation-in-part of Ser. No. 319,552, Oct. 7, 1994, Pat. No. 5,643,310, which is a continuation-in-part of Ser. No. 282,287, Jul. 29, 1994, abandoned, which is a continuation-in-part of Ser. No. 911,714, Jul. 10, 1992, which is a continuation-in-part of Ser. No. 794,590, Nov. 19, 1991, Pat. No. 5,309,896, which is a continuation-in-part of Ser. No. 706,781, May 29, 1991, abandoned.

[51] Int. Cl.$^6$ ........................................ A61B 19/00
[52] U.S. Cl. ........................................ 600/190; 600/207
[58] Field of Search ........................ 606/1, 191–200; 604/96–104; 600/201, 204, 207

[56] References Cited

U.S. PATENT DOCUMENTS

| | | |
|---|---|---|
| 1,060,350 | 4/1913 | Miller . |
| 1,275,520 | 8/1918 | Bell . |
| 1,947,649 | 2/1934 | Kadavy . |
| 2,663,020 | 12/1953 | Cushman . |
| 3,039,468 | 6/1962 | Price . |
| 3,417,745 | 12/1968 | Sheldon . |
| 3,626,949 | 12/1971 | Shute . |
| 3,774,596 | 11/1973 | Cook . |
| 3,782,370 | 1/1974 | McDonald . |
| 3,831,587 | 8/1974 | Boyd . |
| 3,863,639 | 2/1975 | Kleaveland . |
| 3,882,852 | 5/1975 | Sinnreich . |
| 3,961,632 | 6/1976 | Moossun . |
| 4,077,412 | 3/1978 | Moossun . |

(List continued on next page.)

FOREIGN PATENT DOCUMENTS

| | | |
|---|---|---|
| B-516114 | 5/1981 | Australia . |
| A 0 246 086 | of 0000 | European Pat. Off. . |
| A 0 010 650 | 5/1980 | European Pat. Off. . |
| A 0 251 976 | 1/1988 | European Pat. Off. . |
| A 0 275 230 | 7/1988 | European Pat. Off. . |
| WO 93/11824 | 12/1992 | European Pat. Off. . |
| 2 474 304 | 7/1981 | France . |
| 2 646 088 | 10/1990 | France . |
| A 2 688 695 | 5/1992 | France . |
| A 2 847 633 | 5/1979 | Germany . |
| U 91-04 383 | 7/1991 | Germany . |
| 797 668 | 1/1991 | U.S.S.R. . |
| A 2 071 502 | 9/1981 | United Kingdom . |

OTHER PUBLICATIONS ed. G. Berci, Endoscopy, Appleton–Century–Crofts, 1976, pp. 382–385 and 412.
Unknown—Laparoscopy for Sterilization, Section 1, A Chronology of Laparoscopy.
"New Surgical Procedures for Indirect Hernias"—Product leaflet for Herniastat™ disosable automatic surgical stapling device published by Innovative Surgical Devices, Inc., date unknown.
"A Tiny TV Camera is Fast Transforming Gallbladder Surgery," Wall Street Journal, Dec. 10, 1990, p. A1, continued on p. A5.
A Comprehensive Guide to Purchasing [Hospital Supplies], V. Mueller & Co., Chicago, 1956, p. 829.

(List continued on next page.)

Primary Examiner—Glenn K. Dawson
Attorney, Agent, or Firm—Limbach & Limbach L.L.P.

[57] ABSTRACT

An apparatus and method for separating a first layer of tissue from a second layer of tissue. A supporting part extends into the interior of the balloon during inflation to provide support for the balloon. The supporting part is retracted to a position outside the interior of the balloon after inflating the balloon. An endoscope is then inserted into the interior of the balloon. The endoscope is moved within the interior of the balloon to change the field of view of the endoscope.

14 Claims, 35 Drawing Sheets

U.S. PATENT DOCUMENTS

| | | | |
|---|---|---|---|
| 4,083,369 | 4/1978 | Sinnreich . | |
| 4,137,906 | 2/1979 | Akiyama et al. . | |
| 4,183,102 | 1/1980 | Guiset | 604/101 |
| 4,240,433 | 12/1980 | Bordow . | |
| 4,254,762 | 3/1981 | Yoon . | |
| 4,271,839 | 6/1981 | Fogarty et al. . | |
| 4,291,687 | 9/1981 | Sinnreich . | |
| 4,318,410 | 3/1982 | Chin . | |
| 4,357,940 | 11/1982 | Muller . | |
| 4,430,076 | 2/1984 | Harris | 604/96 |
| 4,447,227 | 5/1984 | Kotsanis | 604/95 |
| 4,493,711 | 1/1985 | Chin et al. | 604/271 |
| 4,535,773 | 8/1985 | Yoon | 604/51 |
| 4,598,699 | 7/1986 | Garren et al. . | |
| 4,601,710 | 7/1986 | Moll | 604/165 |
| 4,654,030 | 3/1987 | Moll et al. | 604/165 |
| 4,709,697 | 12/1987 | Muller . | |
| 4,744,363 | 5/1988 | Hasson . | |
| 4,775,371 | 10/1988 | Mueller, Jr. | 604/280 |
| 4,779,611 | 10/1988 | Grooters et al. . | |
| 4,863,440 | 9/1989 | Chin | 604/271 |
| 4,919,152 | 4/1990 | Ger . | |
| 4,944,443 | 7/1990 | Oddsen et al. . | |
| 4,966,583 | 10/1990 | Debbas | 604/98 |
| 4,984,564 | 1/1991 | Yuen . | |
| 5,002,557 | 3/1991 | Hasson | 606/191 |
| 5,007,898 | 4/1991 | Rosenbluth et al. | 604/54 |
| 5,082,005 | 1/1992 | Kaldany . | |
| 5,083,576 | 1/1992 | Reuiz-Razura et al. | 128/898 |
| 5,122,122 | 6/1992 | Allgood | 604/169 |
| 5,122,155 | 6/1992 | Eberback | 606/213 |
| 5,141,515 | 8/1992 | Eberbach . | |
| 5,163,949 | 11/1992 | Bonutti | 606/192 |
| 5,176,128 | 1/1993 | Andrese . | |
| 5,176,692 | 1/1993 | Wilk et al. | 606/151 |
| 5,176,697 | 1/1993 | Hasson et al. | 606/191 |
| 5,183,463 | 2/1993 | Debbas | 604/98 |
| 5,183,464 | 2/1993 | Dubrul et al. | 604/96 |
| 5,188,630 | 2/1993 | Christoudias | 606/108 |
| 5,195,507 | 3/1993 | Bilweis . | |
| 5,197,948 | 3/1993 | Ghodsian | 604/30 |
| 5,197,971 | 3/1993 | Bonutti | 604/96 |
| 5,269,753 | 12/1993 | Wilk | 604/49 |
| 5,309,896 | 5/1994 | Moll et al. . | |
| 5,318,013 | 6/1994 | Wilk . | |
| 5,425,357 | 6/1995 | Moll et al. | 606/192 |
| 5,439,476 | 8/1995 | Frantzides | 606/192 |
| 5,496,345 | 3/1996 | Kieturakis et al. | 606/192 |
| 5,607,443 | 3/1997 | Kieturakis et al. | 606/192 |

OTHER PUBLICATIONS

H. Nagai et al., A New Method of Laparoscopic Cholecystectomy: An Abdominal Wall Lifting Technique* Without Pneumoperitoneum, Surgical Laparoscopy and Endoscopy, vol. 1, No. 2, 1991, p. 126.

M.M. Gazayerli, "The Gazayerli Endoscopic Retractor, Model 1;" Surgical Laparoscopy & Endoscopy, vol. 1 No. 2, pp. 98–100, Raven Press, New York, Jun. 1991.

Geza J. Jako & Stephen Rozsos, "Preliminary Report: Endoscopic Laser Microsurgical Removal of Human* Gallbladder," J. Laparoendoscopic Surgery, vol. 1, No. 4, 1991.

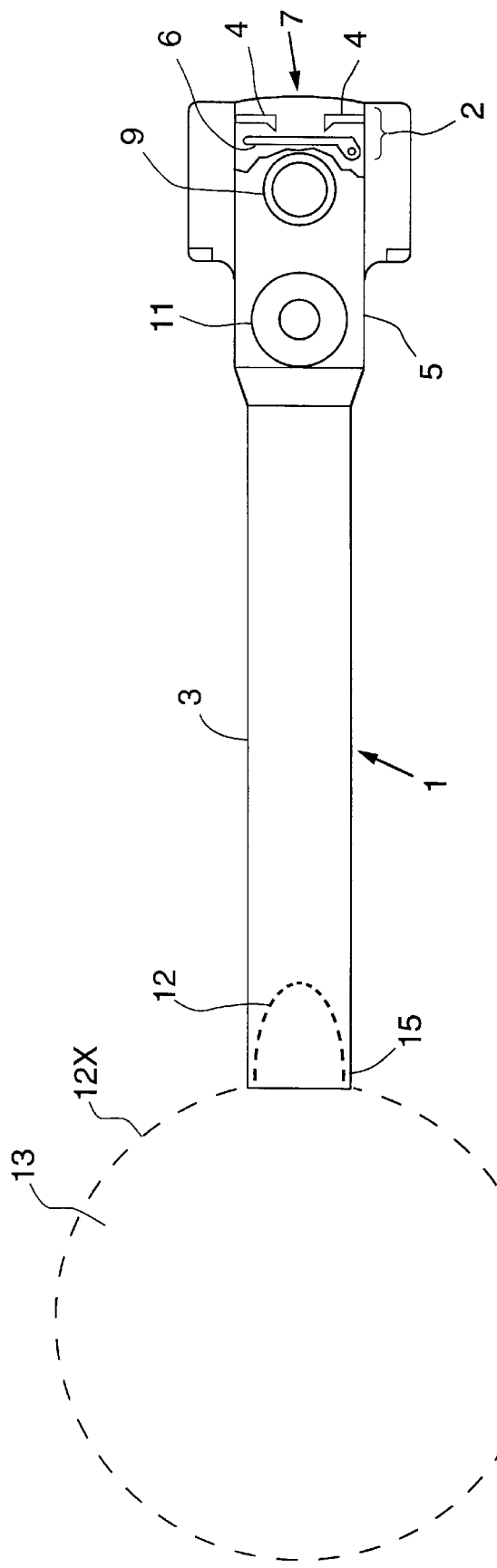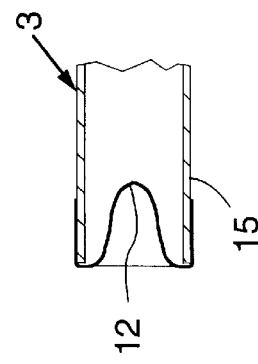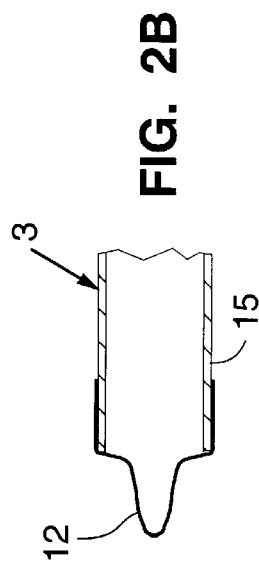

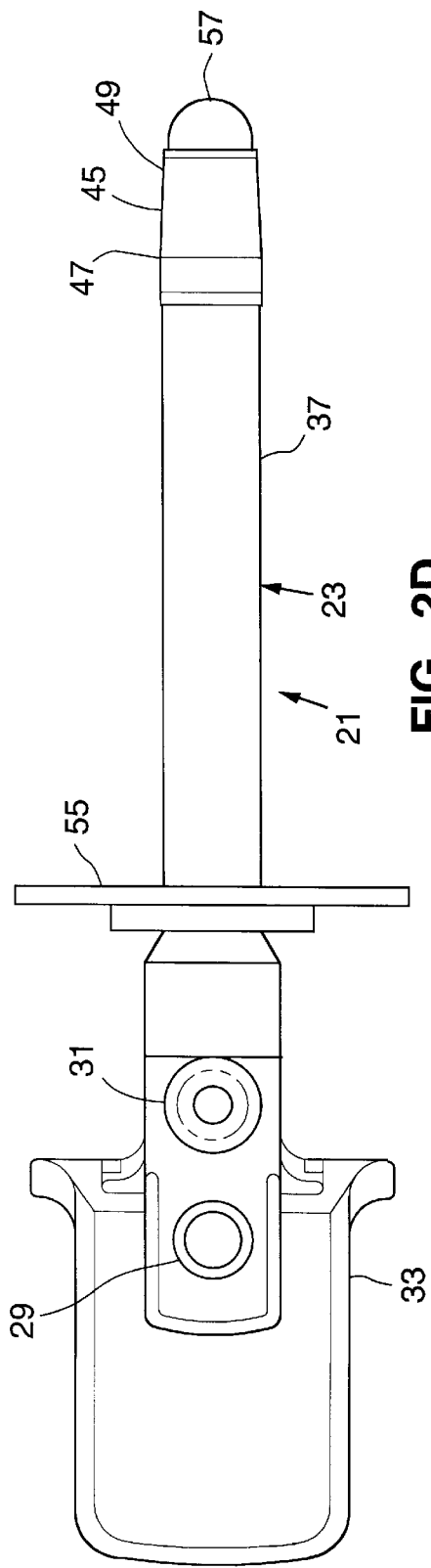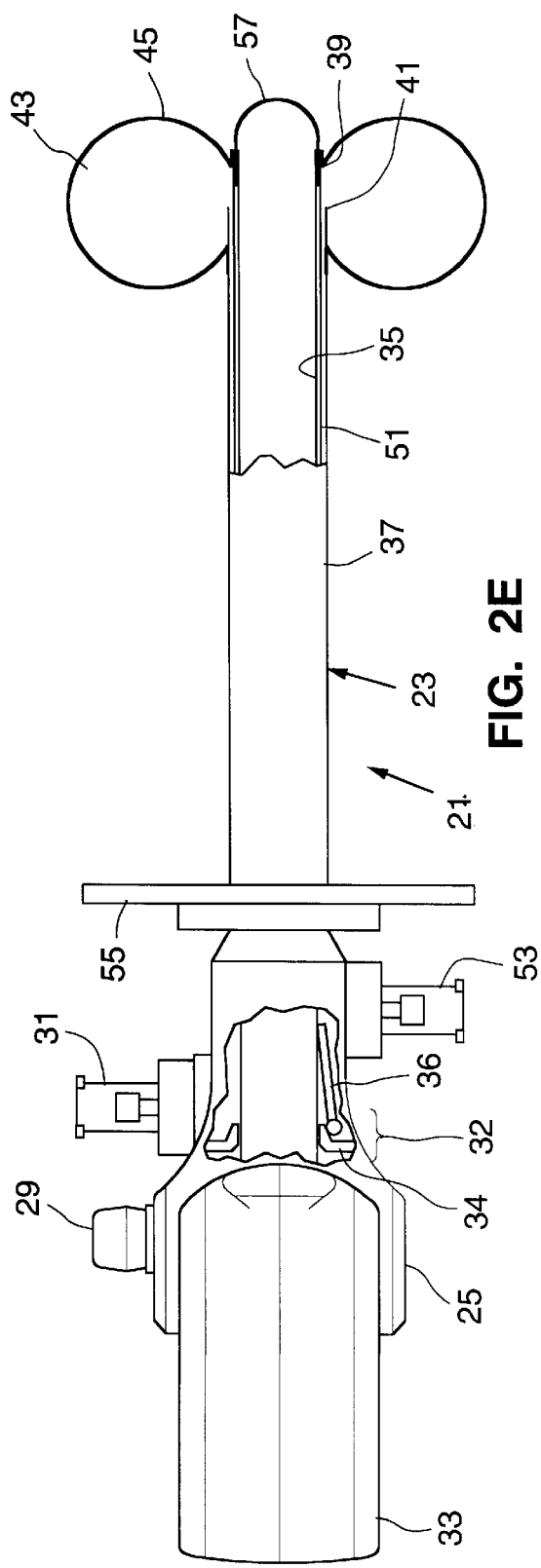

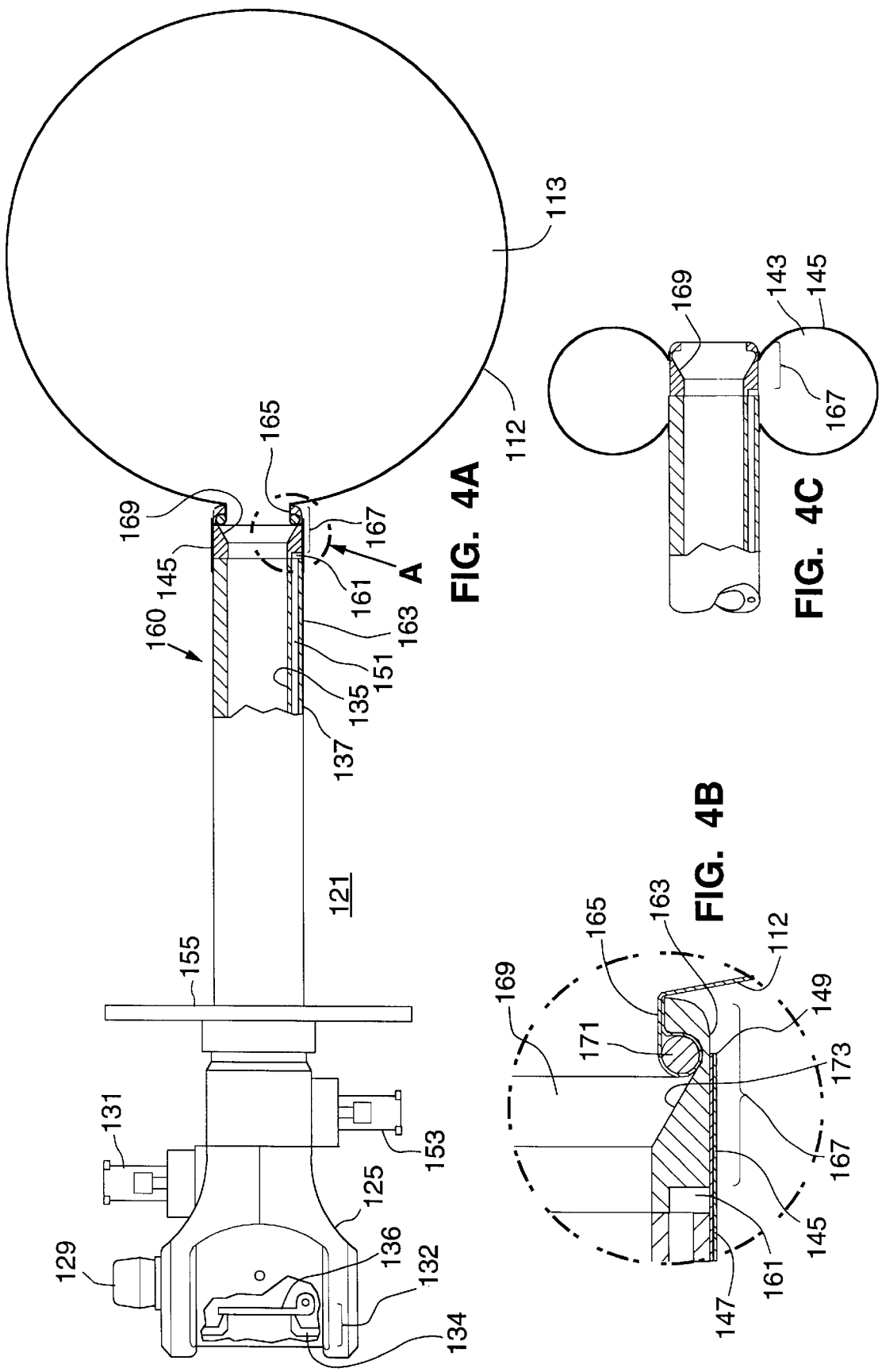

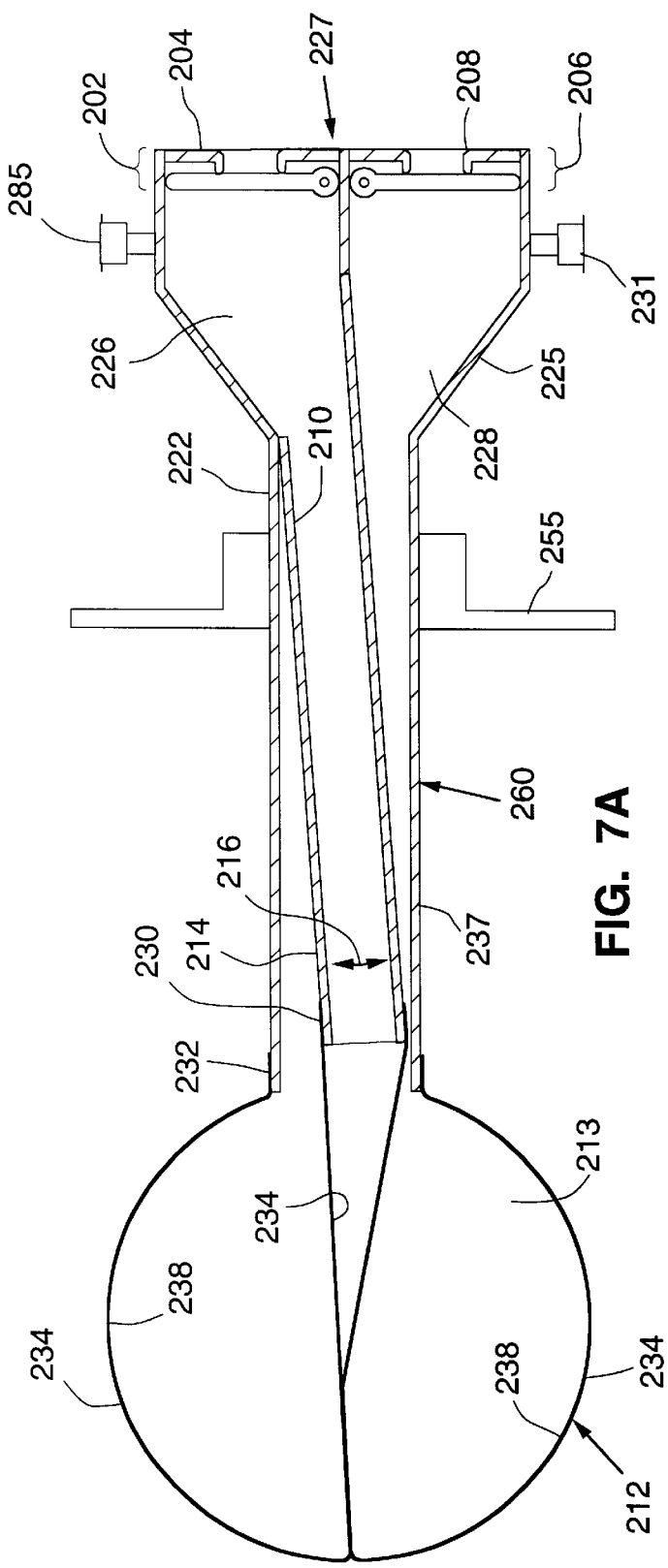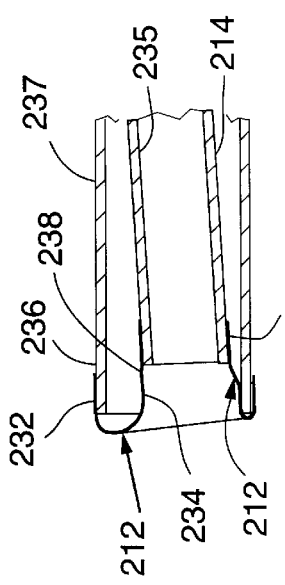

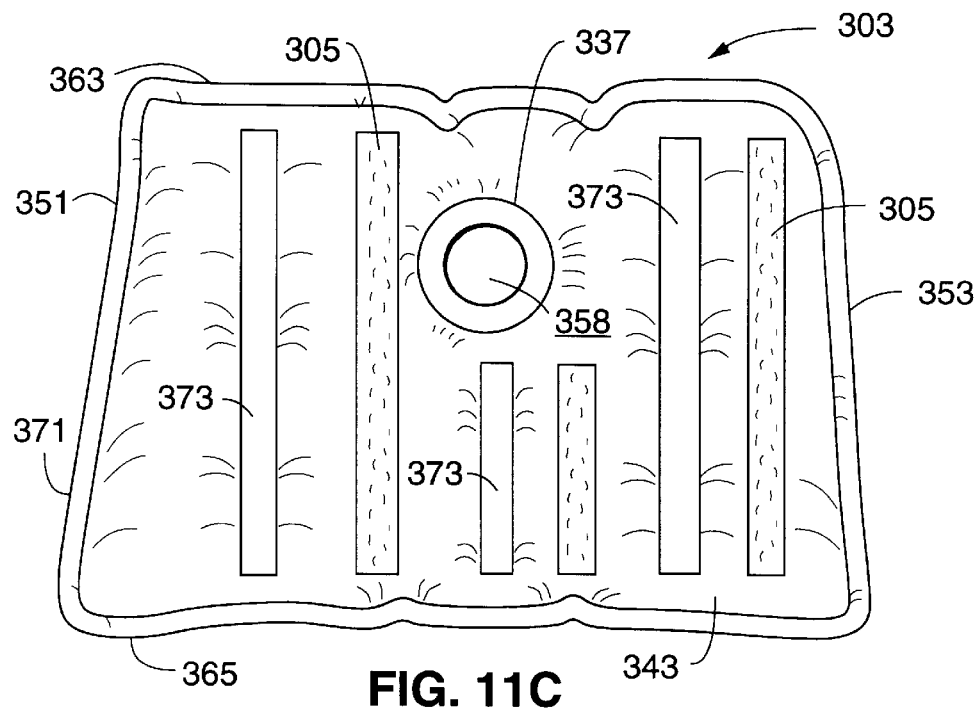
FIG. 11C
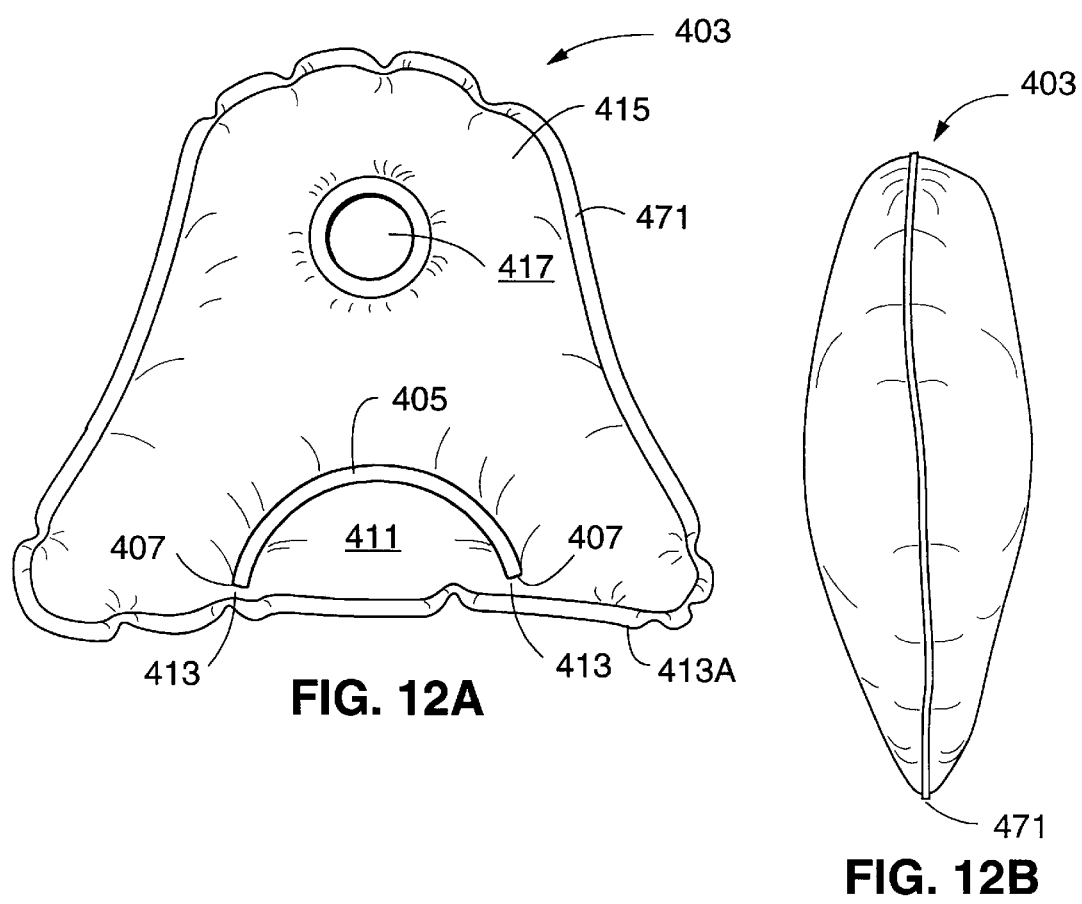
FIG. 12A
FIG. 12B

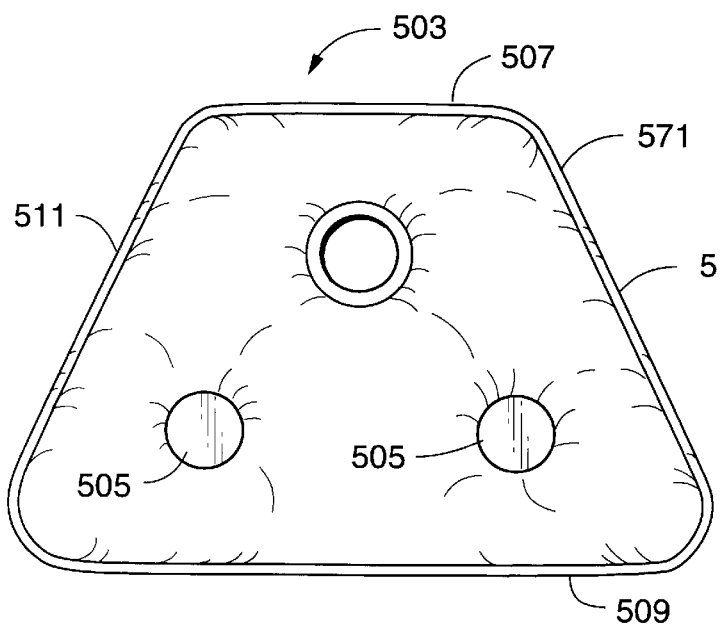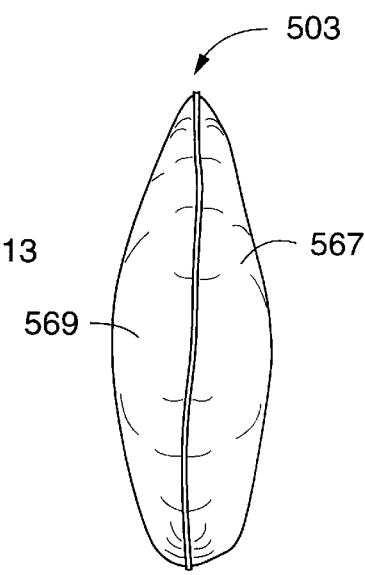
FIG. 14A  FIG. 14B
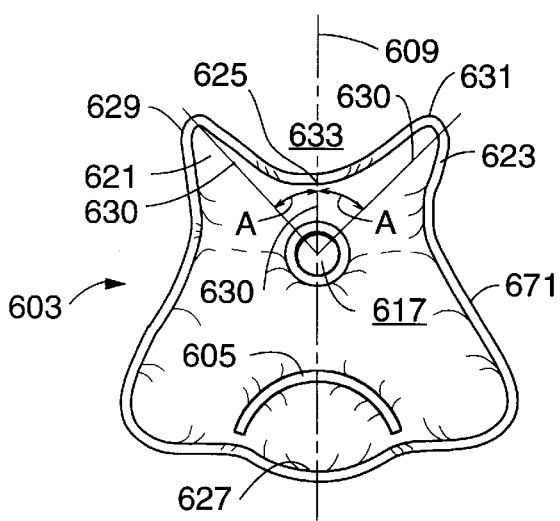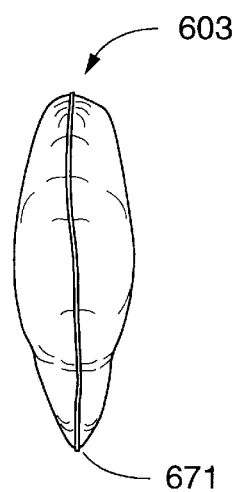
FIG. 15A  FIG. 15B
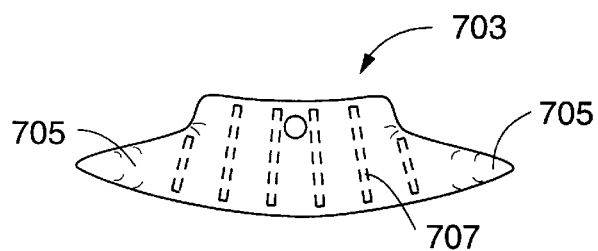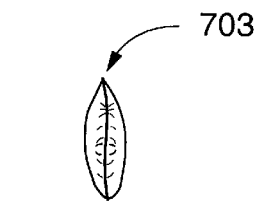
FIG. 16A  FIG. 16B

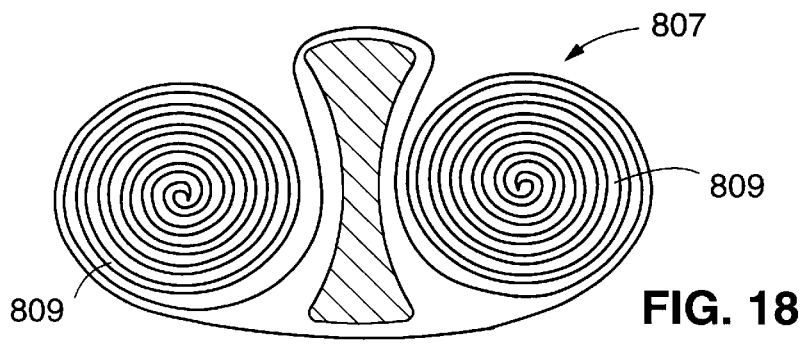
FIG. 18
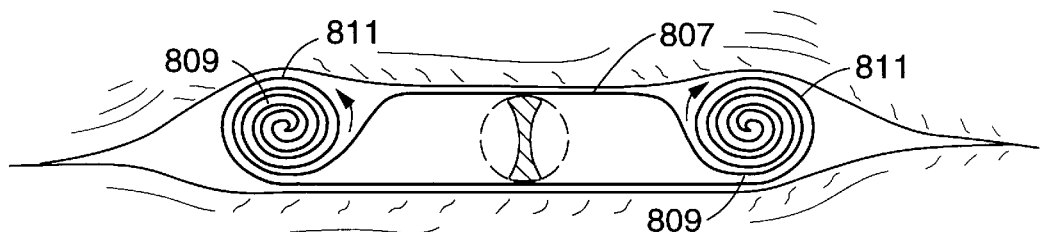
FIG. 19
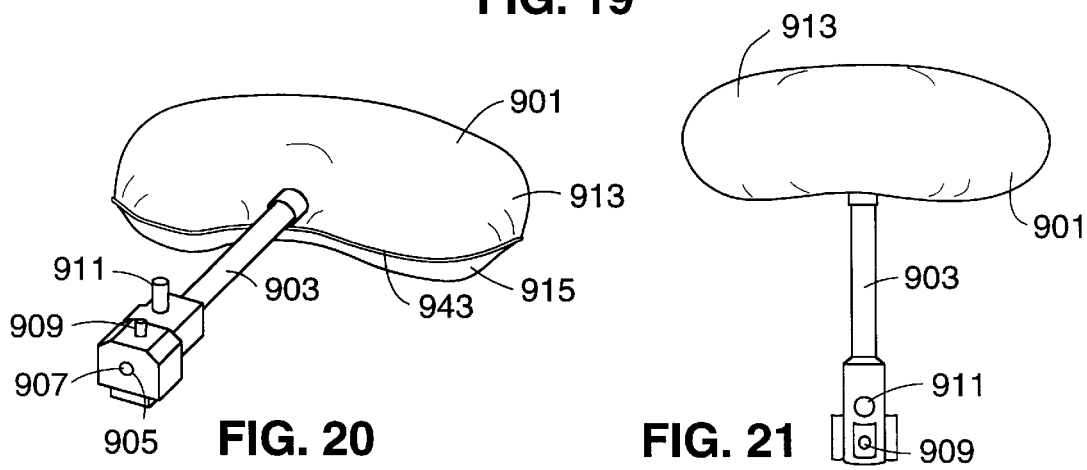
FIG. 20
FIG. 21
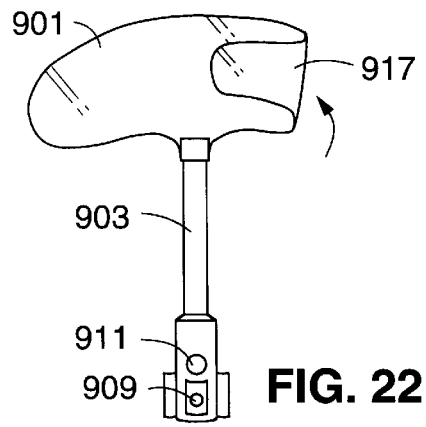
FIG. 22
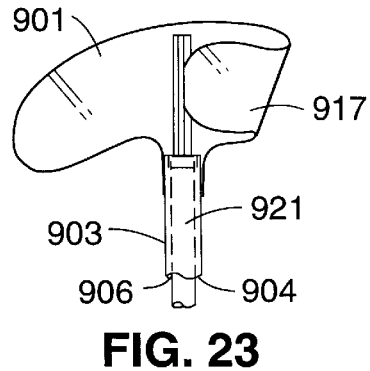
FIG. 23

BLIND AREA OF BALLOON

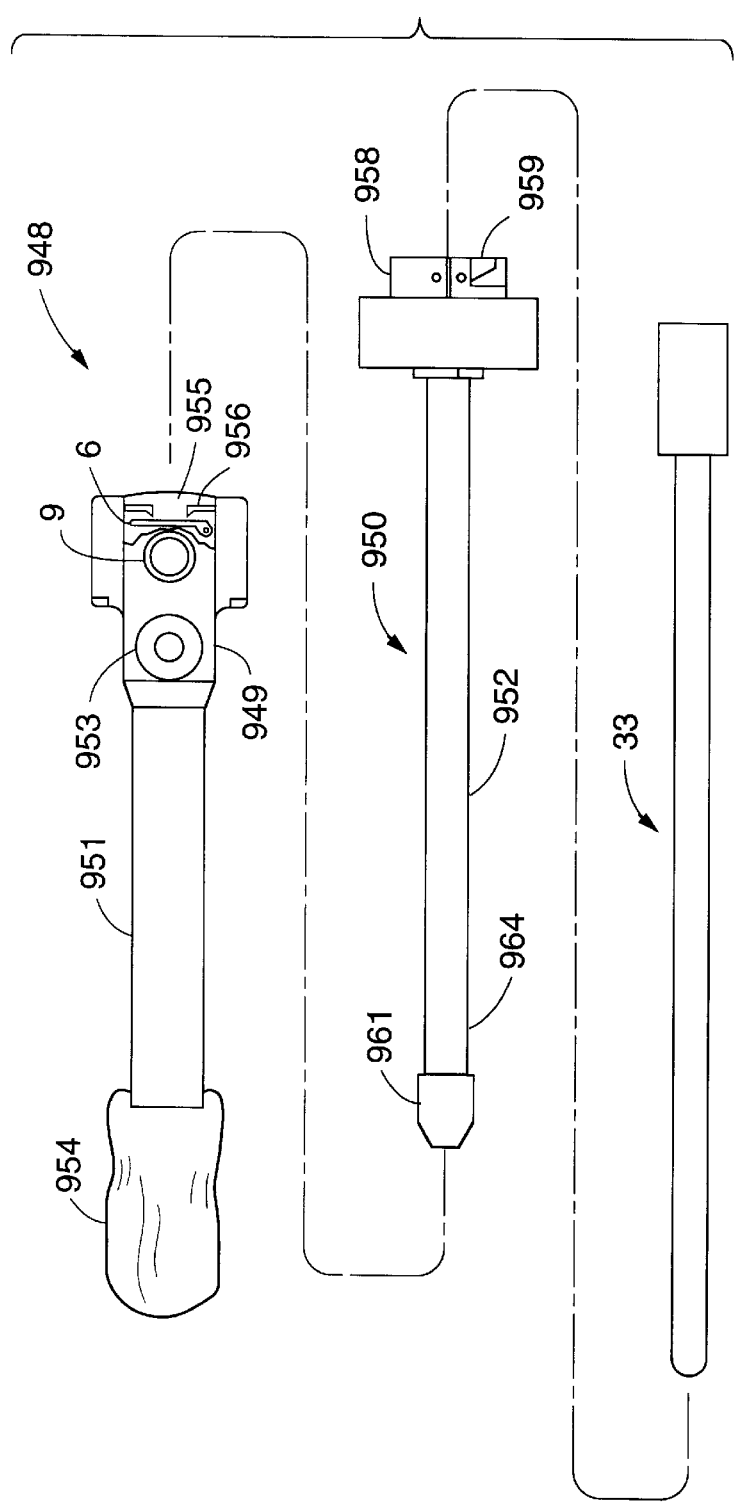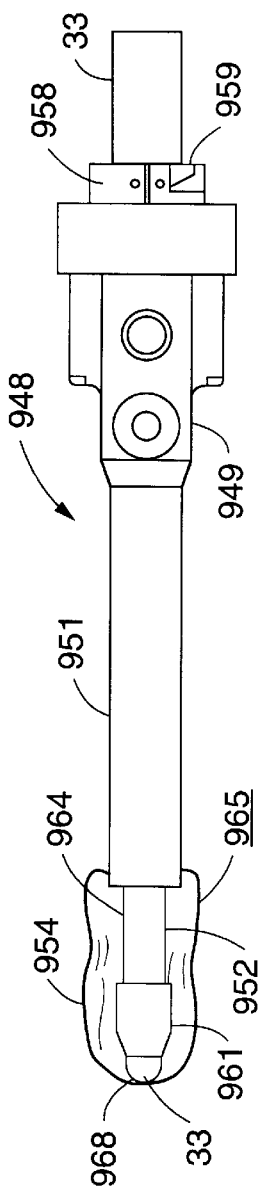

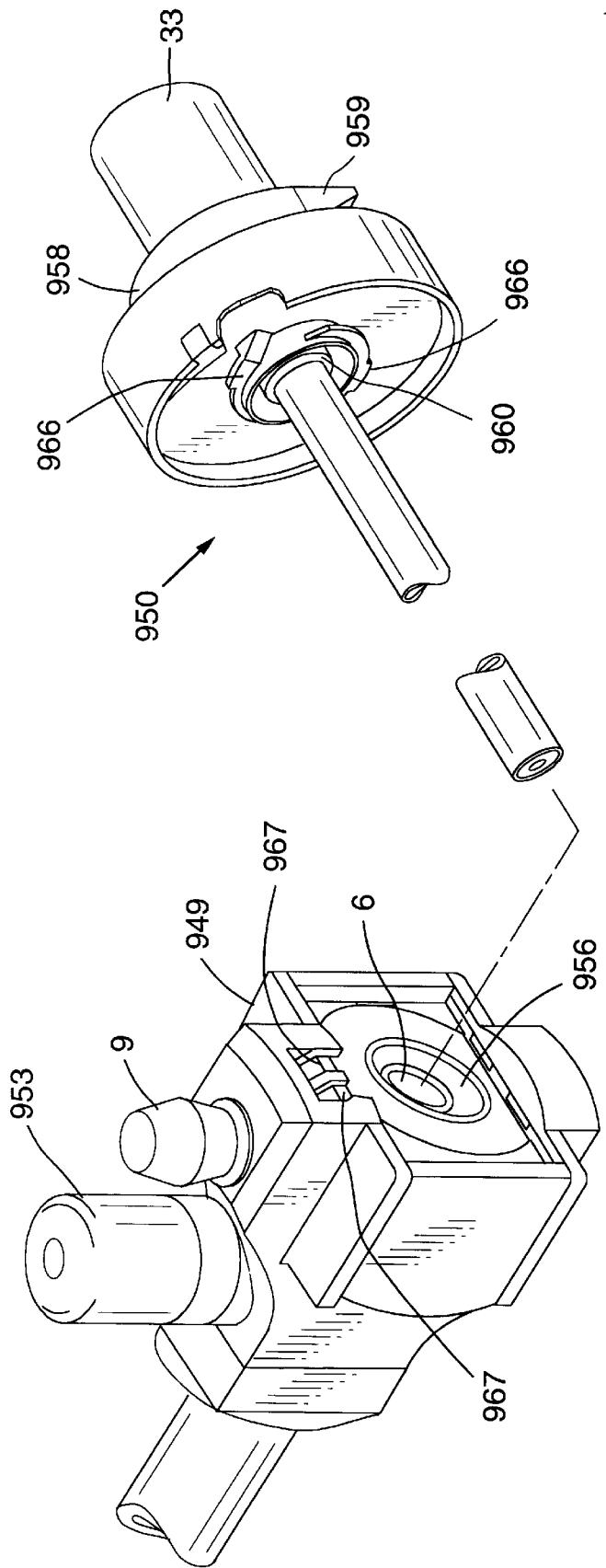
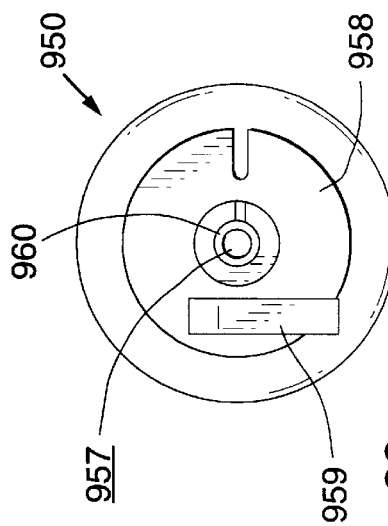
FIG. 37
FIG. 38

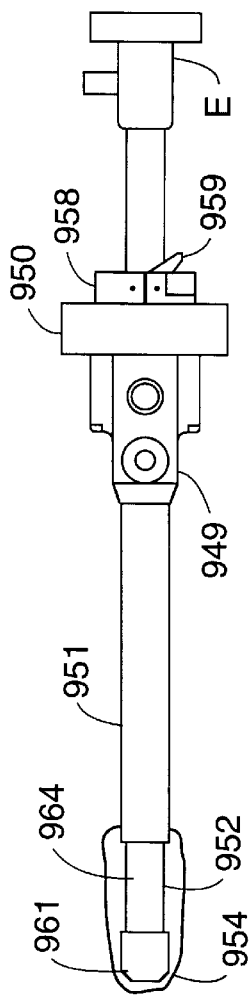
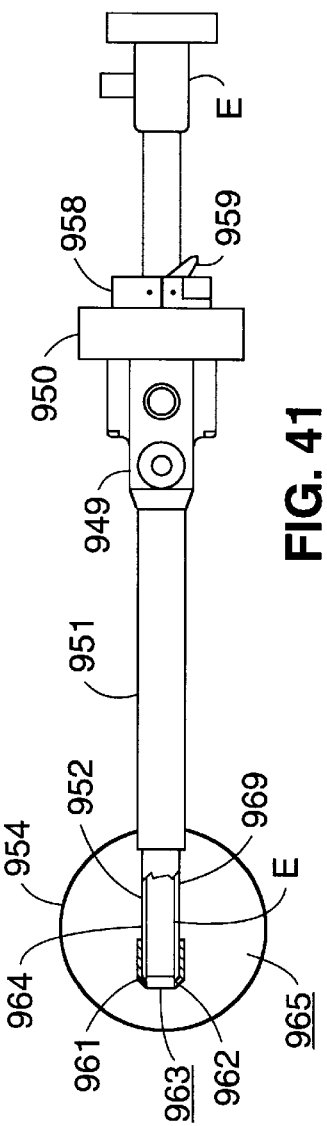
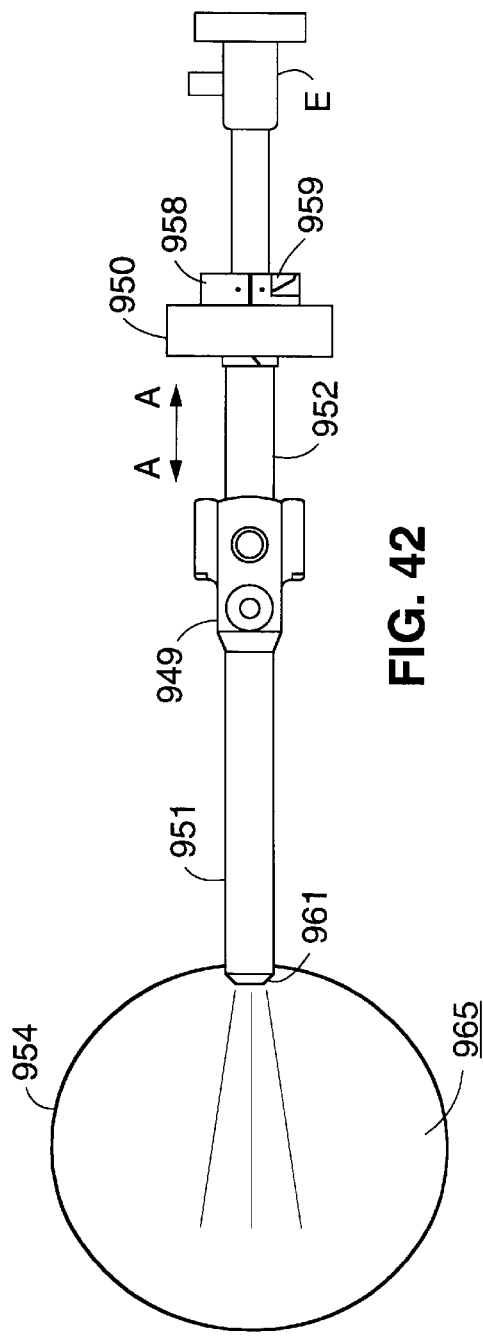
FIG. 40
FIG. 41
FIG. 42

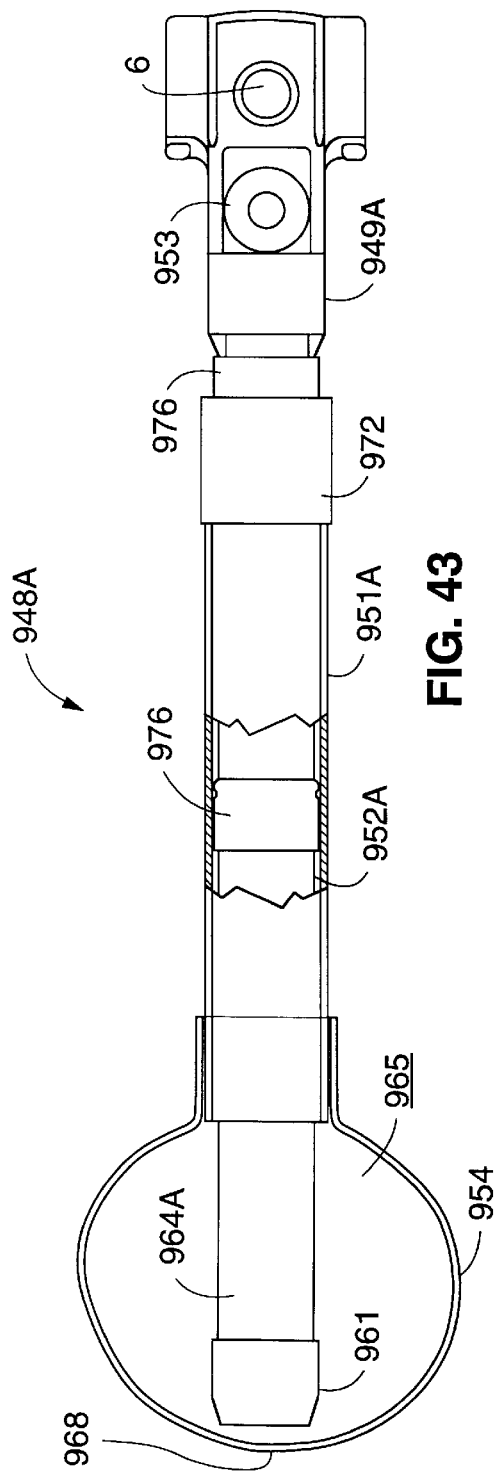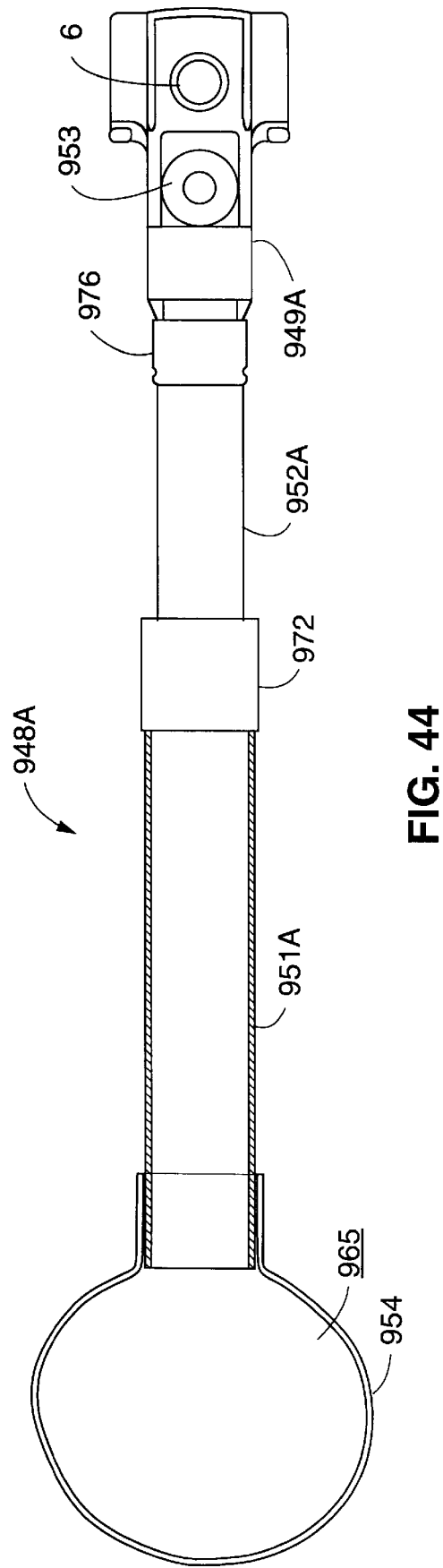
FIG. 43
FIG. 44

INFLATABLE DEVICES FOR SEPARATING LAYERS OF TISSUE AND METHODS OF USING

This is a continuation of application Ser. No. 08/365,096 filed on Dec. 28, 1994, now abandoned, which is a continuation in part of Ser. No. 08/319,552, filed Oct. 7, 1994 of inventors Albert K. Chin, Jeffrey A. Smith, John P. Lunsford and Frederic H. Moll now U.S. Pat. No. 5,643,310, which is a continuation in part of Ser. No. 08/282,287, filed Jul. 29, 1994 of inventors Frederic H. Moll, Jeff Smith, John P. Lunsford and Albert K. Chin, now abandoned, which is a Continuation-in-Part of application Ser. No. 911,714, filed Jul. 10, 1992, of inventors Albert K. Chin and John P. Lunsford, which is a Continuation-in-Part of application Ser. No. 794,590, filed 19 Nov. 1991, now issued as U.S. Pat. No. 5,309,896, of inventors Frederic H. Moll, Charles Gresl, Jr., Albert K. Chin, and Philip K. Hopper, which is a Continuation-in-Part of application Ser. No. 706,781, filed 29 May 1991, now abandoned, of inventors Frederic H. Moll, Albert K. Chin, Diane E. Caramore, and Frank T. Watkins III.

BACKGROUND OF THE INVENTION

The present invention relates to the field of inflatable tissue separation devices and methods of using such devices. The apparatus and methods of the present invention may be used in any procedure requiring dissection and/or retraction of tissue planes throughout the body including inguinal hernia repair, pelvic lymphadenectomy and bladder neck suspension in the preperitoneal space; renal, adrenal, aortic and anterior spinal access in the retroperitoneal space; penile prosthetic reservoir placement in the anterior abdominal wall; and augmentation mammaplasty prosthetic placement. By way of example only, use of such devices and methods for hernia repair will be described.

A hernia is the protrusion of part of a body part or structure through a defect in the wall of a surrounding structure. Most commonly, a hernia is the protrusion of part of abdominal contents, including bowel, through a tear or weakness in the abdominal wall, or through the inguinal canal into the scrotum.

An abdominal hernia is repaired by suturing or stapling a mesh patch over the site of the tear or weakness. The mesh patch has a rough surface that can irritate the bowel and cause adhesions. It is therefore preferred to install the patch properitoneally. It is intended that the terms properitoneal and preperitoneal be synonymous. The mesh patch is preferably attached to the properitoneal fascia of the abdominal wall, and covered by the peritoneum. To attach the mesh patch to the properitoneal fascia, the peritoneum must be dissected from the properitoneal fascia. This is a difficult process which involves the risk of puncturing the peritoneum. Moreover, strands of properitoneal fat interconnecting the peritoneum and the properitoneal fascia make it difficult to see the site of the hernia.

The use of laparoscopic techniques to perform hernia repair is becoming increasingly common. In the conventional procedure for carrying out a hernia repair laparoscopically, an endoscope and instruments are introduced into the belly through one or more incisions in the abdominal wall, and are advanced through the belly to the site of the hernia. Then, working from inside the belly, a long incision is made in the peritoneum covering the site of the hernia. Part of the peritoneum is dissected from the properitoneal fat layer to provide access to the fat layer. This is conventionally done by blunt dissection, such as by sweeping a rigid probe under the peritoneum. In this procedure, it is difficult to dissect the peritoneum cleanly since patchy layers of properitoneal fat tend to adhere to the peritoneum.

In an alternative known laparoscopic hernia repair procedure, the belly is insufflated. An incision is made in the abdominal wall close to the site of the hernia. The incision is made through the abdominal wall as far as the properitoneal fat layer. The peritoneum is then blunt dissected from the properitoneal fat layer by passing a finger or a rigid probe through the incision and sweeping the finger or rigid probe under the peritoneum. After the peritoneum is dissected from the properitoneal fat layer, the space between the peritoneum and the properitoneal fat layer is insufflated to provide a working space in which to apply the mesh patch to the properitoneal fascia.

During the blunt dissection process, it is easy to puncture through the peritoneum, which is quite thin. Additionally, after initial dissection of the properitoneal space, known surgical procedures require introduction of various instruments in the space to conduct the surgery. These instruments can cause inadvertent puncture of the peritoneum wall after the initial dissection. A puncture destroys the ability of the space between the peritoneum and the fascia to hold gas insufflation; pressurized gas can travel through a puncture in the peritoneum to allow the fluid to migrate to the abdominal cavity and degrade the pressure differential maintaining the properitoneal cavity. Also, it is difficult to dissect the peritoneum cleanly since patchy layers of properitoneal fat tend to adhere to the peritoneum. Clearing difficult adhesions can sometimes result in a breach of the peritoneum itself.

U.S. Pat. No. 5,309,896, of which this application is a Continuation-in-Part, discloses a laparoscopic hernia repair technique that enables a mesh patch to be attached to the properitoneal fascia without breaching the peritoneum. An incision is made through the abdominal wall as far as the properitoneal fat layer. A multichambered inflatable retraction device is pushed through the incision into contact with the peritoneum, and is used to separate the peritoneum from the underlying layers. The main end chamber of the inflatable retraction device is then inflated to elongate the inflatable retraction device towards the site of the hernia. As it inflates, the inflatable retraction device gently separates the peritoneum from the underlying layers. Once the main chamber of the inflatable retraction device is fully inflated, a second inflatable chamber is inflated. The second inflatable chamber enables the inflatable retraction device to continue to separate the peritoneum from the underlying layers after the main inflatable chamber has been deflated.

One or more apertures are then cut in the envelope of the main inflatable chamber to provide access to the site of the hernia for instruments passed into the main chamber. With such an arrangement, instruments pass through the main chamber situated between the peritoneum and the underlying layers. In this way, a patch can be attached to the properitoneal fascia without breaching the peritoneum.

Another device for separating tissue layers is disclosed in U.S. patent application Ser. No. 07/911,714, of which this application is a continuation-in-part. The apparatus includes a main envelope that defines a main inflatable chamber. The apparatus also includes an introducing device for introducing the main envelope in a collapsed state between the first layer of tissue and the second layer of tissue. The introducing device inflates the main envelope into an expanded state to separate the first layer of tissue from the second layer of tissue, and to create a working space between the first layer of tissue and the second layer of tissue. Finally, the apparatus includes an insufflating device for introducing insufflation gas into the working space between the first layer of tissue and the second layer of tissue.

In a method according to U.S. patent application Ser. No. 07/911,714 of separating a first layer of tissue from a second layer of tissue, a main envelope and insufflation gas are provided. The main envelope defines a main inflatable chamber. The main envelope is introduced in a collapsed state between the first layer of tissue and the second layer of tissue. The main envelope is inflated into an expanded state to separate the first layer of tissue from the second layer of tissue, and to create a working space between the first layer of tissue and the second layer of tissue. Finally, insufflation gas is introduced into the working space between the first layer of tissue and the second layer of tissue.

In a first practical embodiment of an apparatus according to U.S. patent application Ser. No. 07/911,714, the main envelope and the introducing device constitute a first component that separates the first layer of tissue from the second layer of tissue to create the working space. The insufflation device constitutes a second component, which insufflates the working space to maintain the separation of the first layer of tissue from the second. The insufflation device is tubular, has an anchor flange slidably mounted on it, and has a toroidal inflatable chamber at its distal end. The anchor flange and toroidal inflatable chamber together form a gas-tight seal with the second layer of tissue.

In a method according to U.S. patent application Ser. No. 07/911,714 of using the two-component apparatus, the introducing device is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create a working space between the two layers of tissue. An endoscope may be passed through the bore of the introducing device into the main chamber to observe the extent of separation of the layers of tissue. The main envelope is then returned to a collapsed state, and the main envelope and the introducing device are removed from the incision.

The insufflating device is inserted into the incision so that its distal end projects into the working space between the two layers of tissue. The toroidal inflatable chamber is inflated into an expanded state. The anchor flange is slid distally along the insufflating device to compress the second layer of tissue between it and the expanded toroidal inflatable chamber, and thus to form a gas-tight seal. Insufflating gas is then passed through the insufflating device into the working space to maintain the separation of the first layer of tissue from the second. An endoscope may be passed through the bore of the insufflating device into the working space to observe within the working space.

In a first embodiment of a one-component apparatus according to U.S. patent application Ser. No. 07/911,714, the introducing device is also used for returning the main envelope to a collapsed state. A single elongated tube provides the introducing device and the insufflating device. The main envelope is detachable from the single elongated tube. The single elongated tube has an anchor flange slidably mounted on it, and has a toroidal inflatable chamber at its distal end. The anchor flange and toroidal inflatable chamber together form a gas-tight seal with the second layer of tissue.

In a method according to U.S. patent application Ser. No. 07/911,714 of using the first embodiment of a one-component apparatus to separate a first layer of tissue from a second layer of tissue, the elongated tube is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create a working space between the two layers of tissue. An endoscope may be passed through the bore of the single elongated tube into the main chamber to observe the extent of separation of the layers of tissue. The main envelope is then returned to a collapsed state, detached from the elongated tube, and removed from the working space between the layers of tissue through the bore of the elongated tube.

The toroidal inflatable chamber at the distal end of the elongated tube is then inflated into an expanded state. The anchor flange is slid distally along the elongated tube to compress the second layer of tissue between it and the expanded toroidal inflatable chamber to form a gas-tight seal. Insufflating gas is passed through the elongated tube into the working space to maintain the separation of the first and second tissue layers. An endoscope may be passed through the bore of the single elongated tube into the working space to observe within the working space.

In a second embodiment of a one-component apparatus according to U.S. patent application Ser. No. 07/911,714, the introducing device is an outer elongated tube, and the insufflating device is an inner elongated tube mounted in the bore of the outer elongated tube. The proximal ends of the tubes are flexibly coupled together. The main envelope is a cylindrical piece of elastomeric material. One end of the main envelope is everted with respect to the other, and is attached to the distal end of the outer elongated tube. The other end of the main envelope is attached to the distal end of the inner elongated tube. The main inflatable chamber defined by the main envelope is thus substantially toroidal. The outer elongated tube has an anchor flange slidably mounted on it. The anchor flange and the main inflatable chamber together form a gastight seal with the second layer of tissue.

In a method according to U.S. patent application Ser. No. 07/911,714 of using the second embodiment of a one-component apparatus to separate a first layer of tissue from a second layer of tissue, the outer elongated tube is used to push the main envelope in a collapsed state through an incision through the second layer of tissue to place the main envelope between the first layer of tissue and the second layer of tissue. The main envelope is then inflated to gently separate the first layer of tissue from the second layer of tissue, and to create working a space between the layers of tissue. An endoscope may be passed through the outer elongated tube into the main chamber to observe the extent of separation of the layers of tissue.

The anchor flange is slid distally along the introducing device tube to compress the second layer of tissue between it and the main inflatable chamber, to form a gas-tight seal. Insufflating gas is then passed through the bore of the inner elongated tube and the bore of the main envelope into the working space to maintain the separation of the first layer of tissue from the second. An endoscope may be passed through the bore of the inner elongated tube and the bore of the main envelope into the working space to observe within the working space.

In a further method according to U.S. patent application Ser. No. 07/911,714, access through the abdominal wall to repair a hernia is provided. The abdominal wall includes the peritoneum and an underlying layer. A main envelope and an insufflation gas are provided. The main envelope defines a main inflatable chamber. The main envelope is introduced in a collapsed state between the peritoneum and the underlying layer. The main envelope is inflated into an expanded state to separate the peritoneum from the underlying layer, and to create a working space between the peritoneum and the underlying layer. Insufflation gas is introduced into the working space, and the hernia is repaired using an instrument passed into the working space.

In a final method according to U.S. patent application Ser. No. 07/911,714, access is provided through the abdominal wall from near the umbilicus to repair a hernia. The abdominal wall includes the peritoneum and an underlying layer. A main envelope and insufflation gas are provided. The main envelope defines a main inflatable chamber. An incision is made at the umbilicus through the abdominal wall, including the underlying layer, excluding the peritoneum. The main envelope is introduced in a collapsed state into the incision to bring the main envelope into contact with the peritoneum. The main envelope is inflated into an expanded state to separate a portion of the peritoneum from the underlying layer, and to create a space between the portion of the peritoneum and the underlying layer. The main envelope is returned to a collapsed state. The main envelope is advanced in the direction of the hernia to the boundary of the separated portion of the peritoneum. The main envelope is re-inflated into an expanded state to separate an additional portion of the peritoneum from the underlying layer, and to enlarge the space. Finally, insufflation gas is introduced into at least part of the space.

In a variation, the collapsing, advancing, and re-inflating steps are repeated with the main envelope being expanded to a partially expanded state to create a narrow tunnel between the incision at the umbilicus and the hernia. At the hernia, the main inflatable chamber is inflated into a fully expanded state to create a working space that is later insufflated.

Before being inserted into a patient, the inflatable envelopes and chambers are deflated and packed into a sheath. A known method of packing the chamber in the deflated, compact state is to roll the chamber inwardly from opposing lateral sides as shown in FIG. 18.

Referring to FIG. 34, a problem which occurs when mounting a balloon to the distal end of delivery device is that the balloon becomes skewed and off-center when inflated. The balloon becomes skewed and off-center since the balloon does not have structural support during inflation.

A method of preventing the balloon from becoming skewed and off-center during inflation is to attach the balloon away from the distal end so that a length of the cannula extends into the interior of the balloon as shown in FIG. 35. During inflation, the length of cannula inside the balloon provides structural support and prevents the balloon from becoming skewed and off-center. A problem which occurs when mounting the balloon away from the distal end of the cannula is that the visual field of an endoscope inserted in the device is limited. When dissecting and/or retracting tissue layers, it is preferable to view as much of the balloon.

SUMMARY OF THE INVENTION

The present invention solves the problems associated with known devices for separating tissue layers by providing a supporting portion movable between an extended position, in which the supporting portion is positioned within the interior of the inflatable balloon, and a retracted position, in which the supporting portion is positioned outside the interior of the inflatable balloon. The supporting portion provides support for the balloon so that the balloon does not become skewed and off-center during inflation. A delivery device preferably includes an inflation port coupled to a fluid path for inflating the balloon.

The device preferably includes an outer cannula and an inner cannula at least partially disposed within the outer cannula. The balloon is preferably mounted to the distal end of the outer cannula. The inner cannula preferably defines the supporting portion and is movably coupled to the outer cannula so that the supporting portion is movable between the extended and retracted positions with respect to the balloon.

In a first, preferred device for separating tissue layers, the inner cannula is mounted to an insert and the outer tube is mounted to the delivery device. The insert passes through a port in the delivery device and is sildably movable relative to the delivery device. The insert includes an opening adapted to receive an endoscope. The insert also preferably includes a lock for locking the endoscope to the insert. The fluid path is at least partially defined by an area between the inner and outer cannulas.

In a second, preferred device for separating tissue layers, the inner cannula is mounted to the delivery device and the outer cannula is slidably coupled to the inner cannula. First and second stops are mounted to the inner cannula to limiting slidable movement between the extended and retracted positions. A sleeve is mounted to the outer cannula. The sleeve has a detent extending inwardly toward the inner cannula. The detent is configured to matingly engage the stop to lock the inner and outer cannulas in the retracted position and extended positions, respectively. An elastomeric member is coupled to the sleeve, and forms a substantially fluid tight seal between the sleeve and the inner cannula to maintain fluid pressure in the balloon.

In a third, preferred device for separating tissue layers, the inner cannula is mounted to the delivery device and a proximal end of the outer cannula is also mounted to the delivery device. The outer cannula has a contracting portion which contracts to changing a longitudinal length of the outer cannula. The contracting portion preferably includes a number of longitudinally extending segments. At least a portion of the fluid path is housed within the inner cannula.

In a method of separating tissue layers according to the present invention, a balloon is inserted into a patient with a supporting portion extending within the interior of the balloon. The balloon is then inflated through an inflation port and a fluid path. The supporting portion provides support for the balloon during inflation so that the balloon does not become skewed and off-center. The supporting portion is then removed from the interior of the balloon so that the field of view of an endoscope inserted into the interior of the balloon is not limited.

Other features and advantages of the invention will appear from the following description in which the preferred embodiment has been set forth in detail in conjunction with the accompanying drawings.

BRIEF DESCRIPTION OF THE DRAWINGS

FIGS. 2A through 2E show a two-component apparatus according to the invention, wherein:

FIG. 2A shows the separation component of the two-component apparatus according to the invention.

FIG. 2B shows part of the distal part of the separation component of the two-component apparatus according to the invention with the main envelope in its everted position.

FIG. 2C shows part of the distal part of the separation component of the two-component apparatus according to the invention with the main envelope in its inverted position.

FIG. 2D shows the insufflation component of the two-component apparatus according to the invention with the toroidal inflatable chamber in its collapsed state.

FIG. 2E shows the insufflation component of the two-component apparatus according to the invention with the toroidal inflatable chamber in its expanded state.

FIGS. 3A through 3I are longitudinal cross sections of the abdomen illustrating the method according to the invention of using a two-component apparatus according to the invention to separate the peritoneum from the underlying layer, wherein:

FIG. 3A shows an incision made through the abdominal wall, including the properitoneal fat layer, excluding the peritoneum.

FIG. 3B shows the distal part of the separation component of a two-component apparatus according to the invention inserted into the incision. The separation component includes the main envelope in its collapsed state.

FIG. 3C shows the main envelope inflated to its expanded state to separate the peritoneum from the underlying layer.

FIG. 3D shows the main envelope returned to its collapsed state.

FIG. 3E shows the separation component removed from the incision.

FIG. 3F shows the distal part of the insufflation component of the two-component apparatus according to the invention inserted into the incision.

FIG. 3G shows the toroidal inflatable chamber of the insufflation component inflated to its expanded state and the anchor flange slid into contact with the skin of the abdominal wall to provide a gas-tight seal.

FIG. 3H shows the working space between the peritoneum and the underlying layer insufflated with a gas passed through the bore of the insufflation component.

FIG. 3I shows additional instruments passed through gas-tight trocar sheaths into the insufflated working space to repair the hernia by attaching a mesh patch to the properitoneal fascia.

FIGS. 4A through 4C show the main embodiment of the first one-component apparatus according to the invention, wherein:

FIG. 4A shows the main embodiment of the first one-component apparatus according to the invention with the main envelope in its expanded state.

FIG. 4B shows details of the area marked "A" at the distal end of the tube assembly in FIG. 4A.

FIG. 4C shows the distal part of the tube assembly with the toroidal inflatable chamber in its expanded state.

FIGS. 5A through 5D show the alternative embodiment of the first one-component apparatus according to the invention, wherein:

FIG. 5A shows the alternative embodiment of the first one-component apparatus according to the invention with the main envelope in its expanded state.

FIG. 5B shows the elongated main envelope of the alternative embodiment of the first one-component apparatus according to the invention.

FIG. 5C shows the distal part of the tube assembly of the alternative embodiment of the first one-component apparatus according to the invention with the main envelope in its everted state.

FIG. 5D shows the distal part of the tube assembly of the alternative embodiment of the first one-component apparatus according to the invention with the main envelope in its inverted state.

FIGS. 6A through 6H are longitudinal cross sections of the abdomen illustrating the method according to the invention of using a first one-component apparatus according to the invention to separate the peritoneum from the underlying layer, wherein:

FIG. 6A shows an incision made through the abdominal wall, including the underlying layer, excluding the peritoneum.

FIG. 6B shows the distal part of the tube assembly of a one-component apparatus according to the invention inserted into the incision. The tube assembly includes the main envelope in its collapsed state.

FIG. 6C shows the main envelope inflated to its expanded state to separate the peritoneum from the underlying layer.

FIG. 6D shows the main envelope returned to its fully collapsed state.

FIG. 6E shows the apparatus advanced into the incision such that the envelope of the toroidal inflatable chamber clears the incision.

FIG. 6F shows the toroidal inflatable chamber inflated to its expanded state.

FIG. 6G shows the anchor flange slid into contact with the skin of the abdominal wall. The anchor flange together with the expanded toroidal inflatable chamber provides a gas-tight seal.

FIG. 6H shows the space between the peritoneum and the underlying layer insufflated with a gas passed through the bore of the apparatus.

FIGS. 7A and 7B show a second embodiment of a one-component apparatus according to the invention, wherein:

FIG. 7A shows the second one-component apparatus according to the invention with the main envelope in its expanded state.

FIG. 7B shows the second one-component apparatus according to the invention with the main envelope in its collapsed state.

FIGS. 9A through 9F are longitudinal cross sections of the abdomen illustrating the method according to the invention of using a second one-component apparatus according to the invention to separate the peritoneum from the underlying layer, wherein:

FIG. 9A shows an incision made through the abdominal wall, including the underlying layer, excluding the peritoneum.

FIG. 9B shows the distal part of the tube assembly of a one-component apparatus according to the invention inserted into the incision. The tube assembly includes the main envelope in its collapsed state.

FIG. 9C shows the main envelope inflated to its expanded state to separate the peritoneum from the underlying layer.

FIG. 9D shows the main envelope returned to its partially-collapsed state.

FIG. 9E shows the anchor flange slid into contact with the skin of the abdominal wall. The anchor flange and the partially-collapsed main inflatable chamber together provide a gas-tight seal.

FIG. 9F shows the space between the peritoneum and the underlying layer insufflated with a gas passed through the bore of the inner tube of the apparatus.

FIGS. 10A through 10H are longitudinal cross sections of the abdomen, wherein:

FIG. 10A shows an incision made through the abdominal wall, including the underlying layer, excluding the peritoneum.

FIG. 10B shows the distal part of the apparatus according to the invention inserted into the incision. The tube assembly includes the main envelope in its collapsed state.

FIG. 10C shows the main envelope inflated to a partially-expanded state to separate part of the peritoneum from the underlying layer.

FIG. 10D shows the main envelope returned to its collapsed state.

FIG. 10E shows the apparatus advanced in the direction of the groin to bring the main envelope to the limit of the separated part of the peritoneum.

FIG. 10F shows the main envelope re-inflated to a partially-expanded state to separate an additional part of the peritoneum from the underlying layer.

FIG. 10G shows the main envelope advanced to close to the site of the hernia and re-inflated to its fully inflated state to create a working space.

FIG. 10H shows the introducer component advanced through the tunnel into the working space, and the toroidal inflatable chamber inflated to form a gas-tight seal with the entrance of the tunnel.

FIG. 10I is a plan view of the abdomen showing the insufflator component in position with its distal end in the working space and its toroidal inflatable chamber forming a gas-tight seal with the entrance of the tunnel. The figure also shows the lesser extent to which the peritoneum is detached in the tunnel compared with in the working space.

FIGS. 11A through 11C show a retraction device having a first inflatable chamber for maintaining separation between two tissue layers, wherein:

FIG. 11A shows the first inflatable chamber in a collapsed state and contained within a perforated sheath.

FIG. 11B and 11C show the first inflatable chamber in an expanded state.

FIGS. 12A and 12B show a second inflatable chamber for maintaining separation between two tissue layers, wherein:

FIG. 12A is an end view of the second inflatable chamber for maintaining separation between two tissue layers.

FIG. 12B is a side view of the second inflatable chamber in the expanded state.

FIGS. 13A through 13C show the construction of the first inflatable chamber, wherein.

FIG. 13A shows the orientation of the first and second sheets, baffles and release agent before RF welding the baffles and sheets.

FIG. 13B shows an exploded cross-sectional view of FIG. 13A with the RF welding electrodes in position.

FIG. 13C shows the baffles attached to the first and second sheets.

FIGS. 14A and 14B show a third inflatable chamber for maintaining separation between two tissue layers, wherein:

FIG. 14A is an end view of the third inflatable chamber.

FIG. 14B is a side view of the third inflatable chamber.

FIGS. 15A and 15B show a fourth inflatable chamber for maintaining separation between two tissue layers, wherein:

FIG. 15A is an end view of the fourth inflatable chamber.

FIG. 15B is a side view of the fourth inflatable chamber.

FIGS. 16A and 16B show a fifth inflatable chamber for maintaining separation between tissue layers, wherein:

FIG. 16A is an end view of the fifth inflatable chamber.

FIG. 16B is a side view of the fifth inflatable chamber.

FIG. 18 shows a balloon rolled in the known manner with two rolls formed by rolling the balloon inward from opposing outer edges;

FIG. 19 shows deployment of the balloon of FIG. 18 with the top of the rolls rubbing against the upper tissue layer;

FIG. 20 shows an isometric view of an inflatable balloon;

FIG. 21 shows a plan view of the inflatable balloon of FIG. 20;

FIG. 22 shows a first portion of the balloon of FIG. 20 displaced inwardly;

FIG. 23 shows a rolling device grasping an end of the first, inwardly-displaced portion between two rods;

FIG. 36 shows a first balloon cannula system having a delivery device, an insert and obturator;

FIG. 37 is an end view of the delivery device and insert with the insert having lips which engage recesses in the delivery device to lock the insert to the delivery device;

FIG. 38 is an end view of the insert showing the opening adapted to receive an instrument;

FIG. 39 shows the first balloon cannula system with the balloon in a deflated state;

FIG. 40 shows the first balloon cannula system with an endoscope inserted through a proximal end of the insert;

FIG. 41 shows the first balloon cannula system with the tubular insert in an extended position so that a supporting portion of an inner cannula extends into the interior of the balloon during inflation;

FIG. 42 shows the first balloon cannula system with the tubular insert in a retracted position so that the supporting portion of the inner cannula is housed within an outer cannula;

FIG. 43 shows a second balloon cannula system having an outer cannula slidably coupled to an inner cannula;

FIG. 44 shows the second balloon cannula system with a supporting portion of the inner cannula being in a retracted position;

DETAILED DESCRIPTION OF THE INVENTION

Figure 1:
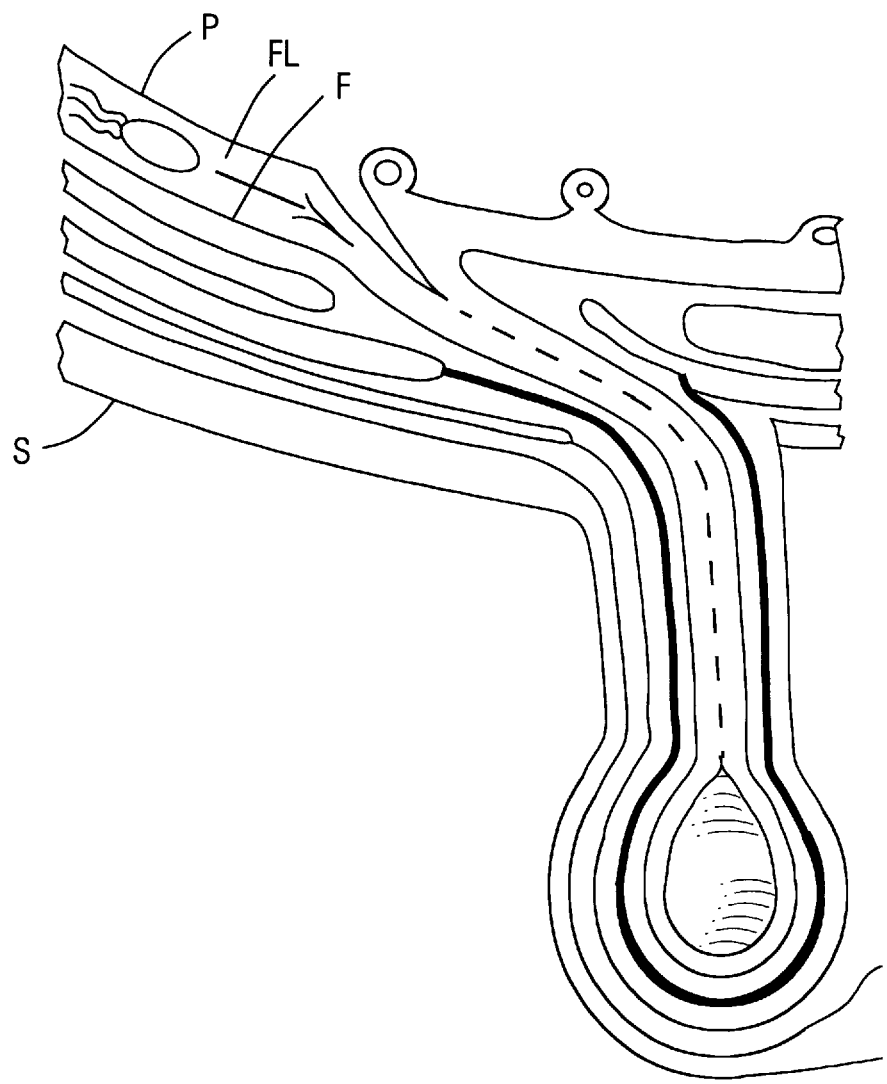
FIG. 1 is a cross-sectional view of the abdominal wall showing the peritoneum, the properitoneal fat layer, the properitoneal fascia, and other tissue layers.

A cross-sectional view of the abdominal wall is shown in FIG. 1. The abdominal wall includes the various layers of tissue shown. The peritoneum P is the innermost layer. Underlying the peritoneum are several layers of tissue, including the properitoneal fat layer FL and the properitoneal fascia F. The properitoneal fascia is the layer to which the mesh patch is preferably attached in hernia repair. The properitoneal fat layer separates the peritoneum from the properitoneal fascia. The properitoneal fat layer is relatively weak, which enables the peritoneum to be separated relatively easily from the fascia.

When the peritoneum is separated from the fascia, separation takes place at or in the properitoneal fat layer. The properitoneal fat layer can remain attached to the properitoneal fascia, or can come away with the peritoneum. Alternatively, part of the properitoneal fat layer can remain attached to the peritoneum and part of the fat layer can come away attached to the peritoneum. Because of the uncertainty in the point of separation, the layer which is detached will be called the peritoneum, and the layer from which the peritoneum is detached will be called the underlying layer. Additional layers of tissue lie between the properitoneal fascia and the skin S.

An inguinal hernia occurs when the contents of the abdominal cavity break through the abdominal wall. As described above, a hernia is repaired by attaching a piece of mesh to the abdominal wall. To prevent the mesh from causing trauma to the bowel, either through irritation of the bowel by the rough surface of the mesh, or by adhesion of the bowel to the mesh, it is preferred to attach the mesh to the properitoneal fascia. With the mesh attached to the fascia, the peritoneum covers the mesh and isolates the bowel from the mesh.

Conventional techniques of attaching the mesh patch to the properitoneal fascia, both laparoscopic and normal, involve blunt dissecting the peritoneum away from the properitoneal fascia, working from inside or outside the belly. The apparatus and methods according to the invention enable the peritoneum to be separated from the properitoneal fascia and the mesh patch attached to the fascia without entering the belly.

Although the following description will describe the apparatus and methods according to the invention with respect to hernia repair, the apparatus and methods are not restricted to hernia repair. The apparatus and methods can equally well be used in other procedures in which one layer of tissue is separated from another to form a working space between the layers. These procedures include thoracoscopy in patients with pleural adhesions; pericardioscopy, or the introduction of an endoscope into the pericardial cavity, in patients with pericardial adhesions; retroperitoneal lymph node dissection, in which the peritoneum on the distal aspect of the abdominal cavity is separated from the underlying tissue which includes lymph nodes; and in separating a blood vessel from surrounding connective tissue in the course of, for example, a femoropopliteal arterial bypass graft procedure.

1. TWO-COMPONENT APPARATUS AND METHOD OF USING

The two-component form of the apparatus according to the invention is shown in FIGS. 2A through 2C. FIG. 2A shows a partially cut-away view of the separation component 1 of the apparatus. In the separation component, the introducer tube 3 is a rigid tube having a bore with a circular cross section that can accommodate an endoscope.

The proximal end of the introducer tube is fitted with a port 5, in the proximal end 7 of which is mounted a flapper valve 2. The shutter 6 of the flapper valve is operated by the button 9. The seat 4 of the flapper valve additionally forms a gas-tight seal with an endoscope or other instrument inserted though the flapper valve into the bore of the introducer tube 3. The port 5 is also fitted with a valve 11 to which a supply of a suitable inflation fluid can be connected.

The main envelope 12 defines a main inflatable chamber 13. The main envelope is fitted to the distal end 15 of the introducer tube 3. The main envelope and main inflatable chamber are shown in their collapsed states. The dotted line 12X indicates the extent of the main envelope when the main inflatable chamber 13 in its expanded state. It should be noted that although the main envelope 12 is illustrated as generally spherical, it can be formed as oblong, "hockey puck" or disc shaped, kidney bean shaped or other shapes as are suited for the particular dissection contemplated.

The main envelope 12 is preferably formed from an elastomeric material, such as latex, silicone rubber, or polyurethane. The main envelope can also be formed from a thin, inelastic material such as Mylar®, polyethylene, nylon, etc. If an inelastic material is used, it should be suitably packaged to fit inside the bore of the introducer tube 3 when in its collapsed state.

The preferred elastomeric main envelope 12 can be simply attached to the distal end 15 of the introducer tube 3 by stretching the main envelope over the distal end of the introducer tube, as shown in FIG. 2B. The main envelope is then kept in place by friction resulting from the tension caused by stretching. A suitable adhesive, such as an epoxy or cyanoacrylate adhesive, may additionally or alternatively be used. Other means of attaching the main envelope to the inside or the outside of the introducer tube can be used.

After attachment, the main envelope 12 is inverted into the bore of the introducer tube, as shown in FIG. 2C. Inverting the main envelope into the bore of the introducer tube makes it easier to use the introducer tube to pass the main envelope through an incision and place it adjacent to the peritoneum, as will be described next.

The first part of a method according to the invention of using the separation component 1 of a two-component apparatus according to the invention to separate a first layer of tissue from a second layer of tissue will next be described. As an illustration, separating the peritoneum from the properitoneal fascia in the course of repairing a hernia will be described.

Figure 3A:
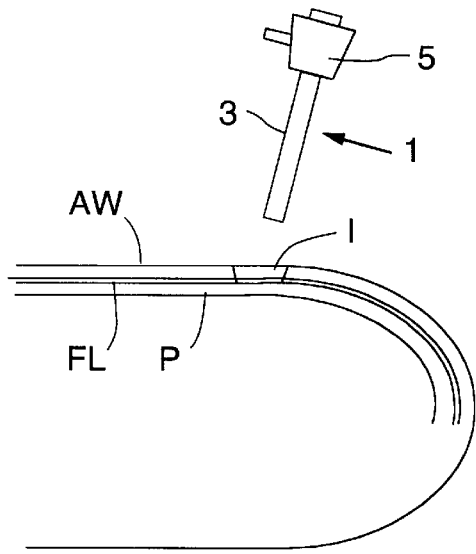
Figure 3B:
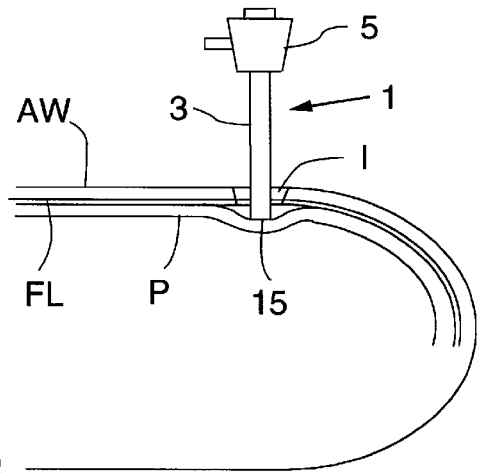

FIGS. 3A through 3H show a longitudinal cross section of the lower abdomen. An incision about 12–15 mm. long is made in the abdominal wall AW, and is carried through the abdominal wall as far as, and including, the properitoneal fat layer FL. The distal end 15 of the introducer tube 3 of the separation component 1 is then inserted into the incision to bring the distal end into contact with the peritoneum P. Additional gentle pressure detaches the part of the peritoneum in the immediate vicinity of the incision from the underlying layer, as shown in FIG. 3B. FIG. 3B shows the peritoneum detached from the properitoneal fat layer FL. The main envelope cannot be seen in these figures because it is inverted within the bore of the introducer tube 3.

A source of a suitable inflation fluid (not shown) is connected to the valve 11. A gas, preferably air, is the preferred inflation fluid, but other gases, such as carbon dioxide, can be used. A liquid, such as saline solution, can be used, but liquids are less preferable to gases because they change the optical properties of any endoscope inserted into the main inflatable chamber 13. The flow of inflation fluid is turned on, which ejects the main envelope 12 of the main inflatable chamber 13 from the bore of the introducer tube 3.

The inflation fluid progressively expands the main envelope 12, and hence the main inflatable chamber 13 defined by the main envelope, into an expanded state. The main envelope expands between the peritoneum and the properitoneal fascia, and gently and progressively detaches an increasing area of the peritoneum from the underlying layer as it expands. When the main envelope is in its expanded state, the main inflatable chamber is preferably about 4"–6" (100–150 mm) in diameter.

Figure 3C:
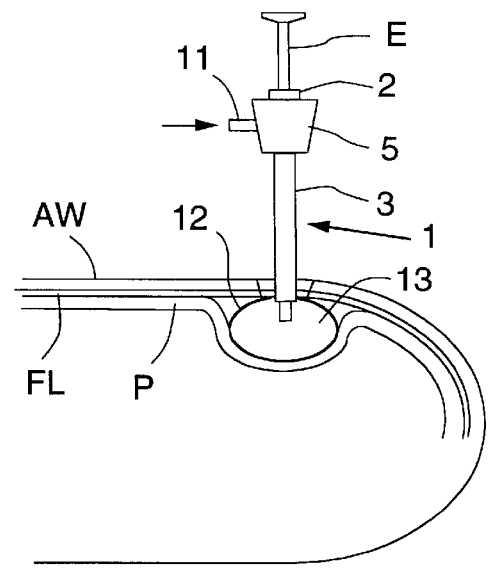

Early in the process of expanding the main envelope 12, an endoscope E is inserted into the flapper valve 2 in the port 5, as shown in FIG. 3C. The endoscope E is passed through the bore of the introducer tube 3 into the main inflatable chamber 13. Once partially expanded, the main envelope 12 is sufficiently transparent for the extent of the detachment of the peritoneum to be observed through the endoscope.

Figure 3D:
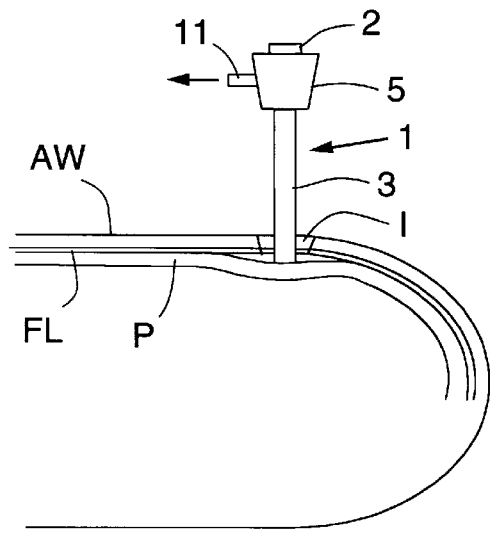
Figure 3E:
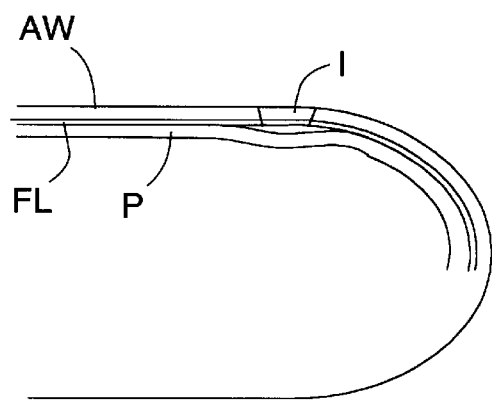

When a sufficient area of the peritoneum has been detached, the supply of inflation fluid is turned off. The inflation fluid is then vented from the main inflatable chamber, and the main envelope 12 progressively returns to its collapsed state. The peritoneum remains detached from the properitoneal fascia, however, as shown in FIG. 3D. The separation component 1, including the collapsed main envelope, is then withdrawn from the incision I (FIG. 3E).

The insufflation component 21 of the two-component apparatus, shown in FIG. 2D, will next be described. The insufflation component 21 comprises an inner tube 35 and an outer tube 37 mounted coaxially, with the outer tube covering the inner tube over most of the length of the inner tube. The inner tube is similar to the introducer tube 3 (FIG. 2A), and is a rigid tube having a bore with a circular cross section that can accommodate a 10 mm endoscope.

The proximal end of the inner tube 35 is fitted with a port 25, the proximal end 27 of which has a flapper valve 32. The shutter 36 of the flapper valve is operated by the button 29.

Additionally, the seat 34 of the flapper valve forms a gas-tight seal with an endoscope (not shown) or an obturator, such as the obturator 33, inserted though the flapper valve into the bore of the inner tube 35. The port 25 is also fitted with a first valve 31 to which a supply of a suitable insufflation fluid can be connected.

The distal end 41 of the outer tube 37 stops short of the distal end 39 of the inner tube 35. The insufflation component 21 includes a toroidal inflatable chamber 43. The envelope 45 of the toroidal inflatable chamber is a cylindrical piece of a thin elastomeric material, such as latex, silicone rubber, or polyurethane. The envelope 45 is placed over the distal ends of the inner tube and the outer tube. The proximal end 47 of the envelope is attached to the distal end 41 of the outer tube, and the distal end 49 of the envelope is attached to the distal end 39 of the inner tube 35.

The bore of the outer tube 37 is spaced from the outer surface of the inner tube 35. The annular space 51 between the inner tube and the outer tube inter connects the toroidal inflatable chamber 43 and a second valve 53. The second valve 53 is connected to a source of a suitable inflation fluid (not shown). Thus, the toroidal inflatable chamber 45 can be inflated using an inflation fluid passing into the toroidal inflatable chamber via the second valve 53 and the annular space 51. The toroidal inflatable chamber is shown in its collapsed state in FIG. 2D, and in its expanded state in FIG. 2E.

The anchor flange 55 is slidably mounted on the outer tube 37, and can be locked in a desired position along the length of the outer tube with a simple over-center action locking lever (not shown). As will be described in detail below, the anchor flange and the toroidal inflatable chamber, in its expanded condition, enable the insufflator component 21 to form a gas-tight seal to prevent insufflation gas passed through the insufflator component from escaping.

The use of the insufflation component 21 in the second part of the method according to the invention of using the two-component apparatus according to the invention will next be described. It is preferred to use the insufflation component 21 in conjunction with the first part of the method and the separation component I for dissecting the first and second tissue layers, however, the second part of the method and the insufflation component 21 may be used in conjunction with any other dissection method or apparatus including manual dissection with an endoscope, graspers, operating scope or any blunt instrument which may be used to dissect the tissue layers by sweeping the area between the layers.

Figure 3F:
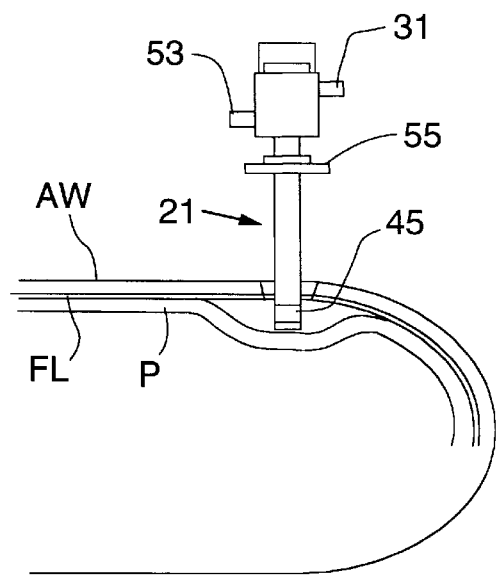

An obturator 33, having a blunt tip 59, is preferably inserted through the flapper valve 32 in the port 25 into the bore of the inner tube 35. The tip of the obturator projects beyond the distal end of the inner tube to provide the insufflation component 21 with a blunt nose. The blunt nose enables the distal end of the insufflation component to be atraumatically inserted into the properitoneal space through the incision I. The insufflation component is advanced through the incision until the proximal end of the cylindrical envelope 45 is in the properitoneal space, clear of the incision, as shown in FIG. 3F.

Figure 3G:
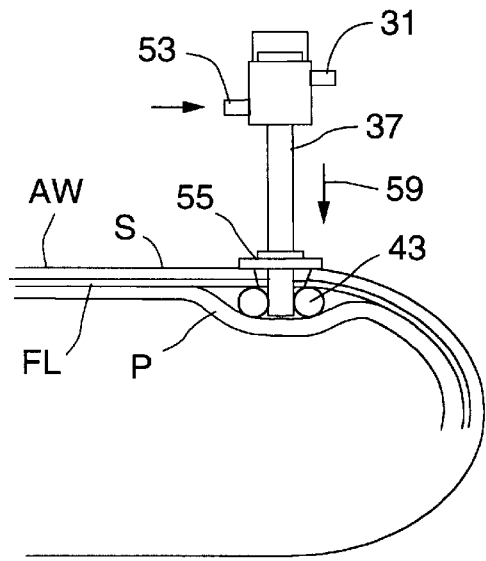

A suitable source (not shown) of an inflation fluid is attached to the second valve 53. A gas, such as air or carbon dioxide, can be used for the inflation fluid; alternatively, a liquid, such as saline can be used. Since the volume of inflation fluid required to inflate the toroidal inflatable chamber is small, about 15 ml in the preferred embodiment, the inflation fluid can be forced into the toroidal inflatable chamber from a large syringe. Inflation fluid is fed into the toroidal inflatable chamber 43 to expand the toroidal inflatable chamber to its expanded condition, as shown in FIG. 3G.

The anchor flange 55 is then advanced in the direction of the arrow 59 along the outer tube 37 to bring the anchor flange into contact with the skin S of the abdominal wall AW. The insufflation component 21 is then gripped, and the anchor flange is further advanced slightly. This forces the expanded toroidal inflatable chamber 43 into contact with the underlying layer, and slightly compresses the abdominal wall, including the underlying layer, but excluding the peritoneum P, between the toroidal inflatable chamber and the anchor flange. Once adjusted, the anchor flange is locked in position on the outer tube. The expanded toroidal inflatable chamber is held against the underlying layer, and forms a gas-tight seal between the insufflation component and the abdominal wall, including the underlying layer, excluding the peritoneum.

Figure 3H:
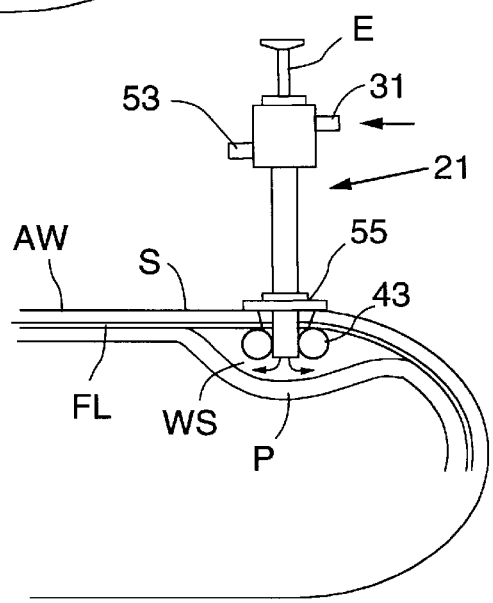

A suitable source (not shown) of an insufflation gas is attached to the first valve 31, and insufflation gas is passed through the bore of the inner tube 35 into the working WS space between the peritoneum P and the underlying layer created by separating by the peritoneum from the underlying layer using the separation component of the apparatus in the first part of the method described above. The pressure of the insufflation gas re-separates the peritoneum from the underlying layer, as shown in FIG. 3H, and provides a working space in which repair of the hernia can be carried out. The obturator is removed from the bore of the inner tube 35. The bore of the inner tube 35 can then be used to pass instruments, such as the endoscope E, into the working space to perform the repair procedure. Insufflation pressure is maintained by the flapper valve 32.

Figure 3I:
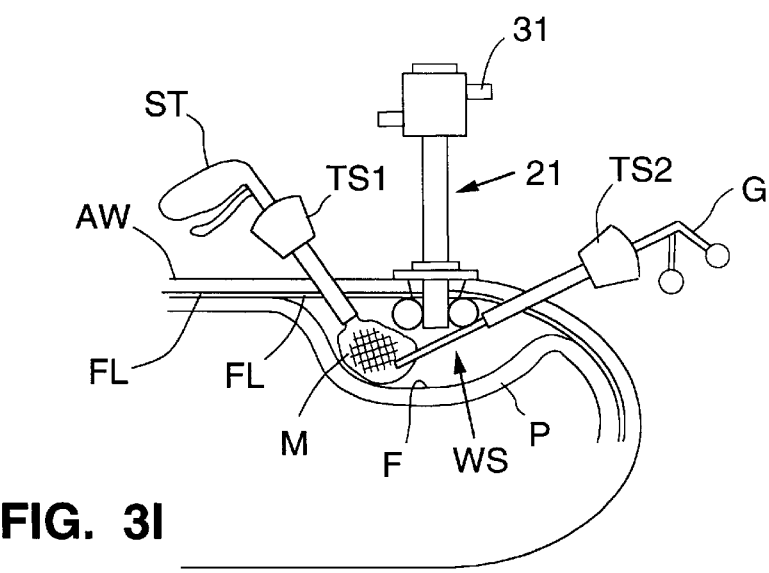

As part of the hernia repair procedure, additional gas-tight trocar sheaths are inserted through the abdominal wall into the working space WS, shown in FIG. 3I. An endoscope (not shown) can be passed into the working space through the bore of the inner tube 35, or through one of the additional trocar sleeves for observation. If the properitoneal fat layer FL remains attached to the properitoneal fascia F, it is scraped off the fascia around the site of the hernia so that the patch can be attached directly to the fascia.

A patch M, preferably a Dacron® or Teflon® mesh, is shown gripped by the grippers G, and passed through the trocar sleeve TS2 into the working space. Using the grippers, the patch is manipulated to place it in contact with the properitoneal fascia F over the site of the hernia. The patch is attached to the properitoneal fascia by staples inserted using the stapler ST passed through the trocar sleeve TS1 into the working space. Sutures can alternatively be used to attach the patch to the properitoneal fascia.

After the treatment procedure is completed, the first valve 31 is operated to release the insufflation gas from the working space. The second valve 53 is operated to release the inflation fluid from the toroidal inflatable chamber 43. The envelope 45 of the toroidal inflatable chamber returns to its collapsed state, flush with the outer surfaces of the inner tube and the outer tube. The insufflating component is then withdrawn from the incision, and the incision is closed using sutures or clips. The pressure of the viscera against the peritoneum returns the peritoneum into contact with the underlying layer. Over time, the peritoneum reattaches to the underlying layer.

2. FIRST ONE-COMPONENT APPARATUS (a) Main Embodiment

The separation component can be dispensed with, and the insufflation component can be modified to provide the first embodiment of a one component apparatus according to the invention. The first one-component apparatus is shown in FIG. 4A. The first one-component apparatus 121 is similar to the insufflation component just described. Like components will use the same reference numbers with 100 added. The first one component apparatus comprises a tube assembly 160, including an inner tube 135 coaxially mounted inside an outer tube 137. The outer tube covers the inner tube over most of the length of the inner tube. The inner tube is a rigid tube having a bore with a circular cross section that can accommodate an endoscope (not shown).

The proximal end of the inner tube 135 is fitted with a port 125, the proximal end 127 of which includes a flapper valve 132. The shutter 136 of the flapper valve is operated by the button 129. Additionally, the seat 134 of the flapper valve forms a gas-tight seal with an endoscope (not shown), or other instrument, inserted though the flapper valve into the bore of the inner tube 135. The port 125 is also fitted with a first valve 131 to which a supply of a suitable insufflation fluid can be connected.

Unlike the insufflator component of the two-component apparatus, the distal end 141 of the outer tube 137 extends as far as the distal end 139 of the inner tube 135. The tubes are connected together over a distal portion 167 of their lengths (see detail in FIG. 4B). A circumferential groove 169 is formed in the inner wall of the distal portion 167. A groove with a wedge-shaped cross section is shown. The circumferential groove can have other cross sections, such as square, or semi-circular. The circumferential groove retains the main envelope 112, which defines the main inflatable chamber 113, in the bore of the inner tube, as will be described in more detail below.

The envelope 145 of the toroidal inflatable chamber 143 covers the distal part of the tube assembly 160. The envelope 145 is a cylindrical piece of a thin elastomeric material, such a latex, silicone rubber, or polyurethane. The proximal end 147 and the distal end 149 of the envelope are attached to the outer surface 163 of the tube assembly using a circumferential line of adhesive applied at each end of the envelope. An epoxy or cyanoacrylate adhesive is preferably used. When the toroidal inflatable chamber is in its collapsed state, the envelope 145 lies almost flush with the outer surface of the tube assembly 160.

The outer tube 137 is spaced from the inner tube 135 over at least part of its circumference. The space 151 between the inner tube and the outer tube, and a radial passage 161 through the wall of the outer tube interconnect the toroidal inflatable chamber 143 and the second valve 153. The second valve 153 is connected to a source of a suitable inflation fluid (not shown). The toroidal inflatable chamber is shown in its collapsed state in FIGS. 4A and 4B, and in its expanded state in FIG. 4C.

The anchor flange 155 is slidably mounted on the tube assembly 160, and can be locked in a desired position along the length of the tube assembly with a simple over-center action locking lever (not shown). As will be described in detail below, the anchor flange and the toroidal inflatable chamber, in its expanded condition, form a gas-tight seal to prevent insufflation gas from escaping.

The first one-component apparatus also includes a main envelope 112 detachably attached to the bore of the inner tube 135. The main envelope defines the main inflatable chamber 113. The main envelope is preferably formed of an elastomeric material such as latex, silicone rubber, or polyurethane. The main envelope can also be formed from a thin, inelastic material such as Mylar®, polyethylene, nylon, etc. If an inelastic material is used, it should be suitably packaged to fit inside the bore of the inner tube when in its collapsed state.

The main envelope 112 is formed such that it has a substantially spherical shape when it is in its expanded state, and is also formed with a neck 165. The neck has an outside diameter substantially equal to the diameter of the bore of the inner tube 135. The neck 165 can be rolled outwards a number of times, as in the neck of a common toy balloon, or the neck can be attached to a suitable O-ring 171, as shown in FIG. 4B. The rolled neck, or the O-ring attached to the neck, engages with the circumferential groove 169 in the inner wall in the inner tube to attach the main envelope 112 to the inner tube. The main envelope is housed in the bore of the inner tube when the main inflatable chamber is in its collapsed state.

The rip cord 173 is attached to the neck 165 of the main envelope 112, runs proximally up the bore of the inner tube 135, and emerges from the port 125 through the flapper valve 132. The part of the rip cord 173 emerging from the flapper valve can be gripped and pulled in a proximal direction to release the rolled neck 165 or the O-ring 171 from the circumferential groove 169. By pulling further on the rip cord, the entire main envelope can be pulled proximally through the bore of the inner tube.

(b) Alternative Embodiment

Figure 5A:
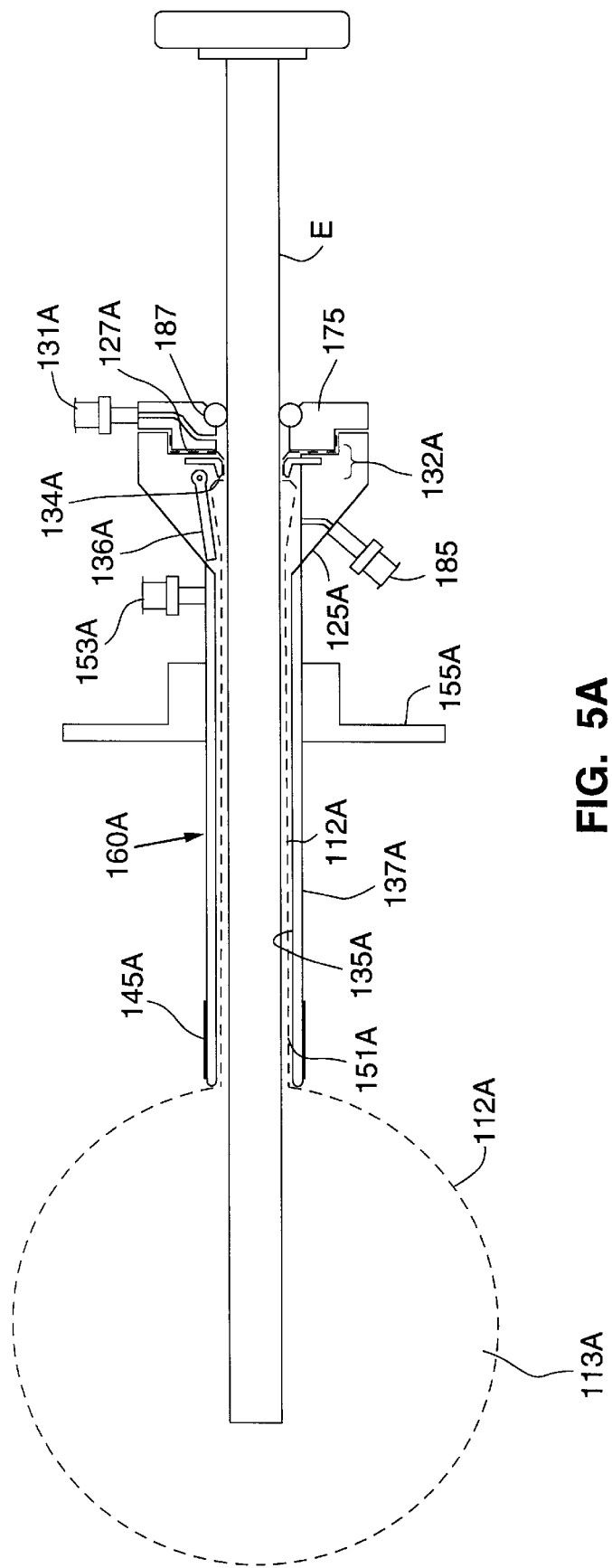

An alternative embodiment of the first one-component apparatus having an elongated main envelope 112A is shown in FIG. 5A. The tube assembly 160A includes the inner tube 135A mounted coaxially inside the outer tube 137A, with the proximal and distal ends of the tubes interconnected. The space 151A between the inner tube and the outer tube communicates with the toroidal inflatable chamber through the radial passage 161A in the wall of the outer tube. The space between the inner tube and the outer tube also communicates with the toroidal chamber inflation valve 153A.

The bore of the inner tube 135A communicates with the port 125A, fitted with the insufflation valve 185. The port 125A is also fitted with a flapper valve 132A, including the flapper valve seat 134A, which maintains gas pressure when the apparatus is used for insufflation. The flapper valve seat 134A also provides a gas-tight seal around any instrument, such as the endoscope E, passed through the flapper valve.

Figure 5B:
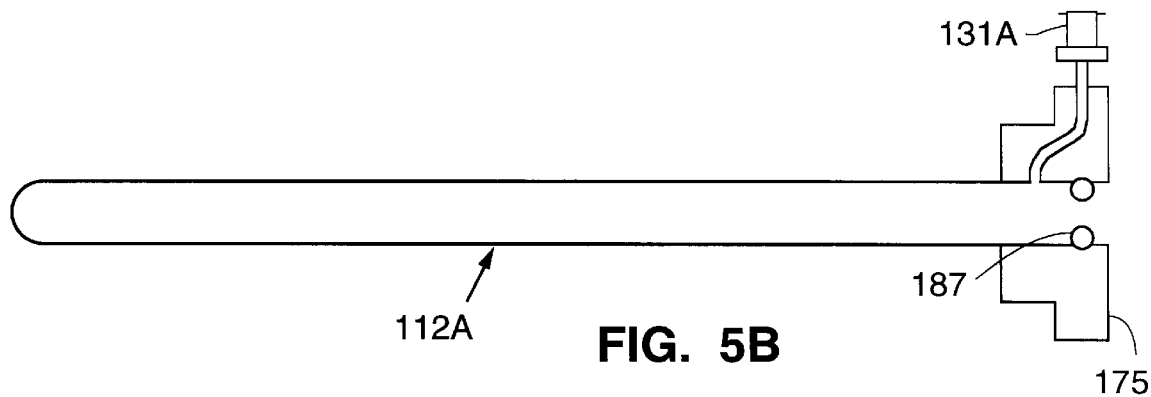

The elongated main envelope 112A is shown in FIG. 5B. The main envelope is an elongated cylinder with a closed distal end 177. The main envelope is preferably formed from an elastomeric material, such as latex, silicon rubber, or polyurethane. Attached to the proximal end of the main envelope is a manifold 175 which mates with the proximal face 127A of the port 125A. The manifold 175 is fitted with an O-ring seal 187, which forms a gas-tight seal with any instrument passed through it. The manifold 175 is also fitted with the main chamber inflation valve 131A to which a supply (not shown) of a suitable inflation fluid can be attached to inflate the main inflatable chamber 112A.

Figure 5C:
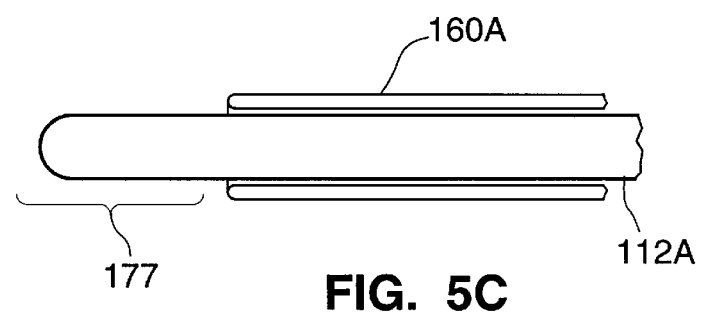
Figure 5D:
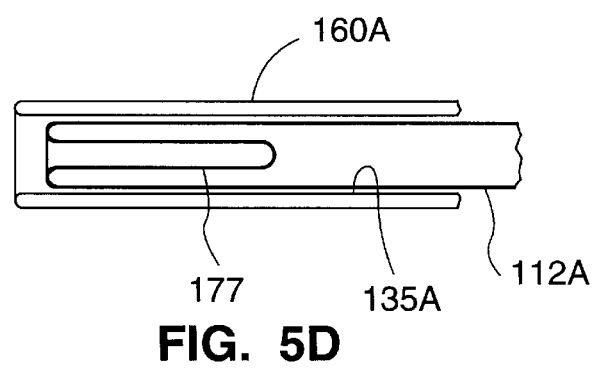

The elongated main envelope 112A is passed through the flapper valve 132A into the bore of the inner tube 135A. The manifold 175 is engaged with the proximal face 127A of the port 125A. When the manifold is engaged, the distal end 177 of the main envelope projects beyond the distal end of the tube assembly 160A, as shown in FIG. 5C. The distal end of the main envelope is then inverted int 135A, as shown in FIG. 5D.

An endoscope, or some other suitable instrument, is inserted through the O-ring seal 187 to seal the manifold before inflation fluid is passed through the main chamber inflation valve 131A to inflate the main inflatable chamber 113A.

Alternatively, the seal 187 can be replaced by an additional flapper valve (not shown) so that the main inflatable chamber can be inflated without the need to use an instrument to seal the manifold.

When inflation fluid is passed into the main inflatable chamber 113A through the valve 131A, the distal end 177 of the main envelope 112A is ejected from the inner tube 135A. The inflation fluid then progressively expands the main envelope 112A, and hence the main inflatable chamber 113A defined by the main envelope, into an expanded state, as shown in FIG. 5A. The part of the main envelope inside the inner tube is subject to the same inflation pressure as the distal end 177 of the main envelope, but is constrained by the inner tube and so does not inflate.

After using the main envelope 112A to separate the peritoneum away from the underlying layer, as will be described in detail below, the inflation pressure fluid is vented from the main inflatable chamber 113A, and the main envelope returns to its collapsed state. When the main envelope is in its collapsed state, it can move freely in the bore of the inner tube 135. The main envelope is removed from the inner tube by disengaging the manifold 175 from the proximal face 127A of the port 125A, and using the manifold 175 to pull the main envelope proximally through the bore of the inner tube.

Inflation fluid for the toroidal inflatable chamber the envelope of which 145A is shown in FIG. 5A, is passed through the toroidal chamber inflation valve 153A. Insufflation gas is passed through the insufflation valve 185.

The toroidal inflatable chamber and the anchor flange 155A of the alternative embodiment of the first one-component apparatus are the same as in the main embodiment, and will therefore not be described.

(c) Method of Using the First One-Component Apparatus (Both Forms)

The method according to the invention of using either form of the first one-component apparatus according to the invention to separate a first layer of tissue from a second layer of tissue will next be described. As an illustration, separating the peritoneum from the properitoneal fascia in the course of repairing a hernia will be described.

Figure 6A:
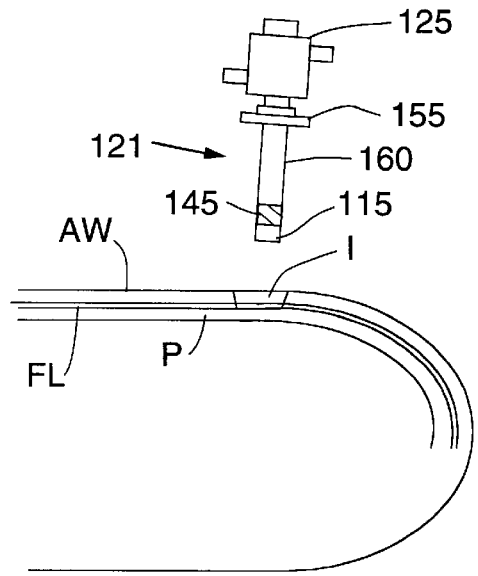
Figure 6B:
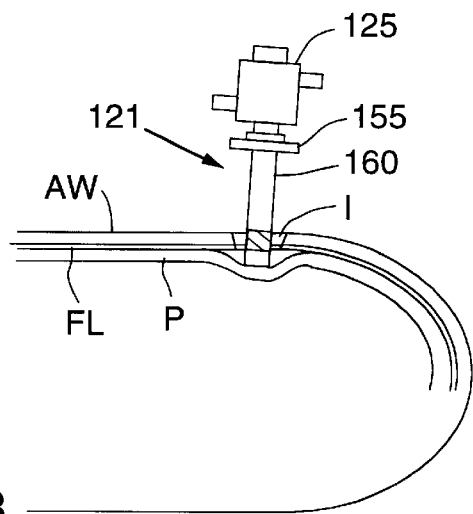

FIGS. 6A through 6H show a longitudinal cross section of the lower abdomen. An incision about 12–15 mm. long is made in the abdominal wall AW, and carried through the abdominal wall as far as, and including the properitoneal fat layer FL, as shown in FIG. 6A. The distal end 115 of the tube assembly 160 of the one-component apparatus 121 is then inserted into the incision to bring the distal end into contact with the peritoneum. Additional gentle pressure detaches the part of the peritoneum in the immediate vicinity of the incision from the underlying layer, as shown in FIG. 6B. FIG. 6B shows the peritoneum detached from the properitoneal fat layer FL. The main envelope cannot be seen in these figures because it is inverted within the bore of the tube assembly.

A source of inflation fluid (not shown) is connected to the valve 131. A gas, preferably air, is the preferred inflation fluid, but other gases, such a carbon dioxide can be used. A liquid, such as saline solution can be used, but liquids are less preferable to gases because they change the optical properties of any endoscope inserted into the main inflatable chamber 113. The flow of inflation fluid is turned on, which ejects the main envelope 112 from the bore of the tube assembly 160.

The inflation fluid progressively expands the main envelope 112, and hence the main inflatable chamber 113 defined by the main envelope, into an expanded state. The main envelope expands between the peritoneum P and the properitoneal fat layer FL, and gently and progressively detaches an increasing area of the peritoneum from the underlying layer as it expands. When the main envelope is in its expanded state, the main inflatable chamber is preferably about 4"–6" (100–150 mm) in diameter.

Figure 6C:
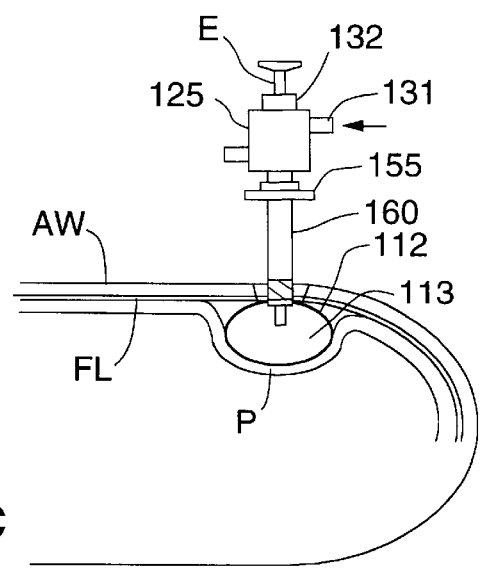

Early in the process of expanding the main envelope 112, an endoscope E is inserted into the flapper valve 132 in the port 125, as shown in FIG. 6C. The endoscope E is passed through the bore of the tube assembly 160 into the main inflatable chamber 113. Once the main envelope is partially expanded, the main envelope is sufficiently transparent for the extent of the detachment of the peritoneum to be observed using the endoscope.

Figure 6D:
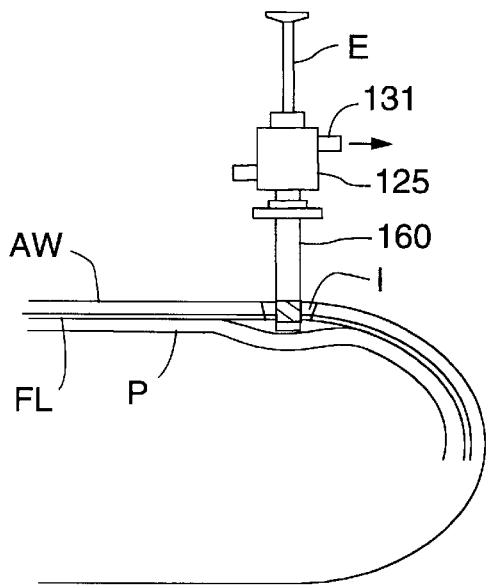

When a sufficient area of the peritoneum is detached, the supply of inflation fluid is turned off. The inflation fluid is then vented from the main inflatable chamber 113, and the main envelope progressively returns to its collapsed state. The peritoneum remains detached from the underlying layer, however, as shown in FIG. 6D. The main envelope is then removed from the bore of the tube assembly 160. The different methods of removing the main envelope from the bore of the tube assembly for the two different forms of the first one-component apparatus are described above.

Figure 6E:
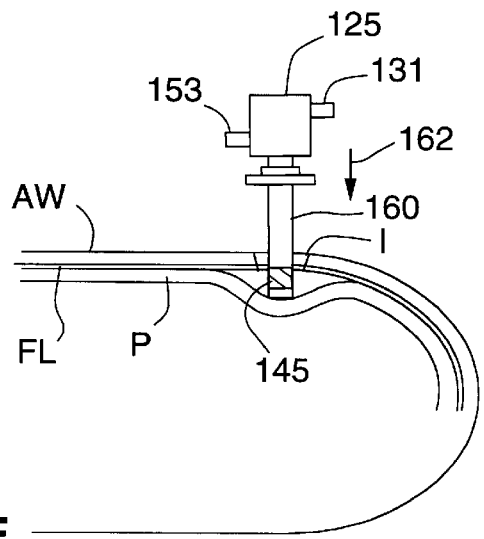

After the main envelope 112 has been removed from the bore of the tube assembly, the tube assembly is advanced into the incision in the direction of the arrow 162 until the proximal end of the envelope 145 of the toroidal inflatable chamber is in the properitoneal space, clear of the incision, as shown in FIG. 6E.

Figure 6F:
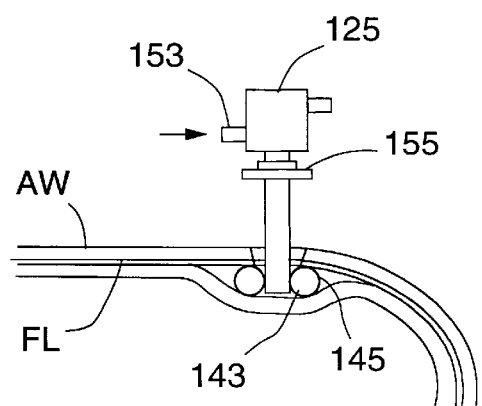

A suitable source (not shown) of an inflation fluid is attached to the valve 153. A gas, such as air or carbon dioxide, can be used for the inflation fluid; alternatively, a liquid, such as saline can be used. Since the volume of inflation fluid required to inflate the toroidal inflatable chamber is small, about 15 ml in the preferred embodiment, the inflation fluid can be contained in a large syringe. Inflation fluid is fed into the toroidal inflatable chamber 43 to expand the toroidal inflatable chamber to its expanded condition, as shown in FIG. 6F.

Figure 6G:
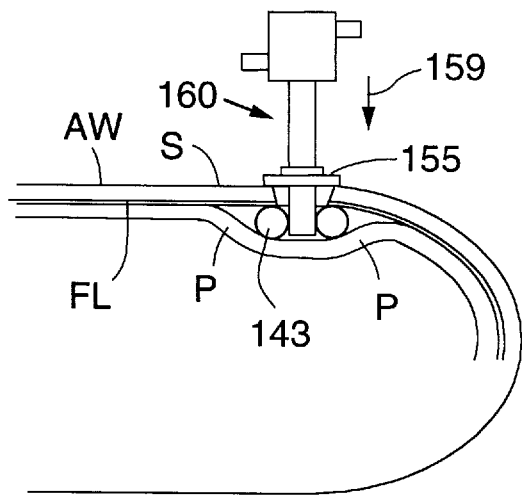

The anchor flange 155 is then advanced in the direction of the arrow 159 along the tube assembly 160 to bring the anchor flange into contact with the skin S of the abdominal wall AW. The tube assembly 160 is then gripped, and the anchor flange is further advanced slightly. This forces the expanded toroidal inflatable chamber 143 into contact with the underlying layer, and slightly compresses the abdominal wall AW, including the underlying layer but excluding the peritoneum P, between the expanded toroidal inflatable chamber and the anchor flange, as shown in FIG. 6G. Once adjusted, the anchor flange is locked in position on the tube assembly. The expanded toroidal inflatable chamber is held against the underlying layer and forms a gas-tight seal with the abdominal wall, excluding the peritoneum.

Figure 6H:
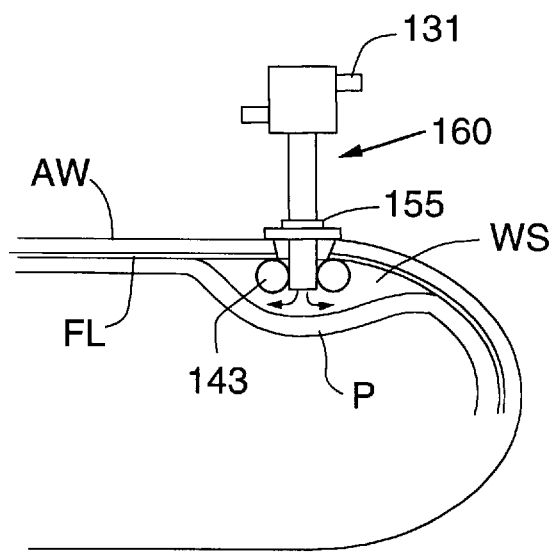

A suitable source (not shown) of an insufflation gas is attached to the first valve 131, and insufflation gas is passed through the bore of the inner tube 135 into the working space WS between the peritoneum P and the underlying layer created by separating the peritoneum from the underlying layer. The pressure of the insufflation gas re-separates the peritoneum from the underlying layer, as shown in FIG. 6H, and provides a working space in which repair of the hernia can be carried out. The bore of the tube assembly 160 can be used to pass instruments, such as the endoscope E, into the working space to perform the repair procedure. When no instrument is inserted into the bore of the tube assembly, insufflation pressure is maintained by the flapper valve.

As part of the hernia repair procedure, additional gas-tight trocar sleeves (not shown) are inserted through the abdominal wall into the working space. The same procedure as described above in connection with FIG. 31 is used to attach a mesh patch to the properitoneal fascia over the site of the hernia. The process can be observed with the aid of an endoscope (not shown) passed through the bore of the tube assembly 160, or through one of the additional trocar sleeves.

After the treatment procedure is completed, the valve 131 is operated to release the insufflation gas from the working space WS. The valve 153 is operated to release the inflation fluid from the toroidal inflatable chamber 143, which releases compression of the abdominal wall AW, excluding the peritoneum. The toroidal inflatable chamber returns to its collapsed state, with its envelope 145 flush with the outer surface the tube assembly 160. The tube assembly is then withdrawn from the incision, and the incision is closed using sutures or clips. The pressure of the viscera against the peritoneum returns the peritoneum into contact with the underlying layer. Over time, the peritoneum reattaches to the underlying layer.

3. SECOND ONE-COMPONENT APPARATUS (a) Second One-Component Apparatus

A second embodiment of a one-component apparatus is shown in FIGS. 7A and 7B. The second one-component apparatus 121 is similar to the first one-component apparatus just described. However, the second one-component apparatus has a substantially spherical toroidal main inflatable chamber, that avoids the need to detach and remove the main envelope at the end of the separation process. Also, in the second one-component apparatus, a single toroidal main inflatable chamber provides the separating function of the main inflatable chamber and the sealing function of the toroidal inflatable chamber of the first one-component apparatus.

In the following description, similar components will use the same reference numbers with an additional 100 added.

The second one-component apparatus comprises a tube assembly 260, including an outer tube 237 to which is attached a twin port assembly 224 is attached. The port assembly includes a first port 226 and a second port 228. The first port is provided with a first flapper valve 202, including the flapper valve seat 204. The second port is provided with a second flapper valve 206, including the flapper valve seat 208. Each flapper valve seat additionally forms a gas-tight seal with an instrument passed through it.

The tube assembly 260 also includes the inner tube 235. The inner tube has a length that is shorter than the length of the outer tube 237. The proximal end 210 of the inner tube is flexibly attached to the proximal end 222 of the outer tube 237 and to the first port 226. The flexible attachment enables the distal end 214 of the inner tube to move in the direction shown by the arrow 216. The first port communicates with the bore of the inner tube 235, and the second port communicates with the bore of the outer tube 237.

The insufflation valve 285 communicates with the first port 226, and the bore of the inner tube 235. The main chamber inflation valve 231 communicates with the second port 228, and the bore of the outer tube 237.

The main envelope 212 defines the main inflatable chamber 213 and comprises a cylindrical piece of an elastomeric material such a latex, silicone rubber, or polyurethane. The apparatus is shown with its main envelope in its collapsed state in FIG. 7B, in which the structure of the main envelope can also be seen. The main envelope preferably has a diameter smaller than the outside diameter of the inner tube.

One end 230 of the main envelope is attached to the distal end 214 of the inner tube 235 by means of a suitable adhesive, such as an epoxy or cyanoacrylate adhesive. The other end 232 of the main envelope is everted (i.e., turned back on itself to bring the inside surface 234 of the main envelope to the outside) and attached to the distal end 236 of the outer tube using the same type of adhesive. The main envelope is preferably attached to the outer surfaces of the inner tube and the outer tube.

The apparatus is shown with the main envelope 212 in its expanded state in FIG. 7A. A suitable source of inflation gas is connected to the valve 231 and flows into the main inflatable chamber through the bore of the outer tube 237. The pressure acting on the surface 238 of the main envelope 212 causes the main envelope to assume the toroidal shape shown in FIG. 7A to define the toroidal main chamber 213. FIGS. 7A and 7B show the correspondence between the surfaces 234 and 238 of the main envelope when the main envelope is in its collapsed state (FIG. 7B) and in its expanded state (FIG. 7A).

The anchor flange 255 is slidably mounted on the tube assembly 260, and can be locked in a desired position along the length of the tube assembly. The anchor flange 255 is similar to the anchor flange 55 (FIG. 2A) and so will not be described further.

Figure 8A:
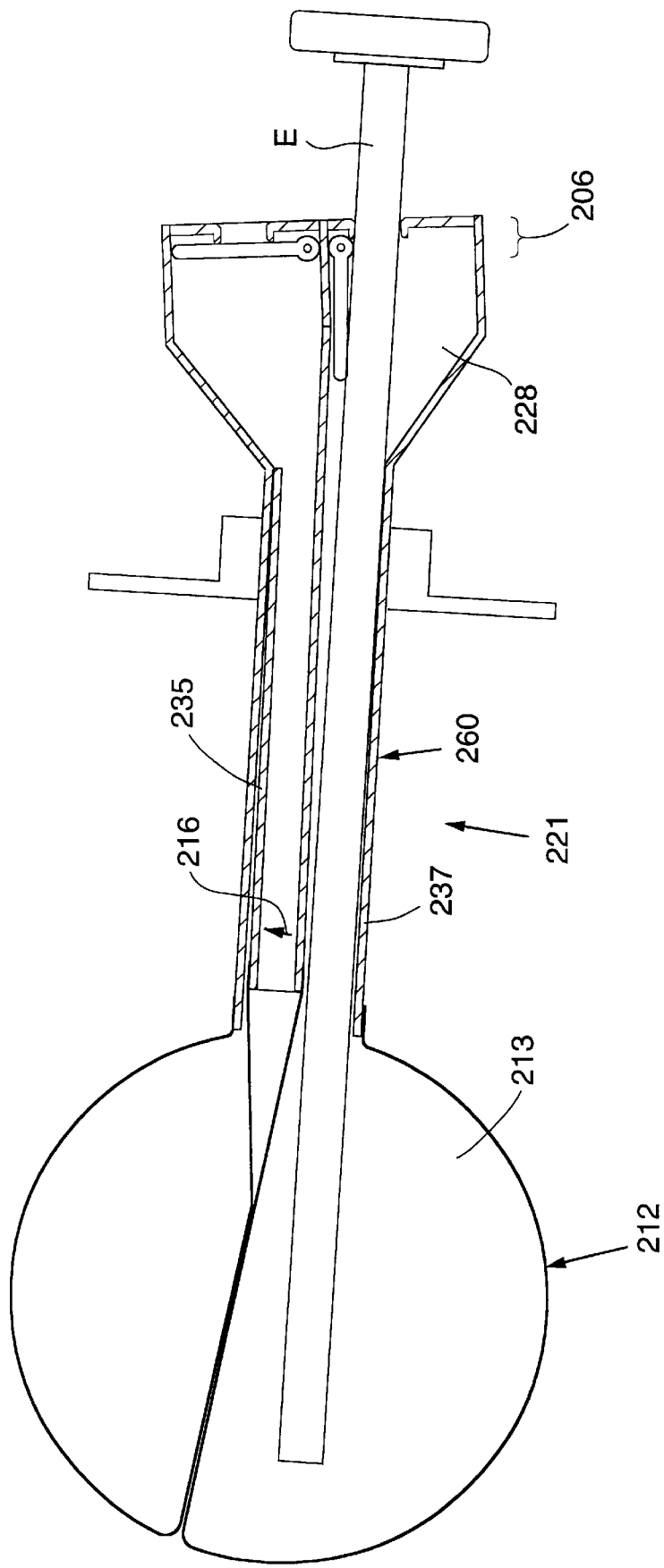
FIG. 8A shows the second one-component apparatus according to the invention with the main envelope in its expanded state and an endoscope passed through the bore of the outer tube into the main inflatable chamber.

In FIG. 8A, an endoscope E is shown passed through the second flapper valve 206, the second port 228, and the bore of the outer tube 237 into the main inflatable chamber 213. The flexible mounting of the inner tube 235 in the outer tube enables the endoscope to displace the inner tube 235 in direction of the arrow 216 to gain access to the main inflatable chamber. The endoscope is inserted through the second port into the main inflatable chamber during the separation phase of using the apparatus to observe the extent of the separation of tissue.

Figure 8B:
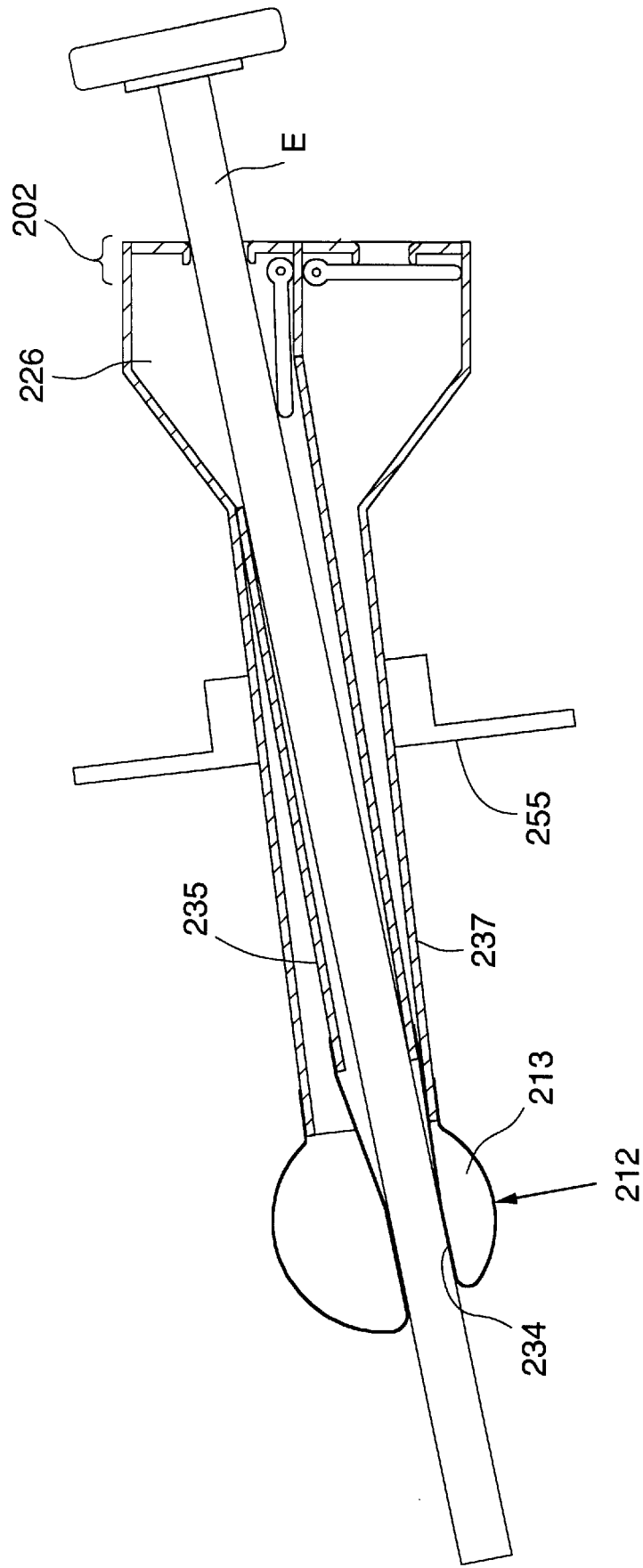
FIG. 8B shows the second one-component apparatus according to the invention with the main inflatable chamber in its partially expanded state and an endoscope passed through the bore of the inner tube and through the bore of the main envelope.

In FIG. 8B, an endoscope E is shown passed through the first flapper valve 202, the first port 226, the bore of the inner tube 235, and the bore 234 of the main envelope 212. The distal part of the endoscope emerges from the bore of the main envelope, and can be advanced beyond the main inflatable chamber 213 to observe the site of the hernia more closely. The endoscope is inserted through the first port, the inner tube, and the bore of the main envelope during the insufflation phase of using the apparatus. Instruments other than endoscopes can also be passed to the site of the hernia through the first flapper valve, the first port, the inner tube, and the bore of the main envelope if desired.

Also in FIG. 8B, the main envelope 212 is shown in the partially collapsed state that it preferably assumes during the insufflation phase of the procedure. In this part of the procedure, the partially collapsed main inflatable chamber and the anchor flange 255 together provide a gas-tight seal to prevent the leakage of insufflation gas. Alternatively, this part of the procedure can be carried out with the main inflatable chamber in a fully expanded state.

(b) Method of Using the Second One-Component Apparatus

The method according to the invention of using the second embodiment of the one-component apparatus according to the invention to separate a first layer of tissue from a second layer of tissue will next be described. As an illustration, separating the peritoneum from the properitoneal fascia in the course of repairing a hernia will be described.

Figure 9A:
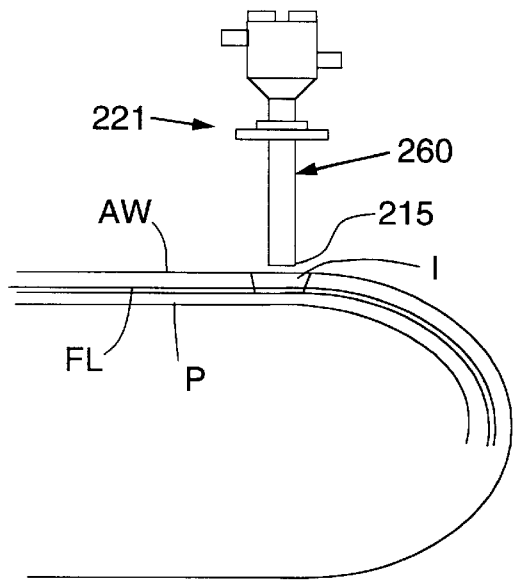
Figure 9B:
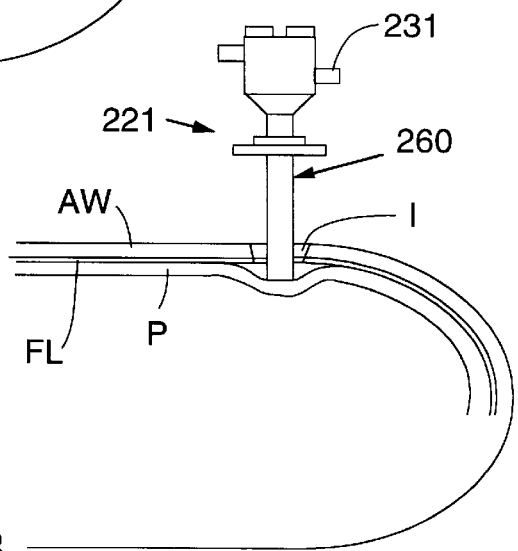

FIGS. 9A through 9F show a longitudinal cross section of the lower abdomen. An incision about 12–15 mm long is made in the abdominal wall AW, and carried through the abdominal wall as far as, and including, the properitoneal fat layer FL, as shown in FIG. 9A. The distal end 215 of the tube assembly 260 of the second one-component apparatus 221 is then inserted into the incision to bring the distal end into contact with the peritoneum P. Additional gentle pressure detaches the part of the peritoneum in the immediate vicinity of the incision from the underlying layer, as shown in FIG. 9B. FIG. 9B shows the peritoneum detached from the properitoneal fat layer FL. The main envelope cannot be seen in these figures because it is inverted within t he bore of the tube assembly.

A source of inflation fluid (not shown) is connected to the valve 231. A gas, preferably air, is the preferred inflation fluid, but other gases, such a carbon dioxide can be used. A liquid, such as saline solution can be used, but liquids are less preferable to gases because they change the optical properties of any endoscope inserted into the main inflatable chamber. The flow of inflation fluid is turned on, which ejects the main envelope 212 from the bore of the tube assembly 260.

The inflation fluid progressively expands the main envelope 212, and hence the main inflatable chamber 213 defined by the main envelope, into a n expanded state. The main envelope expands between the peritoneum P and the properitoneal fat layer FL, and gently and progressively separates an increasing area of the peritoneum from the underlying layer as it expands. When the main envelope is in its expanded state, the main inflatable chamber is preferably about 4"–6" (100–150 mm) in diameter.

Figure 9C:
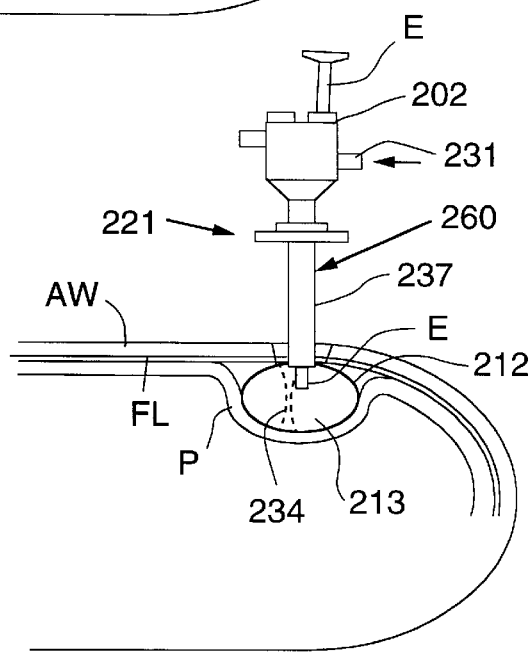

Early in the process of expanding the main envelope 212, an endoscope E is inserted into the first flapper valve 202, as shown in FIG. 9C. The endoscope E is passed through the bore of the outer tube 237 into the main inflatable chamber 213. Once partially expanded, the main envelope 212 is sufficiently transparent for the extent of the separation of the peritoneum to be observed using the endoscope.

Figure 9D:
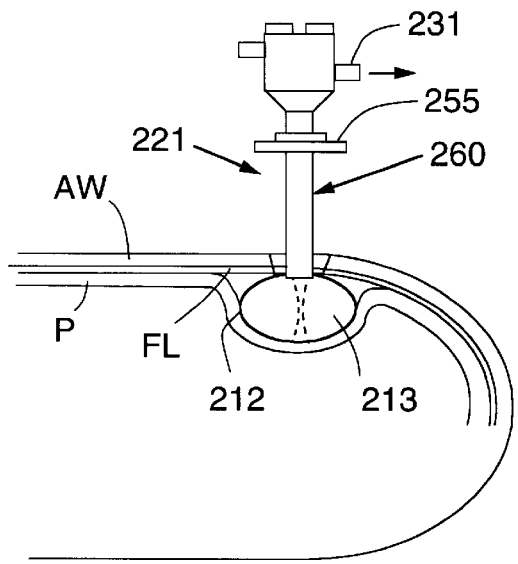

When a sufficient area of the peritoneum is separated, the supply of inflation fluid is turned off. The endoscope E is removed from the main inflatable chamber 213. The valve 231 is then opened to allow inflation fluid to vent partially from the main inflatable chamber 213. The main envelope 212 progressively returns part-way towards its collapsed state, as shown in FIG. 9D. Alternatively, the main envelope may be kept fully expanded.

Figure 9E:
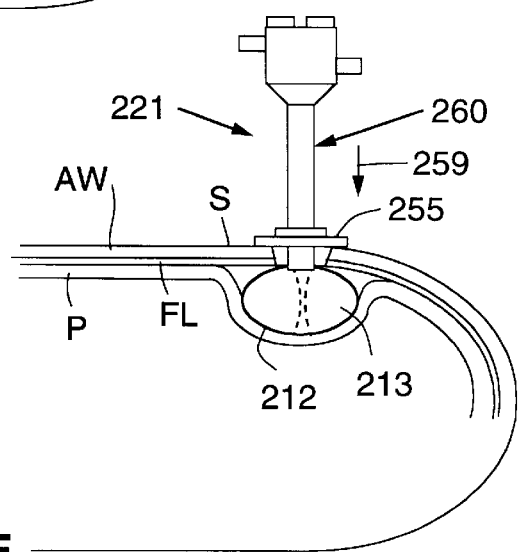

The anchor flange 255 is then advanced in the direction of the arrow 259 along the tube assembly 260 to bring the anchor flange into contact with the skin S of the abdominal wall AW. The tube assembly 260 is then gripped, and the anchor flange is further advanced slightly. This forces the main inflatable chamber 213 into contact with the underlying layer, and slightly compresses the abdominal wall, including the underlying layer but excluding the peritoneum, between the main inflatable chamber and the anchor flange, as shown in FIG. 9E. Once adjusted, the anchor flange is locked in position on the tube assembly. The main inflatable chamber is held against the underlying layer and forms a gas-tight seal with the abdominal wall, excluding the peritoneum.

Figure 9F:
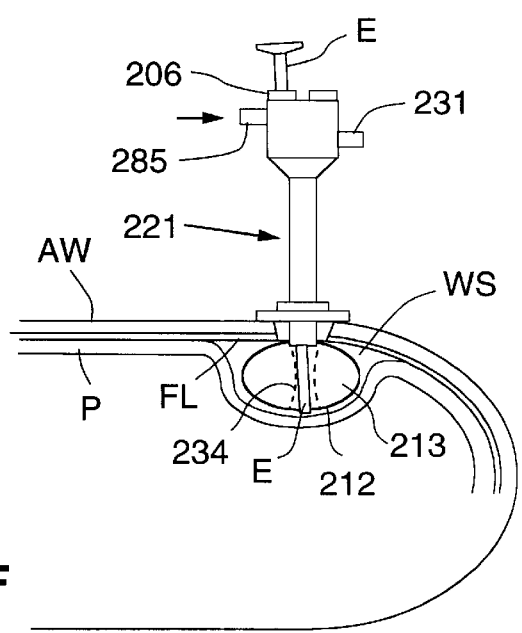

A suitable source (not shown) of insufflation gas is attached to the second valve 285, and insufflation gas is passed through the bore of the inner tube 235, and the bore 234 of the main envelope, into the working space WS between the peritoneum P and the underlying layer. The pressure of the insufflation gas re-separates the peritoneum from the underlying layer, as shown in FIG. 9F, and provides a working space in which repair of the hernia can be carried out.

Instruments, such as the endoscope E, can be passed through the second flapper valve 206, the bore of the inner tube 235, and the bore 234 of the main envelope, as shown in FIG. 8B, into the working space to perform the repair procedure. When no instrument is inserted into the bore of the inner tube, insufflation pressure is maintained by the second flapper valve.

As part of the hernia repair procedure, additional gas-tight trocar sleeves (not shown) are inserted through the abdominal wall into the working space. The same procedure as described above in connection with FIG. 3I is used to attach a mesh patch to the properitoneal fascia over the site of the hernia. The process can be observed with the aid of an endoscope (not shown) passed into the working space through the bore of the inner tube 235, or through one of the additional trocar sleeves.

After the treatment procedure is completed, the valve 285 is operated to release the insufflation gas from the working space. The valve 231 is operated to release the inflation fluid from the main inflatable chamber 213, which releases compression from the abdominal wall, excluding the peritoneum. The main envelope returns to its collapsed state inside the bore of the outer tube 237.

The tube assembly is then withdrawn from the incision, and the incision is closed using sutures or clips. The pressure of the viscera against the peritoneum returns the peritoneum into contact with the underlying layer. Over time, the peritoneum reattaches to the underlying layer.

4. HERNIA REPAIR METHOD WITH INCISION AT THE UMBILICUS

The hernia repair methods described so far show the incision placed close to the site of the hernia. In practice, it is preferred to make the incision at or near the umbilicus because the boundary between the peritoneum and the properitoneal fat layer can be more directly accessed near the umbilicus. The midline location of the umbilicus is devoid of muscle layers that would otherwise need to be traversed to reach the properitoneal fat layer.

Apparatus of the types described above inserted through an incision at the umbilicus would require a very large main inflatable chamber to detach the peritoneum from the umbilicus to the groin. Instead, in the method according to the invention to be described next, an apparatus of any one of the types described above is used to provide a tunnel from an incision at the umbilicus to the site of the hernia in the groin, and then to provide an insufflated working space at the site of the hernia.

The main envelope is partially expanded, collapsed, and advanced towards the site of the hernia. This sequence is repeated to progressively separate the peritoneum from the underlying layer and form the tunnel from the umbilicus to the site of the hernia. Then, at or near the site of the hernia, the main envelope is fully expanded to provide the working space at the site of the hernia. The working space is then insufflated to maintain the separation of the peritoneum from the underlying layer.

The following method can be practiced using the two-component embodiment of the apparatus, or any of the one-component embodiments of the apparatus. The method will be described using the two-component apparatus.

Figure 10A:
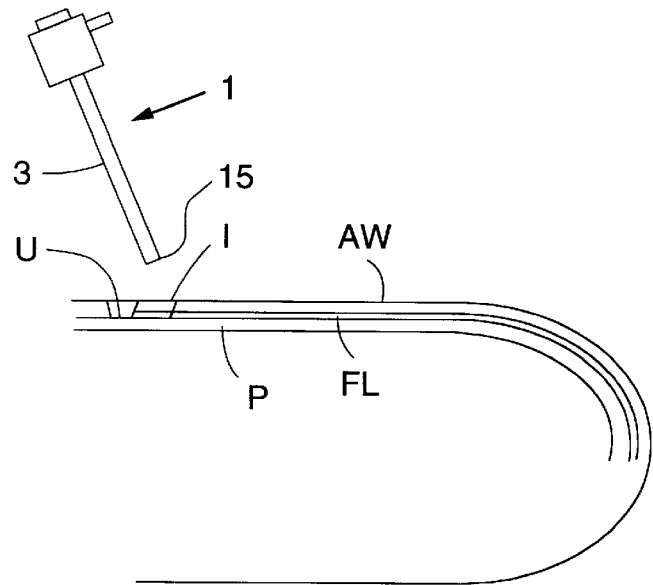
FIGS. 10A through 10I illustrate the alternative method according to the invention of using any of the apparatus according to the invention to separate the peritoneum from the underlying layer near the groin, with the apparatus inserted through an incision near the umbilicus.

An incision about 12–15 mm long is made in the abdominal wall AW, and is carried through the abdominal wall as far as, and including, the properitoneal fat layer FL. The incision is made at the umbilicus U, as shown in FIG. 10A.

Figure 10B:
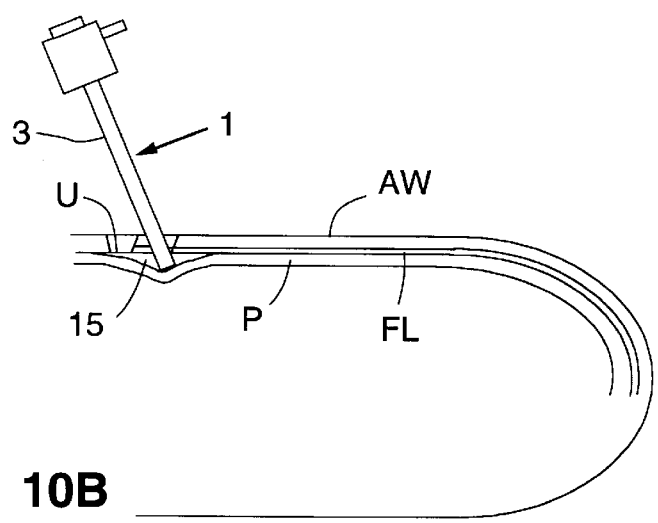

The distal end 15 of the introducer tube 3 of the separation component 1 is then inserted into the incision to bring the distal end into contact with the peritoneum P. Additional gentle pressure detaches the part of the peritoneum in the immediate vicinity of the incision from the underlying layer, as shown in FIG. 10B. In FIG. 10B, the peritoneum is shown detached from the properitoneal fat layer FL. The main envelope cannot be seen in these figures because it is inverted within the bore of the introducer tube 3.

Figure 10C:
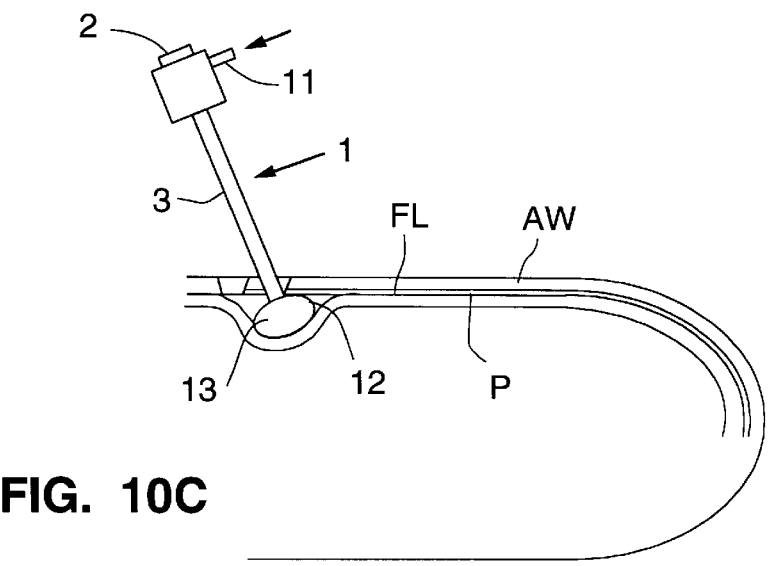

A source of a suitable inflation fluid (not shown), as previously described, is connected to the valve 11. The flow of inflation fluid is turned on, which ejects the main envelope 12 of the main inflatable chamber 13 from the bore of the introducer tube 3. The inflation fluid progressively expands the main envelope 12, and hence the main inflatable chamber 13 defined by the main envelope, into a partially-expanded state, as shown in FIG. 10C. The main envelope expands between the peritoneum and the properitoneal fat layer FL, and gently and progressively detaches an increasing area of the peritoneum P from the underlying layer near the umbilicus as it expands.

An endoscope (not shown) can be inserted into the main inflatable chamber 13 through the flapper valve 2 and the bore of the introducer tube 3. The endoscope can be used to observe the extent of the separation of the peritoneum, as described above.

Figure 10D:
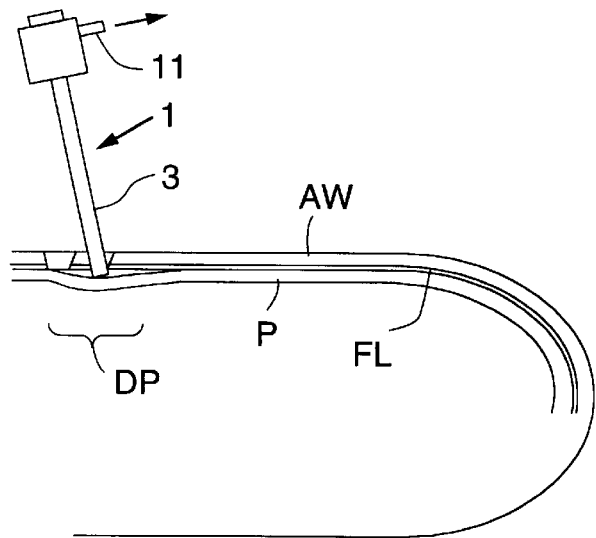

When the main envelope 12 expanded such that the main inflatable chamber 13 is about one-fourth of its fully-expanded diameter, i.e., about 1.0"–1.5" (25–37 mm) in diameter, the supply of inflation fluid is turned off. The valve 11 is then operated to vent inflation fluid from the main inflatable chamber 13. The main envelope progressively returns to its collapsed state, as shown in FIG. 10D. The peritoneum DP that was separated by the main inflatable chamber remains detached from the underlying layer, however, as shown. Alternatively, the main envelope can be inflated to a fully-expanded state.

Figure 10E:
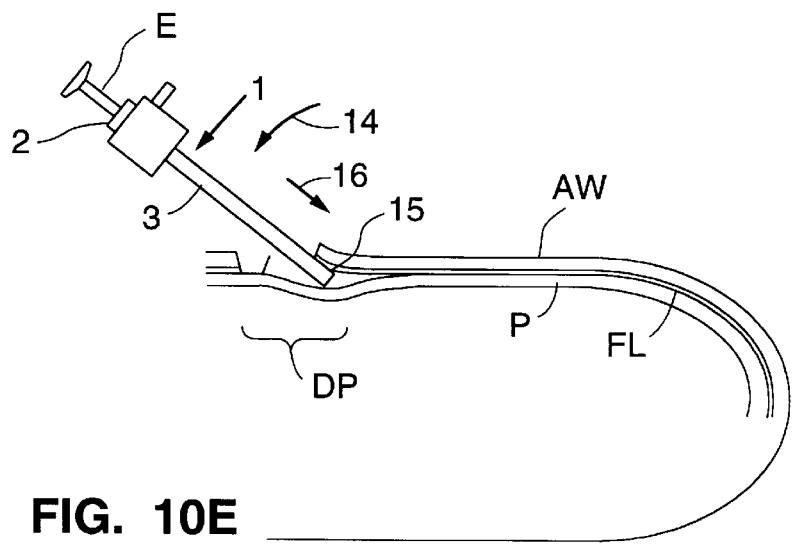

The separation component 1, including the collapsed main envelope 12, is then manipulated in the direction indicated by the arrow 14, and then in the direction indicated by the arrow 16, to advance the distal part 15 of the introducer tube 3 to the limit of the detached part of the peritoneum DP in the direction of the groin, as shown in FIG. 10E. An endoscope E inserted through the flapper valve 2 into the bore of the introducer tube 3 enables the position of the distal part of the introducer tube relative to the detached part of the peritoneum to be observed.

Figure 10F:
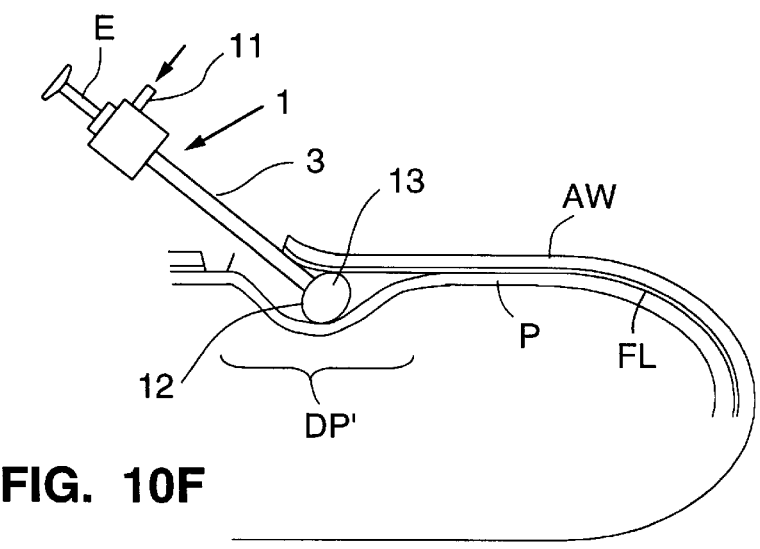

Once the distal part 15 of the introducer tube has been positioned, the separation component 1 is clamped in position, or is gripped, and inflation fluid is once more passed through the valve 11, and the bore of the introducer tube 3 into the main inflatable chamber 13. The main envelope 12 expands once more, increasing the extent of the detached part of the peritoneum towards the groin, as shown in FIG. 10F. The increased extent of the detached part of the peritoneum is indicated by the line DP' in the figure. It should be noted that the extent of the detached part of the peritoneum is increased in the direction from the umbilicus to the groin, but not in the direction transverse to this direction. The endoscope E is used to observe the extent of the separation.

The process of collapsing the main envelope 12, advancing the distal part 15 of the introducer tube to the limit of the detached part of the peritoneum DP, in the direction of the groin, holding the introducer tube in position, and partially re-inflating the main envelope 12, is repeated until the detached part of the peritoneum includes the peritoneum over the site of the hernia. This process provides the tunnel T between the incision at the umbilicus and the site of the hernia. This can be seen in FIG. 10I. Alternatively, the main envelope can be fully re-inflated.

Figure 10G:
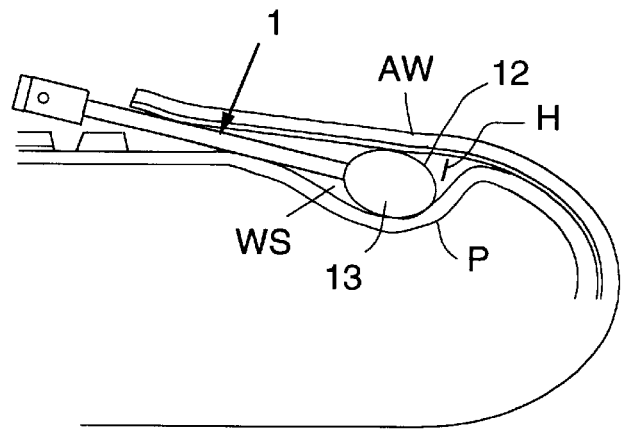

When the main envelope is in the vicinity of the site of the hernia H, the main envelope 12 is fully inflated to form a working space WS including the site of the hernia. This is shown in FIG. 10G.

Figure 10H:
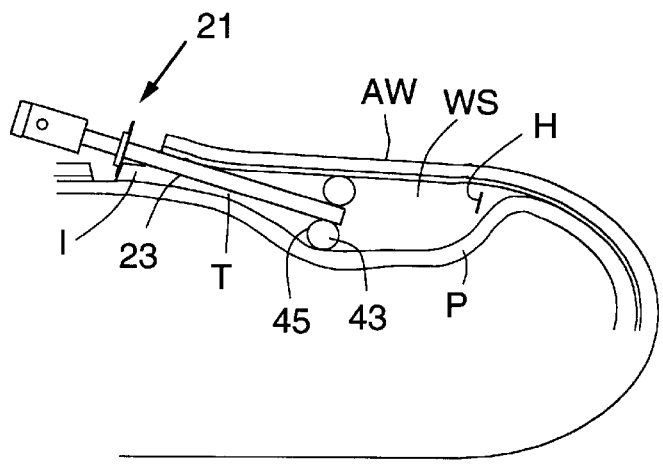

The working space at the site of the hernia is then insufflated. With the two-component apparatus, inflation fluid is vented from the main inflatable chamber 13 to collapse the main envelope 12, and the separation component 1 is withdrawn from the tunnel T through the incision I. The insufflation component 21 is introduced into the incision, and advanced through the tunnel until the envelope 45 of the toroidal inflatable chamber 43 lies within the working space WS, clear of the tunnel. The toroidal inflatable chamber is inflated, the anchor flange is clamped in position, and insufflation gas is passed into the working space, as shown in FIG. 10H. The toroidal inflatable chamber provides a gas-tight seal with the entrance of the tunnel.

Figure 10I:
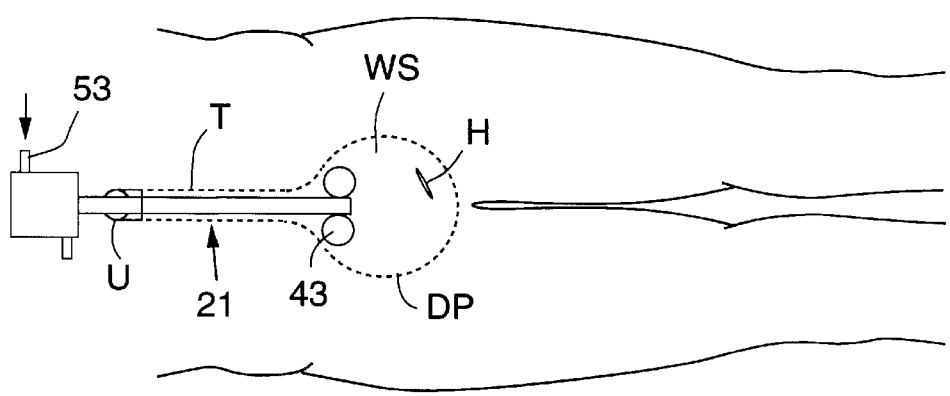

FIG. 10I shows a plan view of the abdomen with the insufflator component 21 in place. The anchor flange has been omitted for clarity. The toroidal inflatable chamber 43 provides a gas-tight seal with the entrance of the tunnel T. The extent of the separated peritoneum is indicated by the dotted line DP. It can be seen that the lateral extent of the separated peritoneum is considerably greater in the working space WS than in the tunnel T.

With the first embodiment of the one-component apparatus, inflation fluid is vented from the main inflatable chamber to collapse the main envelope, and the main envelope is withdrawn from the working space through the bore of the tube assembly. The tube assembly is partially withdrawn until the envelope of the toroidal inflatable chamber lies within the working space, clear of the entrance to the tunnel. The toroidal inflatable chamber is inflated, the anchor flange is clamped in position and insufflation gas is passed into the working space, as already described. The toroidal inflatable chamber seals against the entrance from the tunnel into the working space.

Using the second embodiment of the one-component apparatus, the main envelope is preferably returned to a partially collapsed state, the tube assembly is partially withdrawn until the main inflatable chamber lies within the working space, adjacent to the entrance of the tunnel. The anchor flange is clamped in position, and insufflation gas is passed into the working space, as already described. The partially-collapsed main chamber seals against the entrance from the tunnel into the working space.

If the main envelope is inflated to a fully expanded state during the separation part of the procedure, the whole of the space is insufflated with a gas-tight seal at the incision, as previously described.

Irrespective of the embodiment of the apparatus used to create the insufflated working space WS, the hernia is then repaired using the procedure described in connection with FIG. 3I.

5. INFLATABLE CHAMBERS FOR MAINTAINING SEPARATION OF TISSUE LAYERS

As previously discussed, during dissection of the properitoneal space or during subsequent surgical procedures near the peritoneum, it is common to puncture or otherwise breach the peritoneum. Such a puncture or breach prevents the properitoneal space from retaining pressurized fluid (gas or liquid) used to maintain the space in an open condition. If pressure is lost, visualization of the space and the actual volume of the space will decrease and compromise the surgery. Absent some way of mechanically maintaining the space, loss of pressure can result in inability to complete the procedure.

An additional consideration in laparscopic surgery inside the peritoneal space is fouling of the distal end of the endoscope with body fluids caused by incidental contact with either tissues near the entry point of the endoscope or tissues near the distal end of the cannula through which the endoscope has been inserted.

(a) First Inflatable Chamber

Figure 11A:
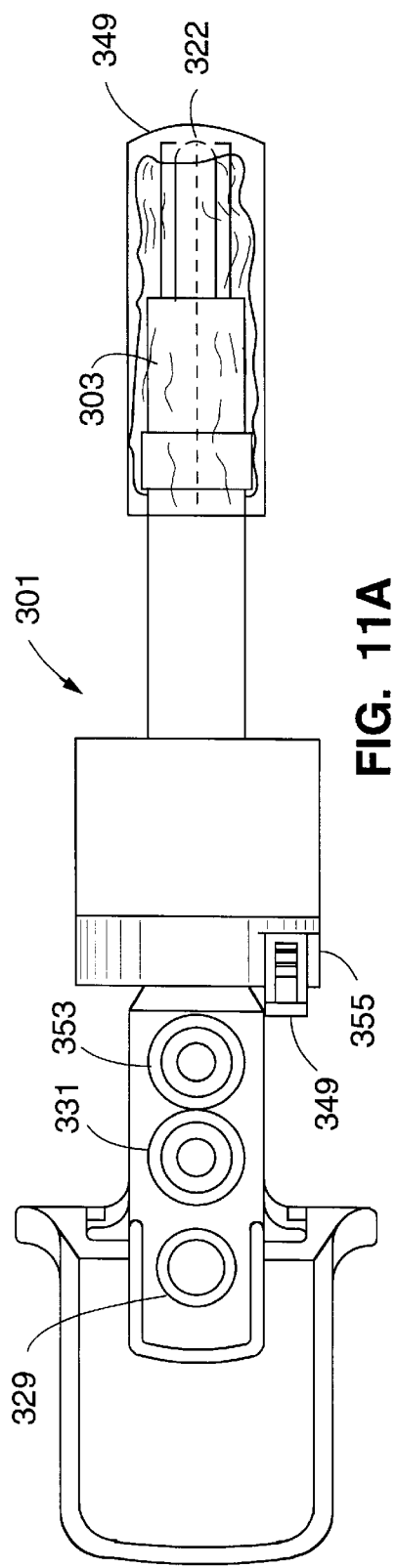
Figure 11B:
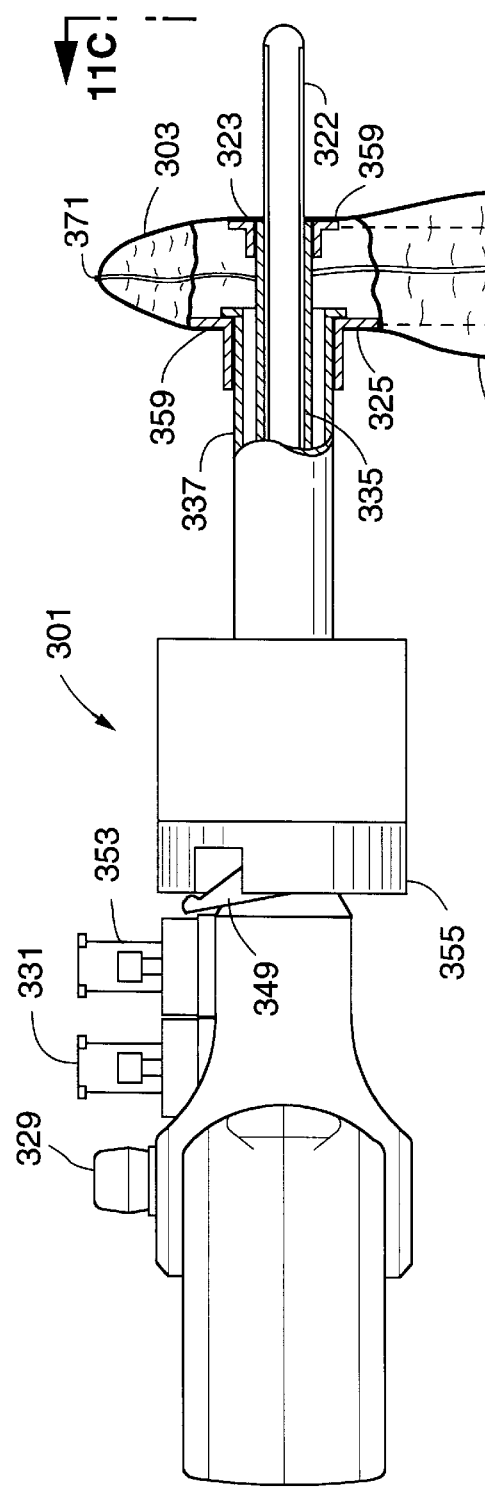

Referring to FIGS. 11A and 11B, an insufflation and retraction device 301 having a first inflatable chamber 303 is shown. The insufflation and retraction device 301 is similar to the insufflation component 21 of the two-component apparatus, shown in FIGS. 2D and 2E, and like reference numerals represent like components. It is understood that although it is preferred to use the inflatable chambers described below with the insufflation and retraction device 301, the inflatable chambers may also be used with any other delivery or inflation device.

The insufflation and retraction device 301 includes an inner tube 335 and a coaxial outer tube 337. The distal end 323 of the inner tube 335 extends beyond the distal end 325 of the outer tube 337. The inner tube 335 is similar to the introducer tube 3 (FIG. 2A) and is a rigid tube having a bore with a circular cross section that can preferably accommodate a 10 mm endoscope, however, any cross-sectional shape or area may be provided. The proximal end of the inner tube 335 is fitted with a flapper valve as described above in connection with the insufflation component of FIGS. 2D and 2E. A seat at the proximal end of the inner tube forms a gas-tight seal with an appropriately sized instrument. A shutter covers the seat and is operated by a button 329. A blunt obturator 322 is shown extending through the seat and through the distal end 323 of the inner tube 335 (FIGS. 11A and 11B). A valve 331 is fluidly coupled to the interior of the inner tube 335 and may be used to supply insufflation gas or liquid.

The first inflatable chamber 303 has a distal side 343 coupled to the inner tube 335 and a proximal side 345 coupled to the outer tube 337 so that the interior of the inflatable chamber 303 is fluidly coupled to the annular space between the inner and outer tubes 335, 337. The proximal and distal sides 345, 347 of the inflatable chamber 303 are preferably attached to the inner and outer tubes 335, 337 at flanges 359. A valve 353 is adapted to be connected to a source of a suitable inflation gas or liquid (not shown) for inflating the inflatable chamber 303. The inflatable chamber 303 is shown in a collapsed state in FIG. 11A and in an expanded state in FIGS. 11B and 11C.

An anchor flange 355 is slidably mounted to the outer tube 337 and can be locked along the length of the outer tube 337 with a locking lever 349. The anchor flange 355 helps to immobilize the device and, further, helps the inflatable chamber 303 form a seal to limit the escape of insufflation gas during laparoscopic procedures. When the anchor flange 355 is locked into position, the anchor flange 355 and inflatable chamber 303 apply a modest compressive force to the tissue between the inflatable chamber 303 and the anchor flange 355 thereby improving the gas-seal.

Referring to FIG. 11A, the inflatable chamber 303 is folded and contained within a sheath 349 before insertion into a patient. The inflatable chamber 303 may be folded in any manner but is preferably folded inwardly from lateral, side edges 351, 353 toward the extended distal end of obturator 322. The sheath 349 is preferably perforated but may be formed in any other manner permitting easy opening. The inflatable chamber 303 is initially in the folded, compact orientation of FIG. 11A before insertion into the patient so that the retraction device may be easily inserted through a small opening in the patient. As will be described below, after the inflatable chamber 303 has been positioned within a patient and between the two tissue layers to be separated, inflation air is injected into the inflatable chamber 303 through the second valve 353. Inflation of the chamber 303 tears the sheath 349 along the perforation 361 and releases the inflation chamber 303. Alternatively, the sheath 361 may include an independent opening mechanism, such as a removable thread which binds the sheath together.

Referring to FIG. 11C, the inflatable chamber 303 preferably has a substantially trapezoidal shape. First and second sides 363, 365 of the inflatable chamber 303 are preferably slightly curved but may also be linear or bi-linear. The first and second sides 363, 365 and lateral sides 351, 353 may also include surface features such as ridges or rounded teeth to help anchor the inflatable chamber 313 and improve the insufflation gas seal. The second side 365 is preferably longer than the first side 363 and forms angles of less than 90 degrees with the lateral sides 351, 353. Furthermore, the inner and outer tubes 335, 337 are preferably connected to the inflatable chamber 303 closer to the first side 363 than the second side 365. A throughhole 358 is defined by the outer tube and extends through the first and second sheets. The shape of inflatable chamber 303 may also be modified and/or optimized to suit the particular use contemplated. The location and configuration of the throughhole 358 may also be modified.

The inflatable chamber 303 is formed with first and second sheets 367, 369 attached together along a periphery 371. This arrangement results in relatively high localized stress at the periphery 371 of the first and second sheets 367, 369. To withstand this stress, the strength of the sheets must be increased. One way of increasing the strength of the sheets is to increase the thickness of the sheets. A problem with simply increasing the sheet thickness is that the inflatable chamber 303 becomes larger in the collapsed state (FIG. 11A) which will causes more problems during insertion into a patient.

To alleviate the problem of localized stresses without increasing the sheet thickness, the present invention provides baffles 373 disposed between the first and second sheets 367, 369. The baffles 373 interconnect the first and second sheets 367, 369 and help absorb the pressure forces thereby reducing stresses at the periphery 371. The baffles 373 also help define the shape of the inflatable chamber 303 and limit the separation distance between the first and second sheets 367, 369 when the inflatable chamber 303 is in the expanded shape. The preferred method of attaching the baffles 373 to the first and second sheets 367, 369 is described below.

(i) Preferred Material for the Inflatable Chamber

The first and second sheets 367, 369 and baffles 373 are preferably made of a polyester and polyurethane composite material. Polyester has desirable strength characteristics but it is relatively rigid and crinkles easily. Moreover, polyester is very difficult to RF weld which is a preferred method of connecting the baffles and sheets together as will be described below. Polyurethane, on the other hand, is soft, non-abrasive, and easy to RF weld. Unfortunately, the tensile strength of polyurethane is relatively low. The composite material exploits the advantages of both polyester and polyurethane.

The composite material is formed by bonding polyurethane to a nylon or polyester film having a preferred thickness of about 0.5 to 2 mil. (12–50 $\mu$m), although a polyester fabric may also be used. The nylon or polyester fabric may be a woven fabric or may be composed of randomly-oriented fibers. The film or fabric layer is laminated (or cast, captured or encapsulated) between two polyurethane layers to provide a composite material having a preferred thickness of about 3 mil. (75 $\mu$m). The resulting composite material is strong, supple, non-abrasive, transparent, and easily RF welded. The composite material will also fold with small radius folds so that the inflatable chamber 303 can be compacted into a small volume for easy insertion into a patient.

The composite material is relatively inelastic and, therefore, must be folded into the sheath as described above (FIG. 11A). The present invention may also be practiced with an elastic material which, when expanded, provides the shape of the inflatable chambers of the present invention. The composite material is disclosed in co-pending U.S. patent application Ser. No. 08/134,573, filed Oct. 8, 1993, which is herein incorporated by reference.

(ii) Method of Constructing the Inflatable Chamber

Figure 13A:
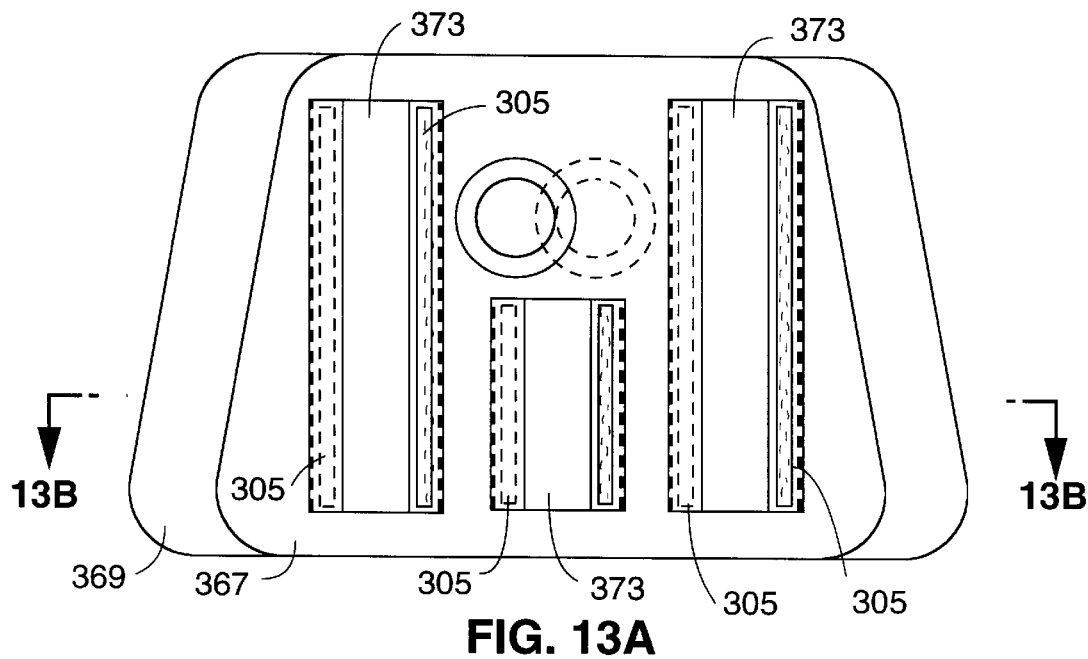
Figure 13B:
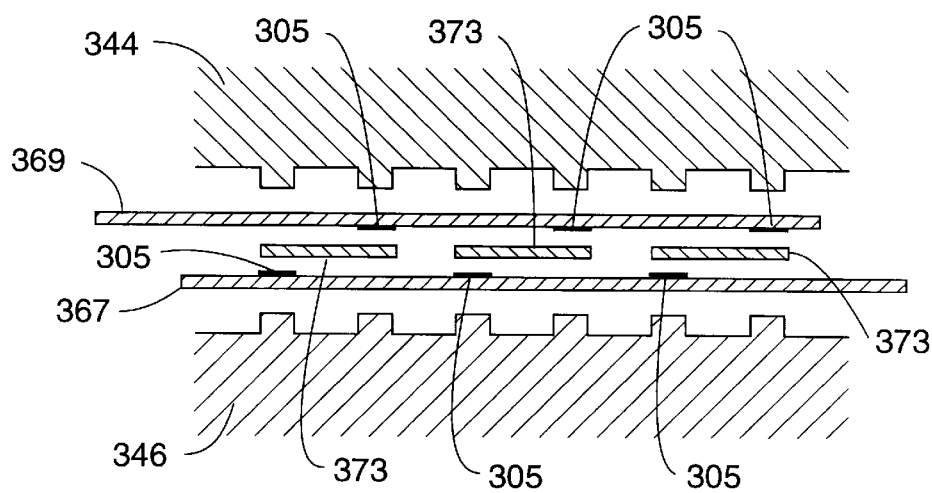
Figure 13C:
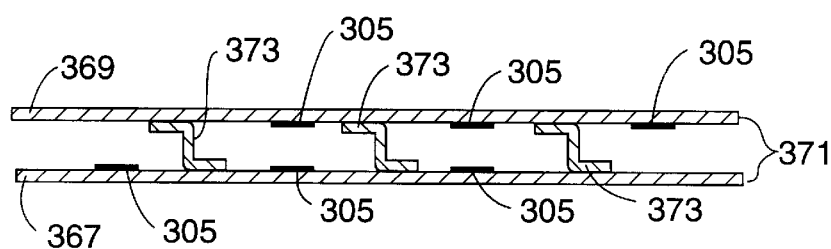

The baffles 373 are preferably fabricated and attached to the first and second sheets 367, 369 in the manner shown in FIGS. 13A through 13C. The first and second sheets 367, 369 and baffles 373 are cut into the desired shape and oriented as shown in FIG. 13A with the first and second sheets 367, 369 being offset with respect to one another. The baffles preferably do not extend completely between the first and second sides so that all portions of the interior of the inflatable chamber are fluidly coupled together. Alternatively, the baffles 373 may include openings to fluidly couple the various portions together. The baffles 373 are preferably made of the same material as the first and second sheets but may also be made of a different material.

Referring to the exploded cross-sectional view of FIG. 13B, RF welding electrodes 344, 346 are positioned against the first and second sheets 367, 369. RF welding imparts radio frequency energy to the working piece. When radio frequency energy is imparted onto polyurethane, the molecules are excited and the polyurethane melts thereby bonding together adjacent polyurethane layers together. A suitable release agent 305 is applied to either the sheets 367, 369 or baffles 373 to prevent formation of RF welds at certain locations. A preferred release agent 305 is powdered polyethylene and teflon. Without the releasing agent 305, the baffle 373 would be RF welded to both the first and second sheets 367, 369 on both sides. Application of the release agent 305 advantageously enables attaching the baffles 373 to the sheets in a single welding operation.

The RF welding apparatus is activated to weld the baffles 373 to the first and second sheets 367, 369. Adjacent polyurethane layers bond at all locations between the RF welding electrodes 375 except where the release agent 305 has been applied. The first and second sheets are then displaced so that they overlie one another as shown in FIG. 13C. The resulting baffles 373 have a generally S-shaped configuration when the inflatable chamber is in the expanded condition. A second RF welding operation (not shown) welds the periphery 371 of the first and second sheets together 367, 369.

(b) Second Inflatable Chamber for Maintaining Separation of Tissue Layers

A second inflatable chamber 403 for maintaining separation between tissue layers is shown in FIGS. 12A and 12B. The second inflatable chamber 403 includes an intermediate weld 405 which reduces pressure induced stresses at the periphery 471 of the inflatable chamber 403. The intermediate weld 405 eliminates the need to provide baffles, however, baffles may also be provided if necessary. The intermediate weld 405 is preferably a semi-circular segment having terminal ends 407 positioned adjacent the periphery 471. An interior area 411 is fluidly coupled to the remainder of the inflatable chamber 403 via two fluid paths 413 so that when the inflatable chamber 403 is inflated, the interior area 411 is also inflated. The fluid paths 413 are preferably provided between the terminal ends 407 of the intermediate weld 405 and the periphery 471; however, the fluid path 413 may be positioned anywhere along the intermediate weld 405. Furthermore, although it is preferred to provide two fluid paths, any number of paths may be provided.

The periphery 471 of the inflatable chamber 403 is substantially bell-shaped with the hemispherical interior area 411 protruding slightly from a bottom side 413. The bell-shaped periphery 471 has a semi-circular upper portion 415 which is substantially concentric with a throughhole 417. The remainder of the peripheral wall 471 is shaped like a truncated triangle extending downward from the semi-circular upper portion 415. As previously described, the shape of the inflatable chamber may be modified to suit the particular use contemplated. Materials and construction techniques are as described previously.

(c) Third Inflatable Chamber for Maintaining Separation of Tissue Layers

Referring to FIGS. 14A and 14B, a third inflatable chamber 503 is shown which also includes intermediate welds 505. The inflatable chamber 503 is advantageously formed from only first and second sheets 567, 569 of material. The intermediate welds 505 are preferably circular but may take any other shape. The intermediate welds bond the first and second sheets 567, 569 together throughowelds. Before insertion into a patiewelds. Before insertion into a patient, the inflatable chamber 504 is preferably folded and contained within a perforated sheath as described above in connection with the first inflatable chamber 303.

The inflatable chamber 503 has a substantially trapezoidal shaped periphery 571. The sides 507, 509, 511, 513 of the inflatable chamber are preferably linear but may also be curved. A first side 507 is smaller than a second side 509 and the second side preferably forms an angle of between 20 and 90 degrees with the lateral sides 511, 513.

(d) Fourth Inflatable Chamber for Maintaining Separation of Tissue Layers

Referring to FIGS. 15A and 15B, a fourth inflatable chamber 603 is shown which has the same general features as the second inflatable chamber 403, however, inflatable chamber 603 includes first and second extensions 621, 623 having a space 633 therebetween. The space 633 provides clearance for insertion of additional instruments into the working space while minimizing the risk that the additional instruments will pierce the inflatable chamber 603 as described below. A throughhole 617 extends through the inflatable chamber 603 which is adapted to be connected to the insufflation component of FIGS. 11A and 11B or may be connected to any other delivery or inflating device.

The fourth inflatable chamber 603 is preferably symmetrical about a line of symmetry 609 passing through the throughhole 617. First and second peripheral points 625, 627 are located on the line of symmetry 609 with the first peripheral point 625 being closer to the throughhole 627 than the second peripheral point 627. The first and second extensions 621, 623 have radially outward points 629, 631. A line 630 passing through the center of the throughhole 617 and the radially outward to points 629, 631 preferably forms an angle A between 10 degrees and 80 degrees with respect to a line 632 extending between the throughhole and the first peripheral point 625. The extensions are preferably triangular-shaped with rounded edges but may also take any other shape so long as the space 633 is provided therebetween. Furthermore, the space 633 is also preferably triangular shaped but may also be semi-circular, square, or a relatively shallow circular segment. Modifications to the proportions illustrated as well as providing asymmetrical designs are also contemplated to suit the particular application.

During laparoscopic surgery, additional instruments are often introduced above the longitudinal axis of the delivery device. The space 633 between the extensions 621, 623 facilitates introduction of additional instruments along the longitudinal axis of the delivery device above the inflatable chamber 603 while minimizing the risk that the additional instruments will puncture the inflatable chamber 603.

The inflatable chamber 603 is preferably formed from first and second sheets 667, 669 of the composite material described above but may be formed in any other manner or with any other materials to provide the extensions 621, 623 and space 633 therebetween. The first and second sheets 667, 679 are preferably attached together about the periphery 671 by RF welding as described above. The first and second sheets 667, 669 are also preferably coupled together by an intermediate weld 605. The inflatable chamber 603 may also be formed with baffles or with a sheet material of sufficient thickness to withstand the stress at the periphery 671.

(e) Fifth Inflatable Chamber for Maintaining Separation of Tissue Layers

Referring to FIGS. 16A and 16B, a fifth inflatable chamber 703 is shown which is an alternative to inflatable chamber 303 of FIGS. 11B through 11C. The fifth inflatable chamber 703 may be used with any inflation or delivery device but is preferably used in connection with the insufflation component of FIGS. 2D and 2E or FIGS. 11A and 11B.

The fifth inflatable chamber 703 has essentially the same structural features as the first inflatable chamber 303, however, the inflatable chamber 703 includes a pair of triangular-shaped wings 705. The triangular wings 705 provide a wider working space within the patient than the inflatable chamber 303. The wings 705 may also advantageously provide additional tissue dissection when the chamber 703 is inflated.

Inflatable chamber 703 is preferably made from the same or like materials as inflatable chamber 303 and, furthermore, is constructed with baffles 707 in the same manner as inflatable chamber 303.

For the first, second, third, fourth and fifth embodiments of the inflatable chamber described above, it should be recognized that the shape of each embodiment has the common functional benefit of maintaining the properitoneal space by retaining the separation of the peritoneum from the overlying tissue in the event of loss of optimal pressurization or when a gasless technique is used.

More specifically, the embodiments each employ a bottom surface which contacts the peritoneum and an upper surface that contacts the overlying fascia. For example, in the first embodiment shown in FIG. 11C, the upper surface can be characterized as side 363 and the lower side characterized as side 365. The physical distance between the upper and lower surfaces causes like separation or the peritoneal layer and fascia layers in the dissected properitoneal cavity. The inflatable chamber can be dimensionally sized to create optimal separation while limiting potential trauma to tissue. Furthermore, the location of throughhole 358 within the inflatable chamber can be selected to optimize the separation of retracted tissue from an endoscope or other instrument passed through throughhole 358. Throughhole 358 thus can be centered or off-center in the inflatable chamber as desired. Preferably, throughhole 358 is located slightly off-center towards the upper surface, but centered laterally. Such a location optimizes the desired features of reducing endoscope fouling by body fluids as the scope is passed into throughhole 358, and separating the scope from the peritoneum to provide maximum viewing field with a scope through throughhole 358. The reduction of fouling is accomplished by displacing the throughhole 358 from the upper surface, and thus overlying fascia, to minimize potential tissue contact with throughhole 358 and an endoscope passed through throughhole 358. Likewise, the viewing field is maximized by separating throughhole 358, and thus an endoscope in it, from peritoneum being deflected downward by the lower surface of inflatable chamber.

6. HERNIA REPAIR METHOD WITH INCISION AT THE UMBILICUS

The hernia repair method described above in connection with the insufflation component having the toroidal inflatable chamber will know be described with respect to the fourth inflatable chamber 603 described above. It is understood that the following method may be practiced using any of the inflatable chambers 303, 403, 503, 603, 703.

Figure 17A:
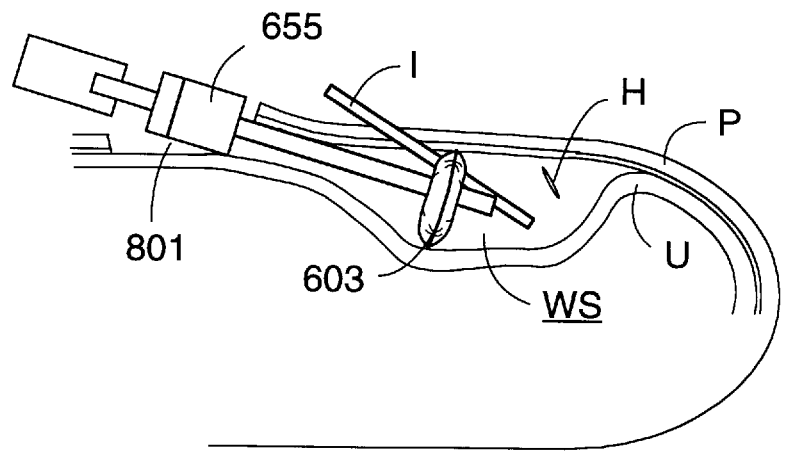
FIGS. 17A and 17B show a retraction device having the fourth inflatable chamber advanced through a tunnel into a working space and an additional instrument passing adjacent the fourth inflatable chamber.
Figure 17B:
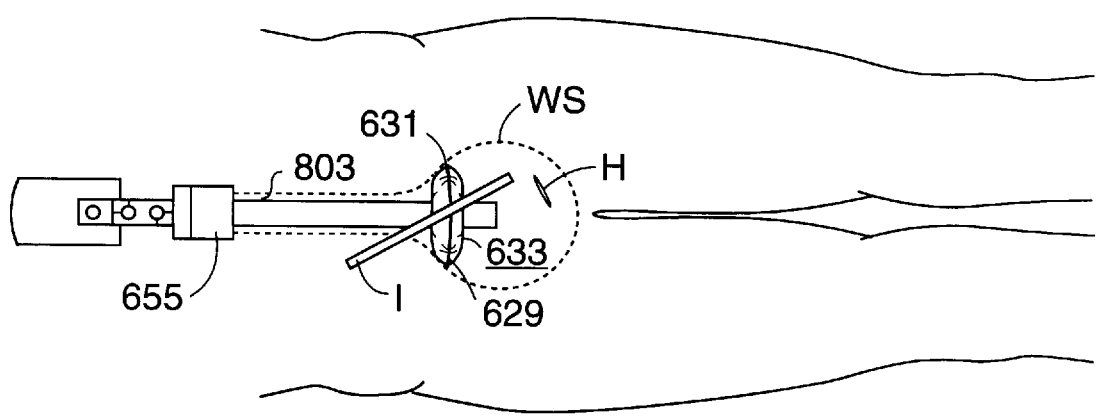

Referring to FIGS. 17A and 17B, an incision 801 is made at or near the umbilicus and a tunnel 803 is formed from the incision toward the site of the hernia. The peritoneum P is then dissected from the underlying layer U. The tissue layers are preferably dissected with the apparatus and methods described above; however, dissection may also be accomplished in a conventional manner. For example, dissection may be accomplished with an endoscope, graspers, an operating scope or any blunt instrument which may be used to dissect the tissue layers by sweeping the area between the layers.

Once the tissue layers have been dissected, the retraction device is inserted through the tunnel 803 while in the compact deflated condition of FIG. 11A. When the inflatable chamber 603 is within the working space WS, an inflation fluid (any suitable gas or liquid, such as air or saline) is injected into the inflatable chamber 603 thereby expanding the inflatable chamber to the shape of FIG. 17A. A conventional hand bulb or syringe can be used to inject the fluid through port 353. The anchor flange 655 is moved toward the distal end and locked in position so that a compressive force is exerted on the abdominal wall by the anchor flange 655 and inflatable chamber 603. The compressive force ensures that the inflatable chamber 603 forms a seal which inhibits the escape of insufflation gas through the tunnel 803. Insufflation gas is then passed into the working space WS and the hernia H is then repaired using the procedure described in connection with FIG. 31. During repair of the hernia, an additional instrument I may be introduced into the working chamber in the space 633 between the extensions 629, 631. The space 633 permits introduction of the additional instrument I while minimizing the risk that the additional instrument I might puncture the inflatable chamber 603.

7. METHOD AND APPARATUS FOR PACKING DEFLATED BALLOONS

As mentioned above, a known method of packing inflatable balloons is to roll the balloon inward from opposing sides of the chamber as shown in FIG. 18. A problem which occurs during inflation of the balloon packed in the known manner of FIG. 18 is that unrolling of the balloon can cause trauma to the tissue layer due to differential motion between the tissue layer and the balloon. Referring to FIG. 19, a balloon 807 compacted in the known manner of FIG. 18 is in a partially inflated state. During inflation, rolls 809 displaces outwardly with a top edge 811 rubbing against the upper tissue layer 813 which can cause trauma to the tissue layer.

The problem of traumatizing the tissue layers is particularly problematic when using an inflatable balloon in the properitoneal space. If the peritoneum is punctured or otherwise breached due to a tear caused by unrolling of the balloon, the properitoneal space cannot retain pressurized fluid to maintain the space. If pressure is lost, the volume of the space will decrease and compromise the surgery.

Referring to FIGS. 20 and 21, a preferred balloon 901 for dissecting the preperitoneal space is shown. The balloon 901 has a kidney-bean cross-sectional shape as shown in FIG. 21. It is understood that the present invention may be practiced using any shape balloon and the balloon 901 is merely an example. For example, the balloon 901 may also be spherical, oblong, cylindrical or any other shape suited for the particular dissection and/or retraction contemplated.

The balloon 901 is preferably mounted to an inflation and delivery device as shown in FIG. 2A but may also be attached to any other inflation and delivery device. The balloon is mounted to an introducer tube 903 having a bore 904 with a circular cross-section that can accommodate an endoscope. The bore 904 houses a fluid path 906 for inflating the balloon. The proximal end of the introducer tube is fitted with a port 905 in which is mounted a flapper valve 907. The shutter of the flapper valve is operated by a button 909. The flapper valve forms a gas-tight seal with an endoscope or other instrument inserted though the flapper valve into the bore of the introducer tube. The port is also fitted with a valve 911 to which a supply of a suitable inflation fluid can be connected. The inflation fluid passes through the valve, introducer tube and into the balloon 901.

The balloon 901 is preferably formed from first and second sheets 913, 915 in the manner described above in connection with the inflatable chambers of FIGS. 11–16. The balloon 901 is also preferably made of the materials and fabricated in the manner described above in connection with FIGS. 11–16. Other preferred materials include latex, silicone rubber, or polyurethane. Furthermore, although the term balloon is used, the inflatable balloon may be elastic or inelastic.

Referring to FIG. 22, a first portion 917 of the balloon is displaced-inwardly toward the interior of the balloon in accordance with a preferred method of packing the balloon. Although it is preferred to displace the first portion 917 of the balloon in a direction perpendicular to a longitudinal axis 919 of the introducer tube 903, the balloon 901 may also be displaced inwardly in any other direction.

Figure 24:
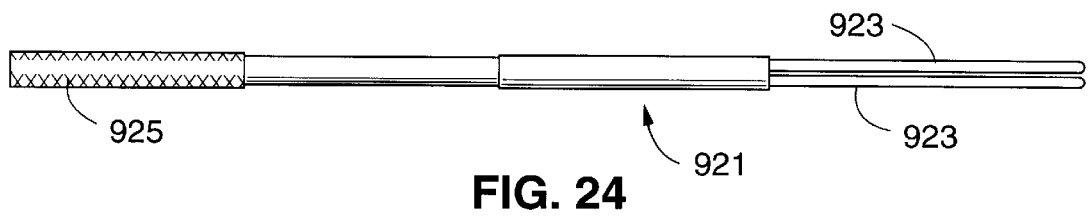
FIG. 24 shows the rolling device of FIG. 23 used for rolling-up the first inwardly-displaced portion of the balloon.

The first inwardly-displaced portion is then preferably rolled-up within the interior of the balloon with a rolling device 921 inserted through the bore of the introducer tube 903. Referring to FIGS. 23 and 24, the rolling device 921 includes two rolling rods 923 for grasping the first inwardly-displaced portion 917. Each rod 923 has a diameter of about ⅛ inch and a gap of preferably less than 1/16 inch therebetween. The gap size and diameter of the rods 923 may vary, of course, depending on the thickness of the balloon material. Furthermore, the rolling device 921 may include any other feature for grasping the inwardly displaced portion, such as a pair of jaws, a clamp or a pair of elastically deformable arms. The rolling device has a knurled handle for manipulating the rolling device.

Figure 25:
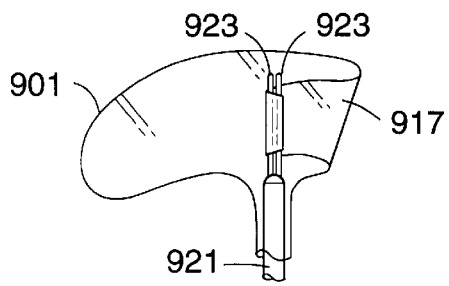
FIG. 25 shows the rolling device during rolling of the first portion of the balloon.
Figure 26:
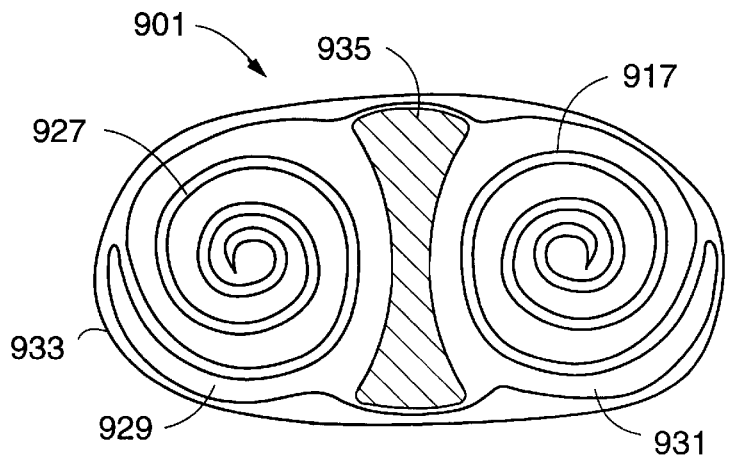
FIG. 26 shows a cross-sectional view of the balloon of FIG. 20 with first and second inwardly-displaced portions rolled-up into first and second rolls and an obturator positioned therebetween.

The rolling device 921 is rotated to roll the first portion as shown in FIG. 25. After the first portion has been rolled into a sufficiently compact roll, a second portion of the balloon is displaced inwardly and rolled in the same manner. The two rolls 929, 931 are then housed within a sheath 933 as described above in conjunction with the inflatable chambers of FIGS. 11–16. An obturator 935 is positioned in the bore of the introducer tube and between the two rolls 929, 931 to provide structural support for the balloon 901 during insertion into the patient. The obturator 935 is also shown in FIGS. 2E, 11A and 11B. The rolls 929, 931 are positioned on opposite sides of the obturator 935 with the obturator 935 including concave portions 937 for receiving the rolls 929, 931.

Figure 27:
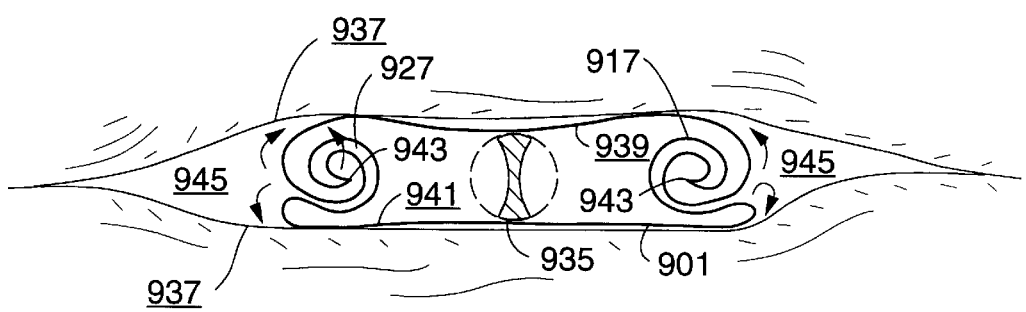
FIG. 27 shows the balloon of FIG. 26 during inflation and deployment between tissue layers.

The compact, deflated balloon is introduced into the patient between the two tissue layers to be separated and is then inflated. The balloon 901 may be used for dissecting and/or retracting tissue planes throughout the body. Referring to FIG. 27 which shows the balloon during inflation in the peritoneum, the inwardly-displaced portions evert during inflation so that differential motion between the balloon 901 and adjacent tissue layers 937 is minimized thereby reducing trauma to the tissue layers.

Figure 28:
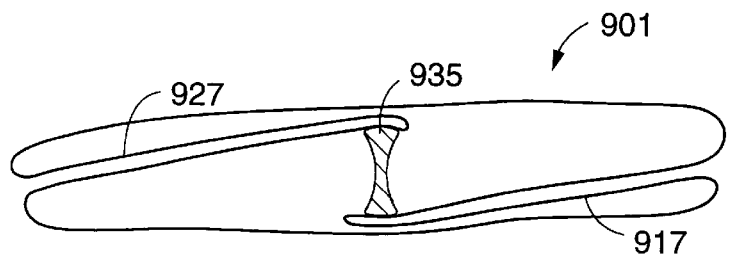
FIGS. 28 and 29 show a cross-sectional view of a balloon packed in accordance with another preferred method of packing a deflated balloon.
Figure 29:
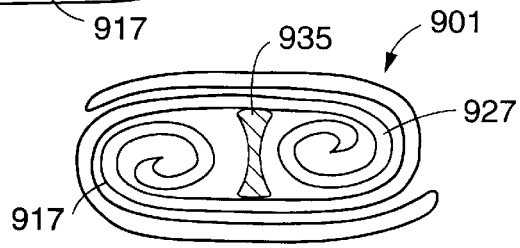

Although it is preferred to roll the first and second inwardly-displaced portions into first and second rolls 929, 931 within the interior of the balloon 901, the balloon 901 may be packed in any other manner so long as an inwardly-displaced portion is provided which everts during inflation. Referring to FIGS. 28 and 29, the inwardly-displaced portions 917, 927 may also be displaced to a side opposite the initial displacement and then rolled-up into the rolls as previously described.

Figure 30:
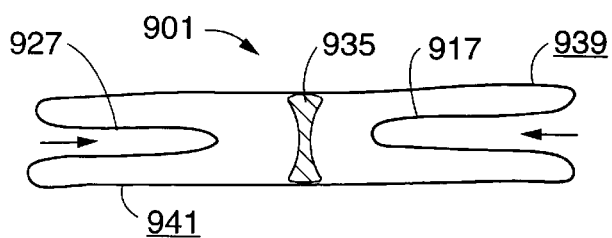
FIGS. 30 and 31 show a cross-sectional view of a balloon packed in accordance with another preferred method of packing a deflated balloon.
Figure 31:
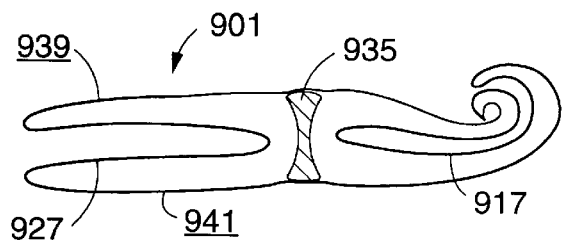

The first and second inwardly-displaced portions 917, 927 may also be rolled in the conventional manner from opposing lateral sides after displacing the portions inward as shown in FIGS. 30 and 31. The first and second portions 917, 927 divide the balloon 901 into an upper part 939 and a lower part 941. The upper part 939, first portion 917 and lower part 941 are then rolled-up in the conventional manner as shown in FIG. 31. When the balloon 901 is rolled in the manner shown in FIG. 30 and 31, the balloon 901 will suffer the problem of relatively high differential motion between the balloon 901 and the adjacent tissue layer during the initial inflation and deployment, however, during the end of the inflation, the balloon will have relatively low differential motion relative to the tissue layers. This method of packing a balloon is useful when problematic internal structures are positioned laterally outward from the obturator.

When the balloon is formed from first and second sheets 913, 915, the upper and lower parts are preferably formed by the first and second sheets 943, respectively. By configuring the balloon 901 in this manner, the first and second portions include a part of the seam 943 between the first and second sheets 913, 915. When coupling the first and second sheets 913, 915 together with an RF weld, the seam 943 forms a relatively thin, rigid periphery which can cut or otherwise traumatize the tissue layers. Referring to FIG. 27, the seam 943 everts into a space 945 between the tissue layers along the lateral edges of the balloon 901 thereby minimizing contact between the seam 943 and the tissue layers.

Figure 32:
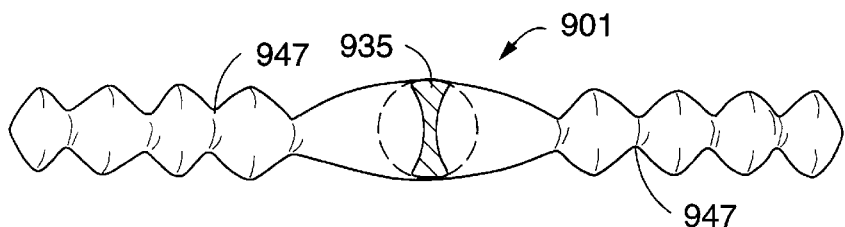
FIG. 32 shows a balloon having accordion-folds.
Figure 33:
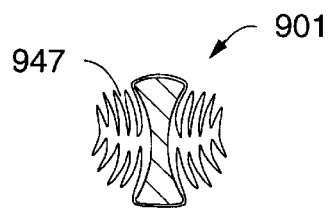
FIG. 33 shows the balloon of FIG. 32 in a compact state.

The balloon 901 may also include a number of inwardly-displaced portions in the form of accordion-folds 947 as shown in FIGS. 32. FIG. 33 illustrates the balloon of FIG. 32 in the compact, deflated state.

Although individual preferred embodiments have been described, the invention may be practiced using any combination of preferred features. For example, a small roll may be formed in the manner shown in the FIGS. 23 and 25 followed by the procedure shown in FIG. 31.

8. BALLOON CANNULA SYSTEMS

Figure 34:
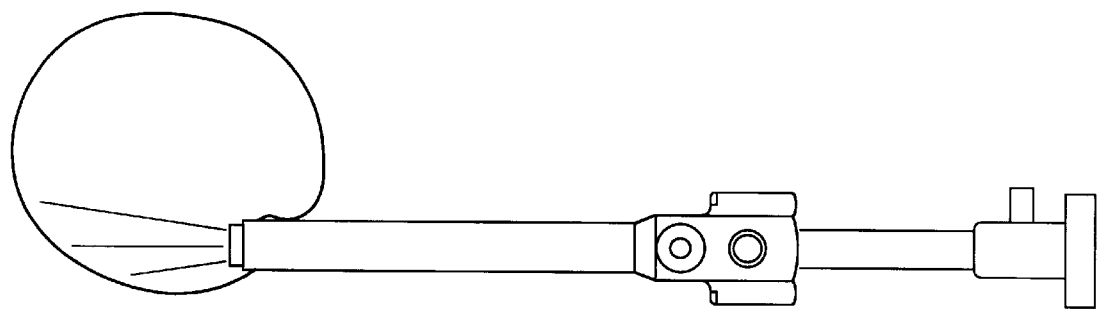
FIG. 34 shows a balloon mounted to a distal end of a delivery device with the inflated balloon being skewed and off-center.

As mentioned above, a known method of attaching an inflatable balloon to a delivery device is to attach the balloon to the distal end of a cannula. A problem which can occur during inflation of the balloon is that the balloon can become skewed and off-center as shown in FIG. 34. The balloon becomes skewed and off-center since the balloon is not supported during inflation and becomes skewed due to the forces imparted on the balloon by the adjacent tissue layers.

Figure 35:
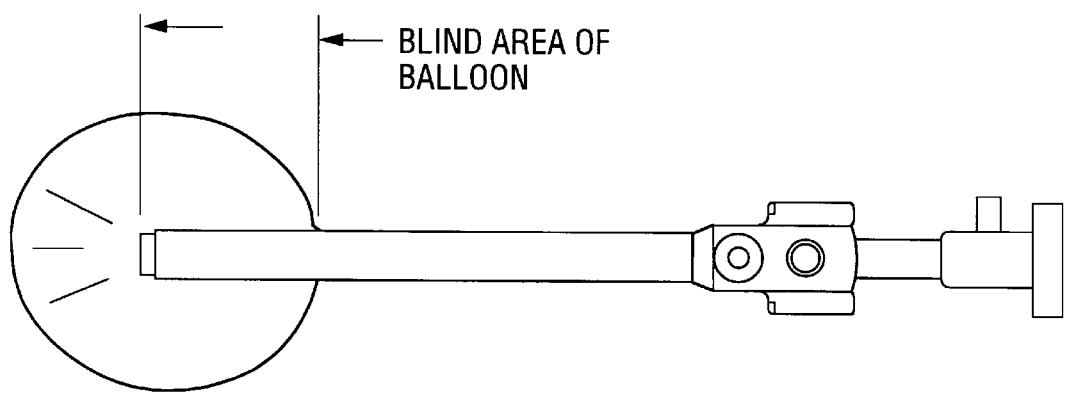
FIG. 35 shows a balloon mounted away from the distal end of a delivery and inflation device.

Another known method of attaching a balloon to an inflation and delivery device is to mount the balloon to the delivery device away from the distal end of the cannula so that the cannula extends into the interior of the balloon. The cannula provides structural support for the balloon during inflation as shown in FIG. 35. A problem which occurs when mounting the balloon away from the distal end of the cannula is that the visual field of an endoscope inserted in the device is limited. The endoscope has a blind area behind the distal end of the cannula (FIG. 35).

The balloon cannula systems of the present invention provide a supporting a portion which extends into the interior of the balloon to provide support for the balloon during inflation. After inflation of the balloon, the supporting part is removed from the interior of the balloon so that an endoscope inserted into the interior of the balloon has a visual field which is not limited as described above. The balloon cannula systems described herein may be used in any procedure requiring dissection and/or retraction of tissue planes throughout the body.

A. First Balloon Cannula System

Referring to FIG. 36, a first balloon cannula system 948 is shown. The first balloon cannula system 948 includes a delivery device 949 and an insert 950. An outer cannula 951 is mounted to the delivery device 949 and an inner cannula 952 is mounted to the insert 950. An obturator 33, as described above, is also provided but is not necessary for practicing the invention.

The delivery device 949 is preferably the same as described above in conjunction with FIGS. 2A, 2D, 2E, 11A, and 11B and the same reference numbers refer to the same items. The delivery device 949 includes an inflation port 953 for inflating a balloon 954 mounted to a distal end of the outer cannula 952. A button 9 operates a flapper valve 6 which is described above in conjunction with FIG. 2A. The flapper valve 6 seals a port 955 having a first elastomeric member 956 mounted thereto. Although it is preferred to use the delivery and inflation device of FIG. 2A, any other inflation or delivery device may be used.

The balloon 954 preferably has a substantially spherical shape when inflated. It is understood that the present invention may be practiced using any shape balloon and the spherical balloon 954 is merely an example. For example, the balloon may be oblong, cylindrical or any other shape suited for the particular dissection and/or retraction contemplated. The balloon 954 is preferably made of the materials described above. The balloon 954 is preferably packaged in a sheath as described above, however, the balloon 954 may also be packaged in any other manner.

Referring to FIG. 38, the insert 950 has an opening 957 at a proximal end which leads to an interior of the inner cannula 952. A clasp 958 is provided at the proximal end for locking the insert 950 to an instrument, such as an endoscpoe, passing through the opening 957. The clasp 958 preferably includes a simple over-center action locking lever 959. The opening 957 includes a second elastomeric member 960 which provides a substantially fluid tight seal with an appropriately sized instrument passing through the opening 957. The second elastomeric member 960 and instrument are preferably sized so that the fluid tight seal is maintained even when the instrument is displaced longitudinally relative to the insert 950.

A stop 961 is preferably attached to the distal end 962 of the inner cannula 952. The stop 961 ensures that the endoscope will be recessed from the distal end 962 of the inner cannula 952 as will be described in greater detail below. Referring to FIG. 41, the stop 961 preferably has an opening 963 which tapers inwardly toward the distal end 962 and is sized smaller than the distal end of the endoscope.

The inner cannula 952 includes a supporting portion 964 which supports the balloon 954 during inflation so that the balloon 954 does not become skewed and off-center. The supporting portion 964 is movable between an extended position, in which the supporting portion 964 extends into an interior 965 of the balloon 954 as shown in FIG. 41, and a retracted position, in which the supporting portion 964 is outside the interior 965 of the balloon 945 and housed within the outer cannula 951 as shown in FIG. 42.

The insert 950 and delivery device 949 are preferably configured to engage one another with a locking engagement. FIG. 37 shows an end view of the delivery device 949 and the insert 950. The insert 950 preferably includes a pair of lips 966 which engage recesses 967 in the delivery device 949. The insert 950 and delivery device 949 are coupled together and then rotated so that the lips 966 engage the recesses 967 thereby locking the insert 950 to the delivery device 949. The insert 950 and delivery device 949 may also engage one another in any other manner know to one having ordinary skill in the art, such as with a bayonet, cam-lock, or threaded connection.

The outer diameter of the inner cannula 952 is preferably sized to engage the first elastomeric member 956 to provide a substantially fluid tight seal therebetween. The fluid tight seal permits slidable movement between the insert 950 and the delivery device 949. The outer and inner cannulas 951, 952 are slidably movable relative to one another so that the supporting portion 964 is movable between the extended and retracted positions.

Operation of the first balloon cannula system 948 will now be described. Before being inserted into a patient, the first balloon cannula system 948 is configured as shown in FIG. 39. The inner cannula 952 is inserted through the port 955 in the delivery device 949 so that the supporting portion 964 of the inner cannula 952 extends beyond the distal end of the outer cannula 951 and into the interior 965 of the balloon 954. The supporting portion 964 of the inner cannula 952 extends beyond the distal end of the outer cannula 951 and provides support for the balloon 954 during inflation. The supporting portion 964 preferably extends at least half way to an opposing side 968 of the balloon 954 and more preferably extends at least three quarters the distance to the opposing side 968 of the balloon.

The insert 950 is then locked to the delivery device 949 by rotating the insert 950 so that the lips 966 engage the recesses 967. The obturator 33 is inserted through the opening 957 in the insert 950 and the clasp 958 is locked to lock the obturator 33 to the insert 950. The obturator 33 preferably has a blunt tip extending beyond the distal end of the inner cannula 952. The blunt tip reduces trauma to the patient when the balloon 954 is inserted into the patient. The blunt tip also prevents damage to the balloon 954 which might occur with a conventional trocar or other instrument.

The balloon 954 is then advanced in the patient until the balloon 954 is in the desired position for dissection and/or retraction. The clasp 958 is unlocked and the obturator 33 is removed. An endoscope E is introduced through the opening 957 in the insert 950 until the endoscope E contacts the stop 961. The stop 961 is preferably configured so that the distal end of the endoscope E is recessed from the distal end of the stop 961 between 2 mm and 10 mm and more preferably about 5 mm. By recessing the endoscope E from the distal end of the inner cannula 952, the endoscope E can visually access the tissue in contact with the balloon 954 without abutting against the inner surface of the balloon 954 and obscuring visualization.

A suitable inflation device is then attached to the inflation port 953 and a suitable inflation fluid is used to inflate the balloon 954. During inflation, the supporting portion 964 advantageously provides support for the balloon 954 so that the balloon 954 does not become skewed and off-center. The inflation fluid enters the balloon 954 through a fluid path 969 at least partially contained within the outer cannula 951. The term fluid path 969 as defined herein, refers to any structure which fluidly couples the inflation port 953 and the interior 965 of the balloon 954. For example, the fluid path 969 may be a tube which is separate from the inner and outer cannulas 952, 951. A preferred inflation device is a bulb (not shown) which delivers a controlled volume of the inflation fluid with each squeeze. A gas, preferably air, is the preferred inflation fluid, but other gases, such as carbon dioxide, can be used. A liquid, such as saline solution, can also be used, however, such liquids are less preferable because they change the optical properties of the endoscope E.

The insert 950 is then unlocked from the delivery device 949 by rotating the insert 950 to disengage the lips 966 from the recesses 967. The endoscope E remains locked to the insert 950 with the clasp 958 and, therefore, the endoscope E and insert 950 act as a single unit. Referring to FIG. 42, the insert 950 may be moved longitudinally in the direction of arrow A—A to provide optimal visualization of the tissue. The insert 950 is longitudinally movable so that the supporting portion 964 is movable between the extended and retracted positions. During movement between the extended and retracted positions, the inflation fluid is maintained in the balloon 954 by virtue of the substantially fluid tight seal between the first elastomeric member 956 and the insert 950. Supplemental inflation fluid can be provided through the inflation port 953 as necessary to make up for any fluid losses past the first elastomeric member 956.

B. Second Balloon Cannula System

Figure 45:
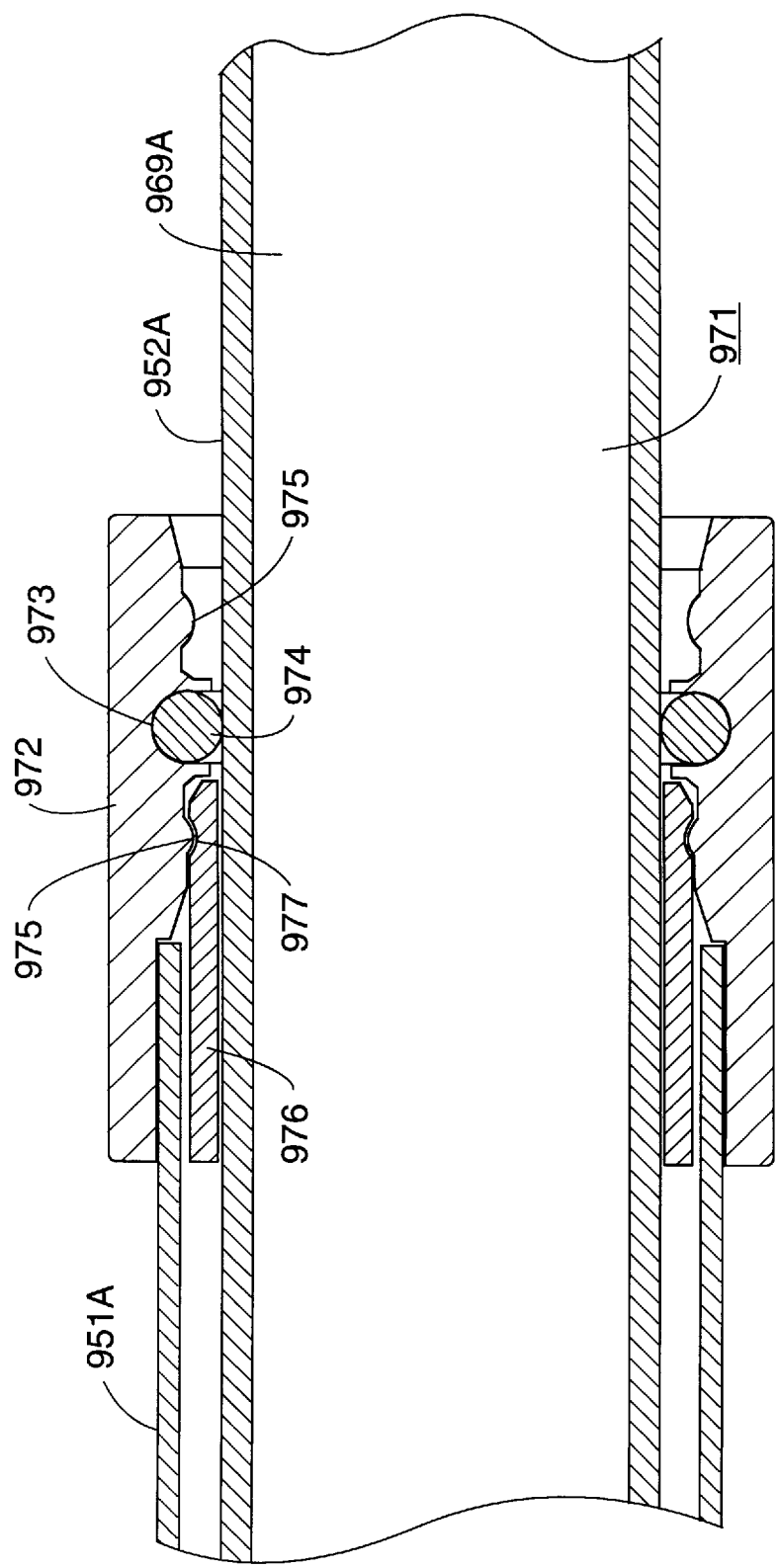
FIG. 45 is a cross-sectional view of a sleeve and a lock ring used to lock the outer cannula to the inner cannula.

Referring to FIGS. 43 through 45, a second balloon cannula system 948A is shown which includes a delivery device 949A and an outer cannula 951A. Reference numerals with an added "A" represent items similar to those described above in conjunction with the first balloon cannula system 948. An inner cannula 952A is mounted to the delivery device 949A and the outer cannula 951A is slidably mounted to the inner cannula 952A. The balloon 954, as described above, is mounted to the distal end of the outer cannula 951A.

The delivery device 949A is preferably the same as the delivery device 949 described above in conjunction with the first balloon cannula system. The inner cannula 952A has the stop 961 attached to the distal end. The delivery device 949A includes the inflation port 953 and button 9 which activates a flapper valve (not shown). The inflation port 953 is fluidly coupled to the interior 965 of the balloon 954 via a fluid path 969A at least partially defined by an interior 971 of the inner cannula 952A (FIG. 45). The fluid path 969A may take any form so long as it fluidly couples the interior 965 of the balloon 954 to the inflation port 953.

The outer cannula 951A is slidably mounted to the inner cannula 952A between an extended position, in which a supporting portion 964A of the inner cannula 952A extends into the interior 965 of the balloon 954 as shown in FIG. 43, and a retracted position, in which the supporting portion 964A of the inner cannula 952A is outside the interior 965 of the balloon 954 as shown in FIG. 44. Referring to FIG. 43, the supporting portion 964A preferably extends at least half the distance to the opposing side 968 of the balloon 954 and more preferably at least three quarters the distance to the opposing side 968.

The outer cannula 951A may be slidably coupled to the inner cannula 952A in any manner but is preferably slidably coupled to the inner cannula 952A via a sleeve 972. Referring to the exploded cross-sectional view of FIG. 45, the sleeve 972 includes a cavity 973 which receives a first o-ring 974. The first o-ring 974 provides a substantially fluid tight seal between the sleeve 972 and the inner cannula 952A so that inflation fluid pressure is maintained in the balloon 954. The sleeve 972 also includes a detent 975 on each side of the first o-ring 974. One of detents 975 engages one of lock rings 976 attached to the inner cannula 952A to lock the outer cannula 951A in either the retracted position shown in FIG. 45 or the extended position relative to the inner cannula 952A. The lock rings 976 include a depression 977 sized to matingly engage the detent 975. As shown in FIG. 45, the outer cannula 951A is locked to the inner cannula 952A in the retracted position. The outer cannula 952A may be locked to the inner cannula 951A in any other manner known to one having ordinary skill in the art, for example, with a bayonet, cam-lock or threaded connection.

Operation of the second balloon cannula system 948A will now be described. Before being inserted into a patient, the second balloon cannula system 948A is configured in the extended position of FIG. 43 with the supporting portion 964A of the inner cannula 952A extending beyond the distal end of the outer cannula 951A and into the interior 965 of the balloon 954. The balloon 954 is deflated and preferably packed in a sheath (not shown) as described above. The detent 975 of the sleeve 972 is engaged with the depression 977 in the lock ring 976 thereby locking the outer cannula 951A in the extended position. An obturator (not shown) as described above is inserted through the port in the delivery device 949A with the blunt tip of the obturator extending beyond the distal end of the inner cannula 952A.

The balloon 954 is then inserted into a patient and advanced in the patient until the balloon is in the desired position for the dissection and/or retraction contemplated. The obturator is then removed and an endoscope (not shown) is then introduced through the port in the delivery device until the endoscope contacts the stop 961. The stop 961 is preferably configured so that the distal end of the endoscope is recessed from the distal end of the stop 961 between 2 mm and 10 mm and more preferably about 5 mm.

A suitable inflation device is then attached to the inflation port 953 and a suitable inflation fluid, as described above, is used to inflate the balloon 954. During inflation, the supporting portion 964A advantageously provides structural support for the balloon 964 so that the balloon 964 does not become skewed and off-center during inflation. The inflation fluid enters the balloon 964 through the fluid path 969A at least partially defined by the interior 971 of the inner cannula 952A. A preferred inflation device is a bulb (not shown) which delivers a controlled volume of the inflation fluid with each squeeze.

Once the balloon 954 is inflated, the inner and outer cannulas 952A, 951A are longitudinally movable relative to one another to provide optimal visualization of the tissue layers. During relative movement between the inner and outer cannulas 952A, 951A, the inflation fluid pressure is maintained in the balloon 954 by virtue of the substantially fluid tight seal provided by the first o-ring 974. Supplemental inflation fluid is provided through the inflation port 953 as necessary to make up for any fluid losses past the first o-ring 974.

B. Third Balloon Cannula System

Figure 46:
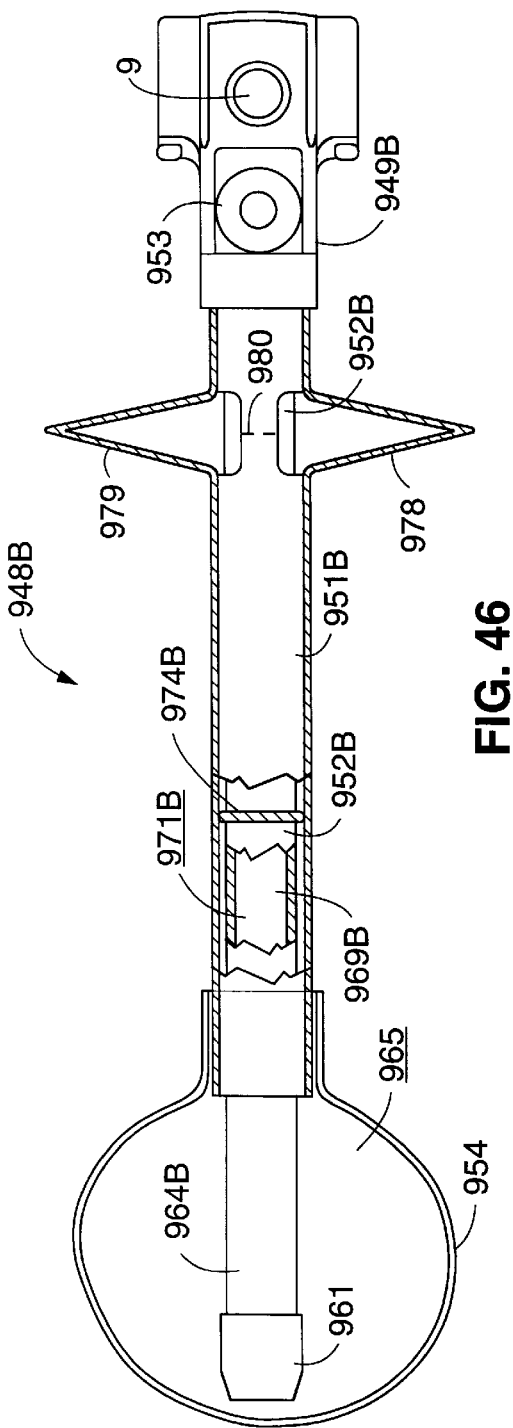
FIG. 46 shows a third balloon cannula system with the outer cannula having a contracting portion.
Figure 47:
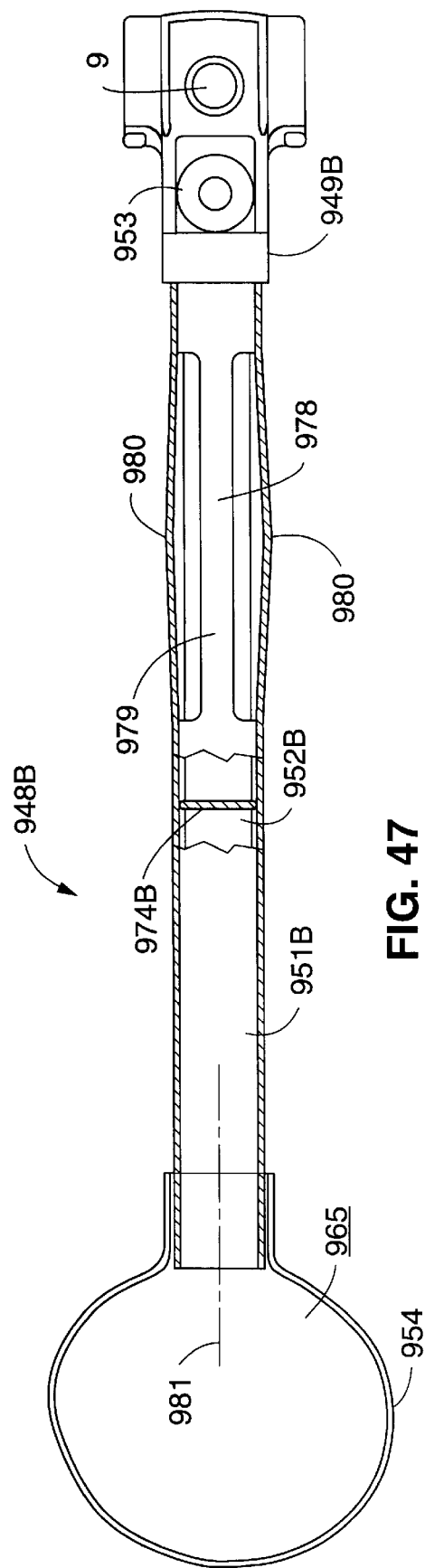
FIG. 47 shows the third balloon cannula system with the inner cannula in a retracted possition.

Referring to FIGS. 46 and 47, a third balloon cannula system 948B is shown. Similar items have the same reference numbers as described above in conjunction with the first and second balloon cannula systems 948, 948A except that a "B" has been added. The third balloon cannula system 948B includes a delivery device 949B and inner and outer cannulas 952B, 951B mounted to the delivery device 949B. The balloon 954, as described above, is mounted to the distal end of the outer cannula 951B. Once again, it is understood that the present invention may be practiced using any shape balloon and the balloon 954 is merely an example. An obturator (not shown), as described above, is also preferably provided for the reasons described above in conjunction with the first balloon cannula system 948.

The delivery device 949B is preferably the same as the delivery device 949A described above in conjunction with the first balloon cannula system 948. The delivery device 948B includes the inflation port 953 and the button 9 which activates the flapper valve (not shown). The inflation port 953 is fluidly coupled to a fluid path 969B which is at least partially defined by an interior 971B of the inner cannula 952B for inflating the balloon 954 with a suitable inflation fluid.

The outer cannula 951B includes a contracting portion 978 which contracts to change a longitudinal length of the outer cannula 951B. In the preferred embodiment the contracting portion 978 includes a number of deformable, longitudinally-extending segments 979. Referring to FIG. 47, the segments 979 are deformable along a fold line 980 so that the segments 979 bow outward (as shown in FIG. 46) and change the length of the outer cannula 951B in the direction of a longitudinal axis 981 of the inner cannula 951B. Although it is preferred to provide the segments 979, the contracting portion 978 may also be any other conventional mechanism such as an elastically displacable portion, a telescoping mechanism, or a threaded connection. When the contracting portion 978 is in the retracted position of FIG. 44, a supporting portion 964B of the inner cannula 952B extends beyond the distal end of the outer cannula 951B and into the interior 965 of the balloon 954. Referring to FIG. 47, when the segments 979 are deformed along the fold line 980, the supporting portion 964B is housed within the outer cannula 951B.

Referring to the partial cut-away of FIG. 46, a second o-ring 974B is coupled to the inner cannula 952B. The second o-ring 974B provides a substantially fluid tight seal between the inner and outer cannulas 952B, 951B so that inflation fluid pressure is maintained in the balloon 954.

Operation of the third balloon cannula system 948B will now be described. Before being inserted into a patient, the third balloon cannula system 948B is configured as shown in FIG. 46. The balloon 954 is deflated and preferably packed in a sheath (not shown) as described above. An obturator (not shown) is inserted through the port in the delivery device 949B with the blunt tip of the obturator extending beyond the distal end of the inner cannula 952B.

The balloon 954 is then inserted into a patient and advanced in the patient until the balloon 954 is in the desired position for dissection and/or retraction. The obturator is then removed and an endoscope (not shown) is introduced through port in the delivery device 949B until the endoscope contacts the stop 961 attached to the distal end of the inner cannula 952B. The stop 961 is the same as described above in conjunction with the first and second balloon cannula systems 948, 948A.

A suitable inflation device is then attached to the inflation port 953 and a suitable inflation fluid, as described above, is used to inflate the balloon 954. During inflation, the supporting portion 964B of the inner cannula 952B provides support for the balloon 954 so that the balloon 954 does not become skewed and off-center. The inflation fluid enters the balloon 954 through the fluid path 969B passing through the interior 971B of the inner cannula 952B.

The obturator is then removed and an endoscope is inserted into the port in the delivery device 949B. By virtue of the contracting portion 978, the inner and outer cannulas 952B, 951B are longitudinally movable relative to one another between the extended and retracted positions to provide optimal visualization of the tissue layers. During movement between the extended and retracted positions, the inflation fluid pressure is maintained by the fluid seal provided by the second o-ring 974B.

Modification and variation can be made to the disclosed embodiments without departing from the subject of the invention as defined by the following claims. For example, although it is preferred to provide a supporting portion which is part of an inner cannula or an outer cannula, the supporting portion may also be completely separate from the inner and outer cannulas. Furthermore, although it is preferred to provide a cylindrical supporting portion, the supporting portion may also be flared, conical, asymmetrical, or any other shape appropriate for the particular balloon shape and medical procedure.

We claim:

1. A device for separating tissue layers, comprising:
   a delivery device having an inflation port;
   a balloon having an interior;
   a fluid path fluidly coupling the inflation port and the interior of the balloon;
   an outer cannula having a distal end and a proximal end, the balloon being mounted to the distal end of the outer cannula;
   an inner cannula at least partially disposed within the outer cannula, the inner cannula having a supporting portion movable between an extended position relative to the outer cannula, in which the supporting portion is positioned within the interior of the balloon, and a retracted position relative to the outer cannula, in which the supporting portion is positioned outside the interior of the balloon, wherein the inner cannula is slidably coupled to the outer cannula so that the supporting portion is movable between the retracted position and the extended position relative to the interior of the balloon, and wherein at least one of the inner and outer cannulas is mounted to the delivery device; and
   an insert, wherein the inner cannula is a portion of the insert, wherein the outer cannula has an interior and is mounted to the delivery device, the delivery device includes a port leading to the interior of the outer cannula, and the insert passes through the port, and wherein the insert includes an opening and a lock, the opening being adapted to receive an endoscope and the lock being movable between a locked position, in which the endoscope is locked to the insert with a substantially fluid tight seal, and an unlocked position, in which the endoscope is unlocked with respect to the insert so that the endoscope is slidably movable relative to the insert.

2. A device for separating tissue layers, comprising:
   a delivery device having an inflation port;
   a balloon having an interior;
   a fluid path fluidly coupling the inflation port and the interior of the balloon;
   an outer cannula having a distal end and a proximal end, the balloon being mounted to the distal end of the outer cannula;
   an inner cannula at least partially disposed within the outer cannula, the inner cannula having a supporting portion movable between an extended position relative to the outer cannula, in which the supporting portion is positioned within the interior of the balloon, and a retracted position relative to the outer cannula, in which the supporting portion is positioned outside the interior of the balloon, wherein the inner cannula is slidably coupled to the outer cannula so that the supporting portion is movable between the retracted position and the extended position relative to the interior of the balloon, and wherein at least one of the inner and outer cannulas is mounted to the delivery device, wherein the inner cannula is mounted to the delivery device, and the proximal end of the outer cannula is slidably coupled to the inner cannula; and
   first and second lock rings mounted to the inner cannula, the first and second lock rings limiting slidable movement of the outer cannula between an extended cannula position relative to the inner cannula and a retracted cannula position relative to the inner cannula, respectively.

3. The device for separating tissue layers of claim 2, further comprising:
   a sleeve mounted to the outer cannula, the sleeve having a detent extending inwardly toward the inner cannula;
   the first lock ring being configured to matingly engage the detent to lock the inner and outer cannulas with the outer cannula in the retracted cannula position relative to the inner cannula.

4. The device for separating tissue layers of claim 3, further comprising:
   an elastomeric member coupled to the sleeve and contacting the inner cannula, the elastomeric member forming a substantially fluid tight seal between the sleeve and the inner cannula.

5. A device for separating tissue layers, comprising:
   a delivery device having an inflation port;
   a balloon having an interior;
   a fluid path fluidly coupling the inflation port and the interior of the balloon;
   an outer cannula having a distal end and a proximal end, the balloon being mounted to the distal end of the outer cannula; and
   an inner cannula at least partially disposed within the outer cannula, the inner cannula having a supporting portion movable between an extended position relative to the outer cannula, in which the supporting portion is positioned within the interior of the balloon, and a retracted position relative to the outer cannula, in which the supporting portion is positioned outside the interior of the balloon, wherein the inner cannula is slidably coupled to the outer cannula so that the supporting portion is movable between the retracted position and the extended position relative to the interior of the balloon, and wherein at least one of the inner and outer cannulas is mounted to the delivery device, wherein:

the inner cannula has a longitudinal axis and is mounted to the delivery device; and the proximal end of the outer cannula is mounted to the delivery device, the outer cannula having a contracting portion between the distal and proximal ends, the contracting portion changing a longitudinal length of the outer cannula in a direction of the longitudinal axis when the supporting portion moves from the extended position to the retracted position.

6. The device for separating tissue layers of claim 5, wherein:

the contracting portion of the outer cannula includes a number of longitudinally extending segments.

7. The device for separating tissue layers of claim 5, wherein:

at least a portion of the fluid path is housed within an interior of the inner cannula.

8. A device for separating tissue layers, comprising:

a delivery device having an inflation port;

an outer cannula having a distal end and being mounted to the delivery device;

an inflatable balloon having an interior and being mounted to the distal end of the outer cannula;

a fluid path fluidly coupling the inflation port and the interior of the balloon for inflating the balloon;

an insert having an inner cannula attached thereto, the insert being slidably coupled to the delivery device between a retracted position and an extended position, a portion of the inner cannula being housed within the outer cannula when the insert is in the retracted position and the portion of the inner cannula extending beyond the distal end of the outer cannula when the insert is in the extended position, the insert having an opening adapted to receive an endoscope, and the outer cannula having a proximal end slidably coupled to the inner cannula; and first and second lock rings mounted to the inner cannula, the first and second lock rings limiting slidable movement of the outer cannula between an extended cannula position relative to the inner cannula and a retracted cannula position relative to the inner cannula, respectively.

9. A method of separating tissue layers in a patient comprising the steps of:

(a) providing a delivery device, a balloon, a fluid path, an outer cannula, and an inner cannula slidably disposed at least partially within the outer cannula, wherein the inner cannula is attached to the delivery device, wherein the inner cannula has a supporting portion, the delivery device has an inflation port, the fluid path fluidly couples an interior of the balloon to the inflation port, and the outer cannula is slidably coupled to the inner cannula, the outer and inner cannulas being slidably coupled to one another between an extended position in which the supporting portion extends into the interior of the balloon, and a retracted position in which the supporting portion is housed within the outer cannula;

(b) inserting the balloon into the patient between said tissue layers;

(c) inflating the balloon through the inflation port and the fluid path, the supporting portion providing support for the balloon during inflation, (d) removing the supporting portion from the interior of the balloon by sliding the outer cannula from the extended position to the retracted position; and (e) locking the outer cannula in the extended position during step (c).

10. A method of separating tissue layers in a patient, comprising the steps of:

(a) providing a delivery device, a balloon, a fluid path, an outer cannula, an inner cannula slidably disposed at least partially within the outer cannula, and an insert slidably coupled to the delivery device, wherein the outer cannula is attached to the delivery device, the inner cannula has a supporting portion, the delivery device has an inflation port, the fluid path fluidly couples an interior of the balloon to the inflation port, the supporting portion of the inner cannula is positioned within the interior of the balloon, and the insert has the inner cannula attached thereto;

(b) inserting the balloon into the patient between said tissue layers;

(c) inflating the balloon through the inflation port and the fluid path, the supporting portion providing support for the balloon during inflation;

(d) removing the supporting portion from the interior of the balloon by sliding at least one of the outer cannula and the inner cannula relative to another of the inner cannula and the outer cannula;

(e) after step (d), inserting an endoscope into the interior of the balloon;

locking the insert to the delivery device before initiating step (c); and unlocking the insert from the delivery device after step (c) but before step (d).

11. A method of separating tissue layers in a patient, comprising the steps of:

(a) providing a delivery device, a balloon, a fluid path, an outer cannula, an inner cannula slidably disposed at least partially within the outer cannula, and an insert slidably coupled to the delivery device, wherein the outer cannula is attached to the delivery device, the inner cannula has a supporting portion, the delivery device has an inflation port, the fluid path fluidly couples an interior of the balloon to the inflation port, the supporting portion of the inner cannula is positioned within the interior of the balloon, and the insert has the inner cannula attached thereto;

(b) inserting the balloon into the patient between said tissue layers;

(c) inflating the balloon through the inflation port and the fluid path, the supporting portion providing support for the balloon during inflation;

(d) removing the supporting portion from the interior of the balloon by sliding at least one of the outer cannula and the inner cannula relative to another of the inner cannula and the outer cannula;

(e) inserting an endoscope through an opening in the insert into the interior of the balloon; and (f) locking the endoscope to the insert.

12. The method of separating tissue layers in a patient of claim 11, wherein:

the removing step is carried out by sliding the insert to a retracted position after the endoscope locking step, at least a part of the supporting portion being housed within the outer cannula when in the retracted position.

13. A method of separating tissue layers in a patient comprising the steps of:

(a) providing a delivery device, a balloon, a fluid path, an outer cannula, an inner cannula slidably disposed at least partially within the outer cannula, wherein at least one of the outer cannula and the inner cannula is attached to the delivery device, wherein the inner cannula has a supporting portion, the delivery device has an inflation port, the fluid path fluidly couples an interior of the balloon to the inflation port, and the supporting portion is positioned within the interior of the balloon;

(b) inserting the balloon into the patient between said tissue layers;

(c) inflating the balloon through the inflation port and the fluid path, the supporting portion providing support for the balloon during inflation; and (d) removing the supporting portion from the interior of the balloon by sliding at least one of the outer cannula and the inner cannula relative to another of the inner cannula and the outer cannula, wherein:

step (a) is carried out by providing the inner cannula and the outer cannula to be mounted to the delivery device and the balloon to be mounted to the outer cannula, the outer cannula having a contracting portion which is movable between an extended position, in which the supporting portion extends into the interior of the balloon, and a retracted position, in which the supporting portion is housed within the outer cannula.

14. The method of separating tissue layers in a patient of claim 13, further comprising the step of:

contracting the contracting portion from the extended position to the retracted position after initiating step (c).

* * * * *